US012668769B2

(12) United States Patent
Greenshields et al.

(10) Patent No.: US 12,668,769 B2
(45) Date of Patent: *Jun. 30, 2026

(54) STABLE INOCULANT COMPOSITIONS AND METHODS FOR PRODUCING SAME

(71) Applicants:Novozymes BIOAG A/S, Bagsvaerd (DK); Monsanto Technology LLC, St Louis, MO (US)

(72) Inventors: Dave Greenshields, Saskatchewan (CA); Kristi Woods, Blacksburg, VA (US); Shaun Raj Selness, Chesterfield, MO (US); Hui Han, Chesterfield, MO (US)

(73) Assignee: Novozymes BIOAG A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/440,328

(22) Filed: Feb. 13, 2024

(65) Prior Publication Data

US 2024/0254432 A1 Aug. 1, 2024

Related U.S. Application Data

(60) Continuation of application No. 17/223,154, filed on Apr. 6, 2021, now Pat. No. 12,077,746, which is a division of application No. 16/066,377, filed as application No. PCT/US2016/067745 on Dec. 20, 2016, now Pat. No. 11,076,603.

(60) Provisional application No. 62/296,784, filed on Feb. 18, 2016, provisional application No. 62/271,873, filed on Dec. 28, 2015.

(51) Int. Cl.
| | |
|---|---|
| *C12N 1/04* | (2006.01) |
| *A01N 25/00* | (2006.01) |
| *A01N 25/02* | (2006.01) |
| *A01N 25/04* | (2006.01) |
| *A01N 25/30* | (2006.01) |
| *A01N 63/30* | (2020.01) |
| *A01N 63/36* | (2020.01) |
| *C12N 1/14* | (2006.01) |
| *C12N 1/145* | (2026.01) |
| *C12R 1/80* | (2006.01) |

(52) U.S. Cl.
CPC .............. *C12N 1/04* (2013.01); *A01N 25/04* (2013.01); *A01N 25/30* (2013.01); *A01N 63/30* (2020.01); *A01N 63/36* (2020.01); *C12N 1/14* (2013.01); *C12N 1/145* (2021.05); *A01N 2300/00* (2013.01); *C12R 2001/80* (2021.05)

(58) Field of Classification Search
CPC . C12N 1/04; C12N 1/14; C12N 1/145; A01N 25/04; A01N 25/30; A01N 63/30; A01N 63/36; A01N 2300/00; A01N 25/02; A01N 47/14; C12R 2001/80; A01C 1/06
See application file for complete search history.

(56) References Cited

U.S. PATENT DOCUMENTS

| | | | |
|---|---|---|---|
| 5,484,464 | A | 1/1996 | Gleddie et al. |
| 5,586,411 | A | 12/1996 | Gleddie et al. |
| 5,695,541 | A | 12/1997 | Kosanke et al. |
| 5,804,208 | A | 9/1998 | Andersch et al. |
| 5,916,029 | A | 6/1999 | Smith et al. |
| 6,569,425 | B2 | 5/2003 | Drahos et al. |
| 6,808,917 | B1 | 10/2004 | Johnson |
| 6,824,772 | B2 | 11/2004 | Drahos et al. |
| 7,429,477 | B2 | 9/2008 | Johnson |
| 8,011,132 | B2 | 9/2011 | Pearce et al. |
| 8,148,138 | B2 | 4/2012 | Johnson |
| 8,278,247 | B2 | 10/2012 | Hnatowich et al. |
| 8,445,256 | B2 | 5/2013 | Woods et al. |
| 8,883,679 | B2 | 11/2014 | Woods et al. |
| 8,921,089 | B2 | 12/2014 | Kang et al. |
| 8,999,698 | B2 | 4/2015 | Kang et al. |
| 9,017,442 | B2 | 4/2015 | Johnson |
| 9,090,884 | B2 | 7/2015 | Harman et al. |
| 9,101,088 | B2 | 8/2015 | Hnatowich et al. |
| 9,234,251 | B2 | 1/2016 | Snyder et al. |
| 9,340,464 | B2 | 5/2016 | Hnatowich et al. |
| 10,856,552 | B2 | 12/2020 | Greenshields et al. |
| 11,076,603 | B2 | 8/2021 | Greenshields et al. |
| 2008/0107689 | A1 | 5/2008 | Seiskari |
| 2014/0143909 | A1 | 5/2014 | Greenshields et al. |
| 2015/0230478 | A1 | 8/2015 | Vujanovic et al. |

FOREIGN PATENT DOCUMENTS

| | | |
|---|---|---|
| CA | 2254431 A1 | 11/1998 |
| CN | 86102971 A | 12/1986 |
| CN | 1489476 A | 4/2004 |
| CN | 1922305 A | 2/2007 |
| CN | 101106900 A | 1/2008 |
| CN | 101341818 A | 1/2009 |
| CN | 101709277 A | 5/2010 |

(Continued)

OTHER PUBLICATIONS

Monsanto Company, 2015, Safety Data Sheet, Commercial Product.

(Continued)

*Primary Examiner* — Satyendra K Singh

(74) *Attorney, Agent, or Firm* — Adam Rucker

(57) ABSTRACT

The present disclosure provides aqueous inoculant compositions and methods for enhancing the survival and/or stability of microbial spores in an inoculant composition. In some embodiments, aqueous inoculant compositions of the present disclosure comprise microbial spores, one or more dispersants, one or more protectants, one or more aqueous additives and a non-aqueous liquid carrier.

25 Claims, 2 Drawing Sheets

(56) References Cited

FOREIGN PATENT DOCUMENTS

| CN | 102070368 | A | 5/2011 |
|---|---|---|---|
| CN | 102246750 | A | 11/2011 |
| CN | 102433287 | A | 5/2012 |
| CN | 102459568 | A | 5/2012 |
| CN | 102987055 | A | 3/2013 |
| CN | 103039439 | A | 4/2013 |
| CN | 103140145 | A | 6/2013 |
| CN | 103283948 | A | 9/2013 |
| CN | 103347395 | A | 10/2013 |
| CN | 103404703 | A | 11/2013 |
| CN | 103421693 | A | 12/2013 |
| CN | 103444786 | A | 12/2013 |
| CN | 103766407 | A | 5/2014 |
| CN | 103787758 | A | 5/2014 |
| CN | 103911314 | A | 7/2014 |
| CN | 104080337 | A | 10/2014 |
| CN | 104255809 | A | 1/2015 |
| CN | 104628485 | A | 5/2015 |
| CN | 104797701 | A | 7/2015 |
| CN | 105101776 | A | 11/2015 |
| CN | 106190929 | A | 12/2016 |
| EP | 0203708 | A1 | 12/1986 |
| EP | 0906951 | A2 | 4/1999 |
| JP | 45021632 | B | 7/1970 |
| JP | 2002176969 | A | 6/2002 |
| JP | 2004231626 | A | 8/2004 |
| JP | 2006124337 | A | 5/2006 |
| JP | 2008525022 | A | 7/2008 |
| JP | 2009540825 | A | 11/2009 |
| JP | 2013516193 | A | 5/2013 |
| JP | 2014501500 | A | 1/2014 |
| JP | 2015519051 | A | 7/2015 |
| JP | 2019503714 | A | 2/2019 |
| JP | 2022010176 | A | 1/2022 |
| RU | 2345975 | C2 | 2/2009 |
| RU | 2428467 | C2 | 9/2011 |
| SU | 922104 | A1 | 4/1982 |
| UA | 26928 | C1 | 12/1999 |
| WO | 9957959 | A1 | 11/1999 |
| WO | 2005095580 | A1 | 10/2005 |
| WO | 2006071369 | A2 | 7/2006 |
| WO | 2008002371 | A1 | 1/2008 |
| WO | 2009010561 | A1 | 1/2009 |
| WO | 2009049747 | A2 | 4/2009 |
| WO | 2010037228 | A1 | 4/2010 |
| WO | 2011085221 | A2 | 7/2011 |
| WO | 2012058730 | A1 | 5/2012 |
| WO | 2013044208 | A2 | 3/2013 |
| WO | 2013044214 | A1 | 3/2013 |
| WO | 2013090628 | A1 | 6/2013 |
| WO | 2013096883 | A2 | 6/2013 |
| WO | 2013169923 | A2 | 11/2013 |
| WO | 2014138490 | A1 | 9/2014 |
| WO | 2014160827 | A1 | 10/2014 |
| WO | 2015003908 | A1 | 1/2015 |
| WO | 2015063090 | A2 | 5/2015 |
| WO | 2015069708 | A1 | 5/2015 |
| WO | 2015100432 | A2 | 7/2015 |
| WO | 2015130911 | A1 | 9/2015 |
| WO | 2017044473 | A1 | 3/2017 |
| WO | 2017044545 | A1 | 3/2017 |
| WO | 2017116837 | A1 | 7/2017 |
| WO | 2017116846 | A1 | 7/2017 |
| WO | 2017131971 | A1 | 8/2017 |

OTHER PUBLICATIONS

Patil et al., 2012, International journal of environmental sciences, 3(3), 1116-1129.
Torres et al., 2003, Journal of Applied Microbiology, 94, 330-339.
Universitet China Agricultural, 2011, Abstract of CN102070368.
Anonymous, 2013, JumpStart LCO, 1-2.
Bashan et al., 2014, Plant and Soil, 378(1), 1-33.
Behboudi-Jobbehdar et al., 2013, Drying Technology, 31(11), 1274-1283.
Boos et al., 1998, Microbiology and Molecular Biology Reviews, 62(1), 204-229.
Campos et al., 2014, World J Microbiol Biotechnol, 30(9), 2371-2378.
Chi et al., 2005, Applied and Environmental Microbiology, 71(11), 7271-7278.
Colaco et al., 1992, Biotechnology, 10(9), 1007-1011.
Cruz et al., 2012, Structure and Function of Food Engineering, 2, 21-42.
Cunningham et al., 1990, Can. J. Bot., 68(10), 2270-2274.
Diange et al., 2013, Curr Microbiol, 66(6), 599-605.
Elizabeth et al., 2004, Starch-Starke, 56(2), 58-62.
Friesen et al., 2005, Appl Microbiol Biotechnol, 68(3), 397-404.
Fu et al., 2008, China Traditional Chinese Medicine Press, 109-112.
Fu et al., 2011, Food Research International, 44(5), 1127-1149.
Gaucher, 2020, 5 Benefits of Lactobacillus bacteria, 1-7.
Guangzhou Glam Biotechnology Co Ltd., 2013, abstract of CN103283948A.
Guangzhou Glam Biotechnology Co. Ltd., 2013, abstract of CN103404703A.
Harbin Inst of Technology, 2010, abstract of CN101709277A.
Harti et al., 2015, International Journal of Pharma Medicine and Biological Sciences, 4(3), 204-208.
Haytowitz et al., 2007, Usda, 280S-281S.
Hofman et al., 2016, Critical Reviews Food Science and Nutrition, 56(12), 2091-2100.
Ibatsam et al., 2012, African Journal of food, 12(3), 6055-6064.
Idemitsu Kosan Co et al., 2005, Abstract of WO2005095580A1.
Kawai et al., 2005, Pharmaceutical Research, 22(3), 490-495.
Kleespies et al., Biocontrol Science and Technology, 4, 309-319, 1994.
Lal et al., 2013, Vaccine, 31, 4759-4764.
Li Xueping, 2013, abstract of CN102987055A.
Mary et al., 1994, Soil Biol. Biochem., 26(9), 1125-1132.
Meng Honglin, 2015, abstract of CN104628485A.
Novozymes Bioag, 2013, Extended Label Internet website.
Oldenhof et al., 2005, Biotechnol. Prog., 21(3), 885-892.
Oregel-Zamudio et al., 2017, Scientia Horticulturae, 214, 273-279.
Pispan et al., 2013, Food and Bioproducts Processing, 91, 362-369.
Rinaudo, 2006, Progress in Polymer Science, 31(7), 603-632.
Rong et al., 2009, Journal of Food Science, 74(1), C33-C40.
Scarmeas et al., 2018, The Lancet Neurology, 17, 1006-1015.
Schoebitz et al., 2013, Agronomy for Sustainable Development, 33(4), 751-765.
Semyonov et al., 2011, LWT—Food Science and Technology, 44(9), 1844-1852.
Shahidi et al., 1993, Critical Reviews in Food Science and Nutrition, 33(6), 501-547.
Streeter, 2003, Journal of Applied Microbiology, 95(3), 484-491.
Takahashi, 1967, The Japanese Journal of Tuberculosis, 14(3-4), 67-95.
Vnii Sel'skokhozyaystvennoy Mikrobiologii Inst et al. 1982, abstract of SU922104A1.
Yao et al., 2007, China traditional Chinese Medicine Press, 232-234.
Zhang(Ed) et al., 2009, China Light Industry Press, 291.
Zhao(Ed) et al., 1988, Beijing Agricultural University Press, 228.
Zhao(Ed), 1986, China Agricultural Press, 497-499.
Zongyang County Baiyun Ecological Garden Co. Ltd., 2014, abstract of CN103787758A.

*P. bilaiae* titre (avg log10 per seed) at 10°C or 20°C over time (in weeks)
(10°C w/ LCO = triangle; 10°C w/out LCO = diamond;
20°C w/ LCO = X; 20°C w/out LCO = square)

STABLE INOCULANT COMPOSITIONS AND METHODS FOR PRODUCING SAME

CROSS-REFERENCE TO RELATED APPLICATIONS

This application is a continuation of U.S. patent application Ser. No. 17/223,154, filed Apr. 6, 2021, which is a Continuation of U.S. patent application Ser. No. 16/066,377, filed Jun. 27, 2018, and issued as U.S. Pat. No. 11,076,603 on Aug. 3, 2021, which is a 35 U.S.C. 371 national stage entry of International Patent Application No. PCT/US2016/067745, filed Dec. 20, 2016, which claims priority to U.S. Provisional Patent Application Nos. 62/271,873, filed Dec. 28, 2015, and 62/296,784, filed Feb. 18, 2016. Each of the aforementioned applications is fully incorporated herein by reference in its entirety.

FIELD OF THE INVENTION

The present disclosure relates to compositions and methods for enhancing the stability and survival of microbial spores in inoculant compositions.

BACKGROUND OF THE INVENTION

Inoculant compositions comprising agriculturally beneficial microorganisms are well known in the art. See, e.g., U.S. Pat. Nos. 5,484,464; 5,586,411; 5,695,541; 5,804,208; 5,916,029; 6,569,425; 6,808,917; 6,824,772; 7,429,477; 8,148,138; 8,278,247; 8,445,256; 8,883,679; 8,921,089; 8,999,698; 9,017,442; 9,101,088; 9,234,251; 9,340,464.

Because the effectiveness of such inoculant compositions generally depends on the ability of the microorganisms therein to survive and propagate following application, much effort has been made to increase the stability of agriculturally beneficial microorganisms in inoculant compositions. See, e.g., U.S. Pat. No. 8,011,132 (describing a method of adding trehalose, sucrose or glycerol to the substantially stationary phase of fermentation) and 9,090,884 (describing the microencapsulation of microorganisms in a water-soluble encapsulating material).

Nevertheless, there remains a need for improved compositions and methods for enhancing the stability and survival of microorganisms in inoculant compositions.

SUMMARY OF THE CLAIMED INVENTION

The present disclosure provides stable inoculant compositions and methods for enhancing the survival and/or stability of microbial spores in inoculant compositions.

A first aspect of the present disclosure is an aqueous inoculant composition comprising *Penicillium* spores, one or more dispersants, one or more protectants, one or more aqueous additives and a non-aqueous liquid carrier. In some embodiments, the inoculant composition comprises one or more pesticides, one or more lipo-chitooligosaccharides, one or more chitooligosaccharides, one or more chitinous compounds, one or more flavonoids and/or one or more drying agents.

A second aspect of the present disclosure is a coated plant propagation material comprising a plant propagation material and a coating that covers at least a portion of an outer surface of the plant propagation material, said coating comprising an aqueous inoculant composition of the present disclosure.

A third aspect of the present disclosure is a kit comprising a coated plant propagation material of the present disclosure and a container housing the coated plant propagation material.

A fourth aspect of the present disclosure is a plant germinated from a coated plant propagation material of the present disclosure.

A fifth aspect of the present disclosure is a plant part harvested from a plant that was germinated from a coated plant propagation material of the present disclosure.

A sixth aspect of the present disclosure is a processed product derived from a plant that was germinated from a coated plant propagation material of the present disclosure.

A seventh aspect of the present disclosure is a crop comprising a plurality of plants germinated from coated plant propagation materials of the present disclosure.

An eighth aspect of the present disclosure is a method that comprises applying an aqueous inoculant composition of the present disclosure to a plant propagation material.

A ninth aspect of the present disclosure is a method that comprises, consists essentially of or consisting of planting a coated plant propagation material of the present disclosure.

DETAILED DESCRIPTION

Figure 1:
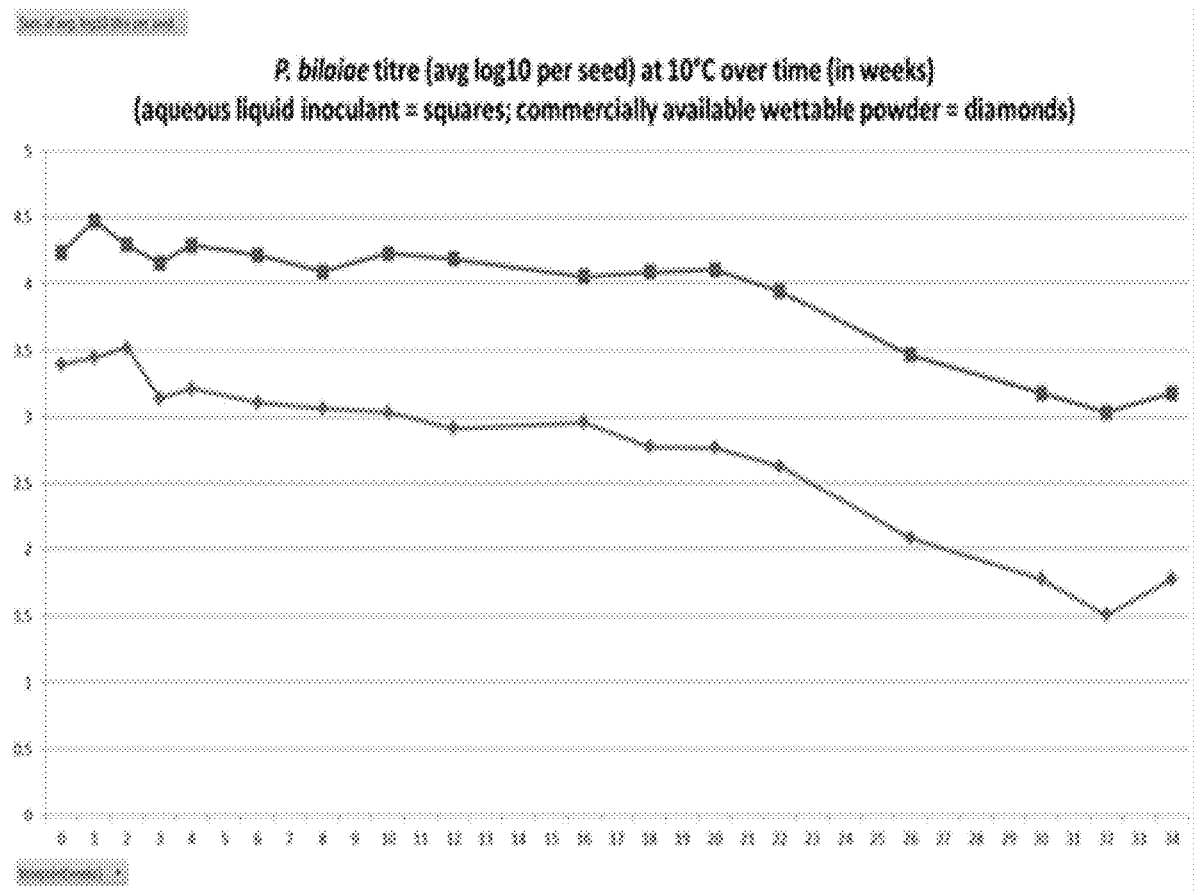
FIG. 1 is a graph showing the survivability of *Penicillium bilaiae* spores on corn seeds stored at 10° C. and 50% relative humidity.

The present disclosure is explained in greater detail below. This description is not intended to be a detailed catalog of all the different ways in which the invention may be implemented or of all the features that may be added to the instant invention. For example, features illustrated with respect to one embodiment may be incorporated into other embodiments and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following specification is intended to illustrate some particular embodiments of the invention and not to exhaustively specify all permutations, combinations and variations thereof.

The terminology used herein is for the purpose of describing particular embodiments only and is not intended to be limiting of the invention.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. For the sake of brevity and/or clarity, well-known functions or constructions may not be described in detail.

As used herein, the singular forms "a," "an," and "the" are intended to include the plural forms as well, unless the context clearly indicates otherwise. Thus, unless the context clearly indicates otherwise, "a maltodextrin" is to be interpreted as "one or more maltodextrins," "a microorganism" is to be interpreted as "one or more microorganisms," "a lipo-chitooligosaccharide" is to be interpreted as "one or more lipo-chitooligosaccharides," etc.

As used herein, the term "about," when used in reference to a measurable value such as an amount of mass, dose, time, temperature and the like, is meant to encompass variations of 0.1%, 0.25%, 0.5%, 0.75%, 1%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19% or 20% of the specified amount. Unless otherwise indicated, all numerical values in the specification are to be understood as being modified by the term "about."

As used herein, the term "agriculturally beneficial agent" refers to any agent (e.g., chemical or biological agent) or combination of agents the application of which causes or provides a beneficial and/or useful effect in agriculture including, but not limited to, agriculturally beneficial microorganisms, biostimulants, nutrients, pesticides (e.g., fungicides, herbicides, insecticides, and nematicides) and plant signal molecules.

As used herein, the term "agriculturally beneficial microorganism" refers to a microorganism having at least one agriculturally beneficial property (e.g., the ability to fix nitrogen, the ability to solubilize phosphate and/or the ability to produce an agriculturally beneficial agent, such as a plant signal molecule).

As used herein, the term "agriculturally acceptable carrier" refers to a material that can be used to deliver an agriculturally beneficial agent to a plant, plant part or plant growth medium (e.g., soil). As used herein, the term "soil-compatible carrier" refers to a material that can be added to a soil without causing/having an unduly adverse effect on plant growth, soil structure, soil drainage, or the like. As used herein, the term "seed-compatible carrier" refers to a material that can be added to a seed without causing/having an unduly adverse effect on the seed, the plant that grows from the seed, seed germination, or the like. As used herein, the term "foliar-compatible carrier" refers to a material that can be added to a plant or plant part without causing/having an unduly adverse effect on the plant, plant part, plant growth, plant health, or the like.

As used herein, the term "and/or" is intended to include any and all combinations of one or more of the associated listed items, as well as the lack of combinations when interpreted in the alternative ("or").

As used herein, the term "aqueous" refers to a composition that contains more than a trace amount of water (i.e., more than 0.5% water by weight, based upon the total weight of the composition).

As used herein, the term "biostimulant" refers to an agent or combination of agents the application of which enhances one or more metabolic and/or physiological processes of a plant or plant part (e.g., carbohydrate biosynthesis, ion uptake, nucleic acid uptake, nutrient delivery, photosynthesis and/or respiration).

As used herein, the term "colony forming unit" refers to a microbial cell/spore capable of propagating on or in a substrate (e.g., a soil) when conditions (e.g., temperature, moisture, nutrient availability, pH, etc.) are favorable for microbial growth.

As used herein, the terms "comprise," "comprises," "comprising," "include," "includes" and "including" specify the presence of stated features, steps, operations, elements and/or components, but do not preclude the presence or addition of one or more other features, steps, operations, elements, components and/or groups thereof.

As used herein, the term "consists essentially of" (and grammatical variants thereof), as applied to the compositions and methods of the present disclosure, means that the compositions/methods may contain additional components so long as the additional components do not materially alter the composition/method. The term "materially alter," as applied to a composition/method, refers to an increase or decrease in the effectiveness of the composition/method of at least about 20% or more. For example, a component added to an inoculant composition of the present disclosure "materially alters" the composition if it increases or decreases the composition's ability to enhance microbial survival by at least about 50%.

As used herein, the term "diazotroph" refers to an organism capable of converting atmospheric nitrogen ($N_2$) into a form that may be utilized by a plant or plant part (e.g., ammonia ($NH_3$), ammonium ($NH_4+$), etc.).

As used herein, the terms "effective amount," "effective concentration," and "effective dosage" (and grammatical variants thereof) refer to an amount, concentration or dosage that is sufficient to cause a desired effect (e.g., enhanced microbial survival). The absolute value of the amount/concentration/dosage that is sufficient to cause the desired effect may be affected by factors such as the type and magnitude of effect desired, the type, size and volume of seeds to which the inoculant compositon will be applied, the stability of the microorganisms in the inoculant composition and the storage conditions (e.g., temperature, relative humidity, duration). Those skilled in the art will understand how to select an effective amount/concentration/dosage using routine dose-response experiments.

As used herein, the term "enhanced dispersion" refers to an improvement in one or more characteristics of microbial dispersion as compared to one or more controls (e.g., a control composition that is identical to an inoculant composition of the present disclosure except that it lacks one or more of the components found in the inoculant composition of the present disclosure). Exemplary microbial dispersion characteristics include, but are not limited to, the percentage of microbes that exist as single cells/spores when the inoculant composition is diluted in water. An inoculant composition that improves one or more microbial dispersion characteristics of the microorganism(s) contained therein as compared to a control composition (e.g., a control composition that is identical to the inoculant composition except that it lacks one or more of the components found in the inoculant composition) provides enhanced dispersion and can be referred to as a "readily dispersable inoculant composition."

As used herein, the terms "enhanced growth" and "enhanced plant growth" refer to an improvement in one or more characteristics of plant growth and/or development as compared to one or more control plants (e.g., a plant germinated from an untreated seed or an untreated plant). Exemplary plant growth/development characteristics include, but are not limited to, biomass, carbohydrate biosynthesis, chlorophyll content, cold tolerance, drought tolerance, height, leaf length, leaf mass, leaf number, leaf surface area, leaf volume, nutrient uptake (e.g., calcium, magnesium, nitrogen, phosphorous and/or potassium uptake), rate(s) of photosynthesis, root area, root diameter, root length, root mass, root nodulation (e.g., nodule mass, nodule number, nodule volume), root number, root surface area, root volume, salt tolerance, seed germination, seedling emergence, shoot diameter, shoot length, shoot mass, shoot number, shoot surface area, shoot volume, spread, stomatal conductance and survival rate. Unless otherwise indicated, references to enhanced plant growth are to be interpreted as meaning that compositions and methods of the present disclosure may be capable of enhancing plant growth by enhancing nutrient availability, improving soil characteristics, etc. and are not to be interpreted as suggesting that compositions and methods of the present disclosure act as plant growth regulators.

As used herein, the term "enhanced stability" refers to an improvement in one or more characteristics of microbial stability as compared to one or more controls (e.g., a control composition that is identical to an inoculant composition of the present disclosure except that it lacks one or more of the components found in the inoculant composition of the present disclosure). Exemplary microbial stability characteristics include, but are not limited to, the ability to cause a desired effect (e.g., enhanced plant yield and/or increased pesticidal activity) after being coated on a seed and/or stored for a defined period of time and survival rate after being coated on a seed and/or stored for a defined period of time. A microorganism that exhibits improvement in one or more microbial stability characteristics as compared to a control microorganism when each is subjected to the same conditions (e.g., seed coating and storage conditions) displays enhanced stability and can be referred to as a "stable microorganism." An inoculant composition that improves one or more microbial stability characteristics of the microorganism(s) contained therein as compared to a control composition (e.g., a control composition that is identical to the inoculant composition except that it lacks one or more of the components found in the inoculant composition) provides enhanced stability and can be referred to as a "stable inoculant composition."

As used herein, the term "enhanced survival" refers to an improvement in the survival rate of one or more microorganisms in an inoculant composition as compared to one or more microorganisms in a control composition (e.g., a control composition that is identical to an inoculant composition of the present disclosure except that it lacks one or more of the components found in the inoculant composition of the present disclosure). An inoculant composition that improves the survival rate of one or more of the microorganisms contained therein as compared to a control composition (e.g., a control composition that is identical to the inoculant composition except that it lacks one or more of the components found in the inoculant composition) provides enhanced survival and can be referred to as a stable inoculant composition.

As used herein, the terms "enhanced yield" and "enhanced plant yield" refer to an improvement in one or more characteristics of plant yield as compared to one or more control plants (e.g., a control plant germinated from an untreated seed). Exemplary plant yield characteristics include, but are not limited to, biomass; bushels per acre; grain weight per plot (GWTPP); nutritional content; percentage of plants in a given area (e.g., plot) that fail to produce grain; yield at standard moisture percentage (YSMP), such as grain yield at standard moisture percentage (GYSMP); yield per plot (YPP), such as grain weight per plot (GWTPP); and yield reduction (YRED). Unless otherwise indicated, references to enhanced plant yield are to be interpreted as meaning that compositions and methods of the present disclosure may be capable of enhancing plant yield by enhancing nutrient availability, improving soil characteristics, etc. and are not to be interpreted as suggesting that compositions and methods of the present disclosure act as plant growth regulators. As used herein, the term "foliage" refers to those portions of a plant that normally grow above the ground, including, but not limited to, leaves, stalks, stems, flowers, fruiting bodies and fruits.

As used herein, the terms "foliar application," "foliarly applied" and grammatical variations thereof, refer to the application of one or more active ingredients to the foliage of a plant (e.g., to the leaves of the plant). Application may be effected by any suitable means, including, but not limited to, spraying the plant with a composition comprising the active ingredient(s). In some embodiments, the active ingredient(s) is/are applied to the leaves, stems and/or stalk of the plant and not to the flowers, fruiting bodies or fruits of the plant.

As used herein, the term "glass transition temperature" and its abbreviation "Tg" refer to the midpoint of the temperature range over which a composition transitions from a glassy state to a rubbery state.

As used herein, the term "glassy state" refers to an amorphous solid.

As used herein, the term "humic acid" encompasses pure humic acids and humic acid salts (humates). Non-limiting examples of humic acids include ammonium humate, boron humate, potassium humate, sodium humate, etc.

In some embodiments, the humic acid comprises, consists essentially of or consists of one or more of MDL Number MFCD00147177 (CAS Number 1415-93-6), MDL Number MFCD00135560 (CAS Number 68131-04-4), MDL Number MFCS22495372 (CAS Number 68514-28-3), CAS Number 93924-35-7, and CAS Number 308067-45-0.

As used herein, the terms "inoculant composition" and "inoculum" refer to compositions comprising microbial cells and/or spores, said cells/spores being capable of propagating on or in a substrate (e.g., a soil) when conditions (e.g., temperature, moisture, nutrient availability, pH, etc.) are favorable for microbial growth.

As used herein, the term "isomer" includes all stereoisomers of the compounds and/or molecules to which it refers, including enantiomers and diastereomers, as well as all conformers, roatmers and tautomers, unless otherwise indicated. Compounds and/or molecules disclosed herein include all enantiomers in either substantially pure levorotatory or dextrorotatory form, or in a racemic mixture, or in any ratio of enantiomers. Where embodiments disclose a (D)-enantiomer, that embodiment also includes the (L)-enantiomer; where embodiments disclose a (L)-enantiomer, that embodiment also includes the (D)-enantiomer. Where embodiments disclose a (+)-enantiomer, that embodiment also includes the (−)-enantiomer; where embodiments disclose a (−)-enantiomer, that embodiment also includes the (+)-enantiomer. Where embodiments disclose a (S)-enantiomer, that embodiment also includes the (R)-enantiomer; where embodiments disclose a (R)-enantiomer, that embodiment also includes the (S)-enantiomer. Embodiments are intended to include any diastereomers of the compounds and/or molecules referred to herein in diastereomerically pure form and in the form of mixtures in all ratios. Unless stereochemistry is explicitly indicated in a chemical structure or chemical name, the chemical structure or chemical name is intended to embrace all possible stereoisomers, conformers, rotamers and tautomers of compounds and/or molecules depicted.

As used herein, the term "modified microbial strain" refers to a microbial strain that is modified from a strain isolated from nature. Modified microbial strains may be produced by any suitable method(s), including, but not limited to, chemical or other form of induced mutation to a polynucleotide within any genome within the strain; the insertion or deletion of one or more nucleotides within any genome within the strain, or combinations thereof; an inversion of at least one segment of DNA within any genome within the strain; a rearrangement of any genome within the strain; generalized or specific transduction of homozygous or heterozygous polynucleotide segments into any genome within the strain; introduction of one or more phage into any genome of the strain; transformation of any strain resulting in the introduction into the strain of stably replicating autonomous extrachromosomal DNA; any change to any genome or to the total DNA composition within the strain isolated from nature as a result of conjugation with any different microbial strain; and any combination of the foregoing. The term modified microbial strains includes a strain with (a) one of more heterologous nucleotide sequences, (b) one or more non-naturally occurring copies of a nucleotide sequence isolated from nature (i.e., additional copies of a gene that naturally occurs in the microbial strain from which the modified microbial strain was derived), (c) a lack of one or more nucleotide sequences that would otherwise be present in the natural reference strain by for example deleting nucleotide sequence, and (d) added extrachromosomal DNA. In some embodiments, modified microbial strains comprise a combination of two or more nucleotide sequences (e.g., two or more naturally occurring genes that do not naturally occur in the same microbial strain) or comprise a nucleotide sequence isolated from nature at a locus that is different from the natural locus.

As used herein, the term "non-aqueous" refers to a composition that comprises no more than a trace amount of water (i.e., no more than 0.5% water by weight, based upon the total weight of the composition).

As used herein, the term "nutrient" refers to a compound or element useful for nourishing a plant (e.g., vitamins, macrominerals, micronutrients, trace minerals, organic acids, etc. that are necessary for plant growth and/or development).

As used herein, the term "onset temperature" refers to the temperature at which a composition begins the transition from a glassy state to a rubbery state.

As used herein, the term "*Penicillium bilaiae*" is intended to include all iterations of the species name, such as "*Penicillium bilaji*" and "*Penicillium bilaii.*"

As used herein, the term "pest" includes any organism or virus that negatively affects a plant, including, but not limited to, organisms and viruses that spread disease, damage host plants and/or compete for soil nutrients. The term "pest" encompasses organisms and viruses that are known to associate with plants and to cause a detrimental effect on the plant's health and/or vigor. Plant pests include, but are not limited to, arachnids (e.g., mites, ticks, spiders, etc.), bacteria, fungi, gastropods (e.g., slugs, snails, etc.), invasive plants (e.g., weeds), insects (e.g., white flies, *thrips*, weevils, etc.), *nematodes* (e.g., root-knot nematode, soybean cyst nematode, etc.), rodents and viruses (e.g., tobacco mosaic virus (TMV), tomato spotted wilt virus (TSWV), cauliflower mosaic virus (CaMV), etc.).

As used herein, the terms "pesticide" and "pesticidal" refer to agents or combinations of agents the application of which is toxic to a pest (i.e., kills a pest, inhibits the growth of a pest and/or inhibits the reproduction of a pest). Non-limiting examples of pesticides include acaricides, fungicides, herbicides, insecticides, and nematicides, etc.

As used herein, the term "phosphate-solubilizing microorganism" refers to a microorganism capable of converting insoluble phosphate into a soluble form of phosphate.

As used herein, the term "plant" includes all plant populations, including, but not limited to, agricultural, horticultural and silvicultural plants. The term "plant" encompasses plants obtained by conventional plant breeding and optimization methods (e.g., marker-assisted selection) and plants obtained by genetic engineering, including cultivars protectable and not protectable by plant breeders' rights.

As used herein, the term "plant cell" refers to a cell of an intact plant, a cell taken from a plant, or a cell derived from a cell taken from a plant. Thus, the term "plant cell" includes cells within seeds, suspension cultures, embryos, meristematic regions, callus tissue, leaves, shoots, gametophytes, sporophytes, pollen and microspores.

As used herein, the term "plant part" refers to any part of a plant, including cells and tissues derived from plants. Thus, the term "plant part" may refer to any of plant components or organs (e.g., leaves, stems, roots, etc.), plant tissues, plant cells and seeds. Examples of plant parts, include, but are not limited to, anthers, embryos, flowers, fruits, fruiting bodies, leaves, ovules, pollen, rhizomes, roots, seeds, shoots, stems and tubers, as well as scions, rootstocks, protoplasts, calli and the like.

As used herein, the term "plant propagation material" refers to a plant part from which a whole plant can be generated. Examples of plant propagation materials include, but are not limited to, cuttings (e.g., leaves, stems), rhizomes, seeds, tubers and cells/tissues that can be cultured into a whole plant.

As used herein, the term "protectant" refers to an agent or combination of agents the application of which enhances the survival and/or stability of a microorganism in an inoculant composition.

As used herein, the term "rubbery state" refers to an amorphous, visoelastic liquid.

As used herein, the terms "spore" and "microbial spore" refer to a microorganism in its dormant, protected state.

As used herein with respect to inoculant compositions, the term "stable" refers to an inoculant composition in which microorganisms exhibit enhanced stability and/or enhanced survival. In general, an inoculant composition may be labeled "stable" if it improves the survival rate and/or at least one microbial stability characteristic of at least one microorganism contained therein.

As used herein with respect to microbial spores, the term "survival rate" refers to the percentage of microbial spores that are viable (i.e., capable of propagating on or in a substrate (e.g., on a seed and/or in a soil) when conditions (e.g., temperature, moisture, nutrient availability, pH, etc.) are favorable for microbial growth) at a given period of time.

While certain aspects of the present disclosure will hereinafter be described with reference to embodiments thereof, it will be understood by those of ordinary skill in the art that various changes in form and details may be made therein without departing from the spirit and scope of the present disclosure as defined by the claims.

All publications, patent applications, patents and other references mentioned herein are incorporated by reference in their entirety, except insofar as they contradict any disclosure expressly set forth herein.

The present disclosure provides stable inoculant compositions and methods for enhancing the stability and/or survival of microbial spores.

The present disclosure provides aqueous inoculant compositions comprising, consisting essentially of, or consisting of one or more microbial spores and an aqueous carrier. In some embodiments, the aqueous inoculant composition comprises, consists essentially of or consists of microbial spores, one or more protectants, one or more dispersants, one or more aqueous additives and a non-aqueous carrier.

Inoculant compositions of the present disclosure may comprise any suitable spores(s), including, but not limited to, the spores of agriculturally beneficial microorganisms such as diazotrophs, phosphate-solubilizing microorganisms and biopesticides.

In some embodiments, inoculant compositions of the present disclosure comprise spores from one or more bacteria (e.g., one or rmore Gram-negative bacteria and/or one or more Gram-positive bacteria). Non-limiting examples of bacterial spores that may be useful in compositions of the present disclosure include spores of *Bacillus amyloliquefaciens* D747, *Bacillus amyloliquefaciens* NRRL B-50349, *Bacillus amyloliquefaciens* TJ1000, *Bacillus amyloliquefaciens* FZB24, *Bacillus amyloliquefaciens* FZB42, *Bacillus amyloliquefaciens* IN937a, *Bacillus amyloliquefaciens* IT-45, *Bacillus amyloliquefaciens* TJ1000, *Bacillus amyloliquefaciens* MBI600, *Bacillus amyloliquefaciens* BS27 (deposited as NRRL B-5015), *Bacillus amyloliquefaciens* BS2084 (deposited as NRRL B-50013), *Bacillus amyloliquefaciens* 15AP4 (deposited as ATCC PTA-6507), *Bacillus amyloliquefaciens* 3AP4 (deposited as ATCC PTA-6506), *Bacillus amyloliquefaciens* LSSA01 (deposited as NRRL B-50104), *Bacillus amyloliquefaciens* ABP278 (deposited as NRRL B-50634), *Bacillus amyloliquefaciens* 1013 (deposited as NRRL B-50509), *Bacillus amyloliquefaciens* 918 (deposited as NRRL B-50508), *Bacillus amyloliquefaciens* 22CP1 (deposited as ATCC PTA-6508) and *Bacillus amyloliquefaciens* BS18 (deposited as NRRL B-50633), *Bacillus cereus* I-1562, *Bacillus firmus* I-1582, *Bacillus lichenformis* BA842 (deposited as NRRL B-50516), *Bacillus lichenformis* BL21 (deposited as NRRL B-50134), *Bacillus mycoides* NRRL B-21664, *Bacillus pumilus* NRRL B-21662, *Bacillus pumilus* NRRL B-30087, *Bacillus pumilus* ATCC 55608, *Bacillus pumilus* ATCC 55609, *Bacillus pumilus* GB34, *Bacillus pumilus* KFP9F, *Bacillus pumilus* QST 2808, *Bacillus subtilis* ATCC 55078, *Bacillus subtilis* ATCC 55079, *Bacillus subtilis* MBI600, *Bacillus subtilis* NRRL B-21661, *Bacillus subtilis* NRRL B-21665, *Bacillus subtilis* CX-9060, *Bacillus subtilis* GB03, *Bacillus subtilis* GB07, *Bacillus subtilis* QST-713, *Bacillus subtilis* FZB24, *Bacillus subtilis* D747, *Bacillus subtilis* 3BP5 (deposited as NRRL B-50510), *Bacillus thuringiensis* ATCC 13367, *Bacillus thuringiensis* GC-91, *Bacillus thuringiensis* NRRL B-21619, *Bacillus thuringiensis* ABTS-1857, *Bacillus thuringiensis* SAN 401 I, *Bacillus thuringiensis* ABG-6305, *Bacillus thuringiensis* ABG-6346, *Bacillus thuringiensis* AM65-52, *Bacillus thuringiensis* SA-12, *Bacillus thuringiensis* SB4, *Bacillus thuringiensis* ABTS-351, *Bacillus thuringiensis* HD-1, *Bacillus thuringiensis* EG 2348, *Bacillus thuringiensis* EG 7826, *Bacillus thuringiensis* EG 7841, *Bacillus thuringiensis* DSM 2803, *Bacillus thuringiensis* NB-125, *Bacillus thuringiensis* NB-176 and combinations thereof, as well as spores of microorganisms having at least at least 75%, 80%, 85%, 90%, 95%, 96%, 97%, 98%, 99% or more identical to any of the aforementioned strains on the basis of 16S rDNA sequence identity.

In some embodiments, inoculant compositions of the present disclosure comprise one or more fungal spores. Non-limiting examples of fungal spores that may be useful in compositions of the present disclosure include spores of *Gliocladium virens* ATCC 52045, *Gliocladium virens* GL-21, *Glomus intraradices* RTI-801, *Metarhizium anisopliae* F52, *Penicillium bilaiae* (formerly known as *P. bilaiae* and *P. bilaji*) ATCC 18309, *Penicillium bilaiae*

ATCC 20851, *Penicillium bilaiae* ATCC 22348, *Penicillium bilaiae* NRRL 50162, *Penicillium bilaiae* NRRL 50169, *Penicillium bilaiae* NRRL 50776, *Penicillium bilaiae* NRRL 50777, *Penicillium bilaiae* NRRL 50778, *Penicillium bilaiae* NRRL 50777, *Penicillium bilaiae* NRRL 50778, *Penicillium bilaiae* NRRL 50779, *Penicillium bilaiae* NRRL 50780, *Penicillium bilaiae* NRRL 50781, *Penicillium bilaiae* NRRL 50782, *Penicillium bilaiae* NRRL 50783, *Penicillium bilaiae* NRRL 50784, *Penicillium bilaiae* NRRL 50785, *Penicillium bilaiae* NRRL 50786, *Penicillium bilaiae* NRRL 50787, *Penicillium bilaiae* NRRL 50788, *Penicillium bilaiae* RS7B-SD1, *Penicillium brevicompactum* AgRF18, *Penicillium canescens* ATCC 10419, *Penicillium expansum* ATCC 24692, *Penicillium expansum* YT02, *Penicillium fellatanum* ATCC 48694, *Penicillium gaestrivorus* NRRL 50170, *Penicillium glabrum* DAOM 239074, *Penicillium glabrum* CBS 229.28, *Penicillium janthinellum* ATCC 10455, *Penicillium lanosocoeruleum* ATCC 48919, *Penicillium radicum* ATCC 201836, *Penicillium radicum* FRR 4717, *Penicillium radicum* FRR 4719, *Penicillium radicum* N93/47267, *Penicillium raistrickii* ATCC 10490, *Trichoderma asperellum* SKT-1, *Trichoderma asperellum* ICC 012, *Trichoderma atroviride* LC52, *Trichoderma atroviride* CNCM 1-1237, *Trichoderma fertile* JM41R, *Trichoderma gamsii* ICC 080, *Trichoderma hamatum* ATCC 52198, *Trichoderma harzianum* ATCC 52445, *Trichoderma harzianum* KRL-AG2, *Trichoderma harzianum* T-22, *Trichoderma harzianum* TH-35, *Trichoderma harzianum* T-39, *Trichoderma harzianum* ICC012, *Trichoderma reesi* ATCC 28217, *Trichoderma virens* ATCC 57678, *Trichoderma virens* G1-3, *Trichoderma virens* GL-21, *Trichoderma virens* G-41, *Trichoderma viridae* ATCC 52440, *Trichoderma viridae* ICC080, *Trichoderma viridae* TV1 and combinations thereof, as well as spores of microorganisms having at least at least 75%, 80%, 85%, 90%, 95%, 96%, 97%, 98%, 99% or more identical to any of the aforementioned strains on the basis of internal transcribed spacer (ITS) and/or cytochrome c oxidase (CO1) sequence identity.

In some embodiments, inoculant compositions of the present disclosure comprise spores from one or more mycorrhizal fungi (e.g., one or more endomycorrhizal fungi and/or one or more ectomycorrhizal fungi). Non-limiting examples of mycorrhizal spores that may be useful in compositions of the present disclosure includespores of mycorrhizal strains such as *Gigaspora margarita*, *Glomus aggregatum*, *Glomus brasilianum*, *Glomus clarum*, *Glomus deserticola*, *Glomus etunicatum*, *Glomus intraradices*, *Glomus monosporum*, *Glomus mosseae*, *Laccaria bicolor*, *Laccaria laccata*, *Paraglomus brazilianum*, *Pisolithus tinctorius*, *Rhizopogon amylopogon*, *Rhizopogon fulvigleba*, *Rhizopogon luteolus*, *Rhizopogon villosuli*, *Scleroderma cepa* and *Scleroderma citrinum* and combinations thereof.

In some embodiments, inoculant compositions of the present disclosure comprise spores from one or more diazotrophs.

In some embodiments, inoculant compositions of the present disclosure comprise spores from one or more phosphate-solubilizing microorganisms.

In some embodiments, inoculant compositions of the present disclosure comprise spores from one or more biofungicides, bioherbicides, bioinsectides and/or bionematicides. See generally BURGES, FORMULATION OF MICROBIAL BIOPESTICIDES: BENEFICIAL MICRO-ORGANISMS, NEMATODES AND SEED TREAT-MENTS (Springer Science & Business Media) (2012); HALL & MENN, BIOPESTICIDES: USE AND DELIV-ERY (Humana Press) (1998); McCoy, et al., Entomogenous fungi, in CRC HANDBOOK OF NATURAL PESTICIDES. MICROBIAL PESTICIDES, PART A. ENTOMOGENOUS PROTOZOA AND FUNGI (C. M. Inoffo, ed.), Vol. 5:151-236 (1988); SAMSON, et al., ATLAS OF ENTO-MOPATHOGENIC FUNGI (Springer-Verlag, Berlin) (1988); deFaria and Wraight, *Mycoinsecticides and Mycoacaricides: A comprehensive list with worldwide coverage and international classification of formulation types*, BIOL. CONTROL (2007), doi: 10.1016/j.biocontrol.2007.08.001; and WO 2016/096821. Non-limiting examples of biopesticidal strains that may be useful in compositions of the present disclosure include *Ampelomyces quisqualis* AQ 10® (Intrachem Bio GmbH & Co. KG, Germany), *Aspergillus flavus* AFLA-GUARD® (Syngenta Crop Protection, Inc., CH), *Aureobasidium pullulans* BOTECTOR® (bio-ferm GmbH, Germany), *Bacillus* AQ175 (ATCC 55608), *Bacillus* AQ177 (ATCC 55609), *Bacillus amyloliquefaciens* FZB24, *Bacillus amyloliquefaciens* FZB42, *Bacillus amyloliquefaciens* NRRL B-50349, *Bacillus amyloliquefaciens* TJ1000 (also known as 1BE, isolate ATCC BAA-390), *Bacillus firmus* I-1582, *Bacillus mycoides* AQ726 (NRRL B-21664); *Bacillus pumilus* AQ717 (NRRL B-21662), *Bacillus pumilus* NRRL B-30087, *Bacillus subtilis* AQ713 (NRRL B-21661), *Bacillus subtilis* AQ743 (NRRL B-21665), *Bacillus subtilis* ATCC 55078, *Bacillus subtilis* ATCC 55079, *Bacillus thuringiensis* AQ52 (NRRL B-21619), *Beauveria bassiana* ATCC-74040, *Beauveria bassiana* ATCC-74250, *Burkholderia* sp. A396 sp. nov. rinojensis, NRRL B-50319, *Candida oleophila* I-182 (e.g., ASPIRE®, Ecogen Inc., USA), *Candida saitoana*, *Chromobacterium subtsugae* NRRL B-30655, *Chromobacterium vaccinii* NRRL B-50880, *Clonostachys rosea* f. *catenulata* (also referred to as *Gliocladium catenulatum*) J1446 (PRESTOP®, Verdera, Finland), *Coniothyrium minitans* CONTANS® (Prophyta, Germany), *Cryphonectria parasitica* (CNICM, France), *Cryptococcus albidus* YIELD PLUS® (Anchor Bio-Technologies, South Africa), *Flavobacterium* H492, NRRL B-50584, *Fusarium oxysporum* BIOFOX® (from S.I.A.P.A., Italy) and FUSACLEAN® (Natural Plant Protection, France), *Gliocladium virens* GL-21 (SOIL-GARD®, Certis LLC, USA), *Metarhizium anisopliae* F52 (also known as *Metarhizium anisopliae* strain 52, *Metarhizium anisopliae* strain 7, *Metarhizium anisopliae* strain 43 and *Metarhizium anisopliae* BIO-1020, TAE-001; deposited as DSM 3884, DSM 3885, ATCC 90448, SD170 and ARSEF 7711), *Metschnikowia fructicola* SHEMER® (Agrogreen, Israel), *Microdochium dimerum* ANTIBOT® (Agrauxine, France), *Muscodor albus* NRRL 30547, *Muscodor roseus* NRRL 30548, *Paecilomyces fumosoroseus* FE991, *Phlebiopsis gigantea* ROTSOP® (Verdera, Finland), *Pseudozyma flocculosa* SPORODEX® (Plant Products Co. Ltd., Canada), *Pythium oligandrum* DV74 (POLYVERSUM®, Remeslo SSRO, Biopreparaty, Czech Rep.), *Reynoutria sachlinensis* (e.g., REGALIA®, Marrone BioInnovations, USA), *Streptomyces* NRRL B-30145, *Streptomyces* M1064, *Streptomyces galbus* NRRL 30232, *Streptomyces lydicus* WYEC 108 (ATCC 55445), *Streptomyces violaceusniger* YCED 9 (ATCC 55660), *Streptomyces* WYE 53 (ATCC 55750), *Talaromyces flavus* V117b (PROTUS®, Prophyta, Germany), *Trichoderma asperellum* SKT-1 (ECO-HOPE®, Kumiai Chemical Industry Co., Ltd., Japan), *Trichoderma atroviride* LC52 (SENTINEL®, Agrimm Technologies Ltd, NZ), *Trichoderma harzianum* T-22 (PLANTSHIELD®, BioWorks Inc., USA), *Trichoderma harzianum* TH-35 (ROOT PRO®, from Mycontrol Ltd., Israel), *Trichoderma harzianum* T-39 (TRICHODEX®, Mycontrol Ltd., Israel; *TRICHODERMA* 2000®, Makhteshim Ltd., Israel), *Tricho-*

*derma harzianum* ICC012 and *Trichoderma viride* TRICHOPEL (Agrimm Technologies Ltd, NZ), *Trichoderma harzianum* ICC012 and *Trichoderma viride* ICC080 (REMEDIER® WP, Isagro Ricerca, Italy), *Trichoderma polysporum* and *Trichoderma harzianum* (BINAB®, BINAB Bio-Innovation AB, Sweden), *Trichoderma stromaticum* TRICOVAB® (C.E.P.L.A.C., Brazil), *Trichoderma virens* GL-3 (ATCC 58678), *Trichoderma viride* TRIECO® (Ecosense Labs. (India) Pvt. Ltd., India, BIO-CURE® F, T. Stanes & Co. Ltd., India), *Trichoderma viride* TV1 (Agribiotec srl, Italy), *Trichoderma viride* ICC080, *Uloclodium oudemansii* HRU3 (BOTRY-ZEN®, Botry-Zen Ltd, NZ) and combinations thereof.

In some embodiments, inoculant compositions of the present disclosure comprise spores from one or more modified microbial strains.

Microbial spores may be incorporated into inoculant compositions of the present disclosure in any suitable amount(s)/concentration(s).

In some embodiments, microbial spores comprise about 0.1 to about 50% (by weight) of the inoculant composition. For example, inoculant compositions of the present disclosure may comprise about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50% or more (by weight) of one or more microbial spores. In some embodiments, the microbial spore amount/concentration is about 1, 2, 3, 4 or 5 to about 5, 6, 7, 8, 9, 10, 11, 12, 13, 14, 15, 16, 17, 18, 19, 20, 21, 22, 23, 24 or 25% (by weight) of the inoculant composition.

In some embodiments, microbial spores are present in an amount ranging from about $1 \times 10^1$ to about $1 \times 10^{15}$ colony-forming units (cfu) per gram and/or milliliter of inoculant composition. For example, inoculant compositions of the present disclosure may comprise about $1 \times 10^1$, $1 \times 10^2$, $1 \times 10^3$, $1 \times 10^4$, $1 \times 10^5$, $1 \times 10^6$, $1 \times 10^7$, $1 \times 10^1$, $1 \times 10^9$, $1 \times 10^{10}$, $1 \times 10^{11}$, $1 \times 10^{12}$ or more microbial spores per gram and/or milliliter of inoculant composition (e.g., about $1 \times 10^4$ to about $1 \times 10^9$ *Bacillus amyloliquefaciens* TJ1000 (also known as 1BE, isolate ATCC BAA-390), *Metarhizium anisopliae* F52, *Penicillium bilaiae* ATCC 20851, *Penicillium bilaiae* RS7B-SD1 and/or *Trichoderma virens* G1-3 spores per gram/milliliter).

In some embodiments, the microbial spores are present in an amount/concentration effective for fixing atmospheric nitrogen, solubilizing phosphate, controlling one or more phytopathogenic pests, enhancing plant growth, enhancing plant stress tolerance and/or enhancing plant yield when the inoculant composition is introduced into a plant growth medium (e.g., a soil).

In some embodiments, the microbial spores are present in an amount/concentration effective for fixing atmospheric nitrogen, solubilizing phosphate, controlling one or more phytopathogenic pests, enhancing plant growth, enhancing plant stress tolerance and/or enhancing plant yield when the inoculant composition is applied to a plant or plant part.

Microbial spores may be produced by any suitable method(s), including, but not limited to, liquid fermentation and solid state fermentation. See, e.g., Cunningham et al., CAN. J. BOT. 68:2270 (1990); Friesen et al., APPL. MICROBIOL. BIOTECH. 68:397 (2005).

Microbial spores may be harvested and/or concentrated using any suitable method(s), including, but not limited to, centrifugation (e.g., density gradient centrifugation, disc stack centrifugation, tubular bowl centrifugation), coagulation, decanting, felt bed collection, filtration (e.g., drum filtration, sieving, ultrafiltration), flocculation, impaction and trapping (e.g., cyclone spore trapping, liquid impingement).

Although the primary foci of the present disclosure are compositions and methods for enhancing the stability and/or survival of microbial spores, it is to be understood that inoculant compositions of the present disclosure may comprise one or more microorganisms (e.g., diazotrophs, phosphate-solubilizing microorganisms and/or biopesticides) in a vegetative state.

Vegetative cells may be incorporated into inoculant compositions of the present disclosure in any suitable amount(s)/concentration(s). In some embodiments, inoculant compositions of the present disclosure are devoid of vegetative cells.

In some embodiments, vegetative cells comprise about 0.1 to about 50% (by weight) of the inoculant composition. For example, inoculant compositions of the present disclosure may comprise about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50% or more (by weight) of one or more vegetative cells.

In some embodiments, vegetative cells are present in an amount ranging from about $1 \times 10^1$ to about $1 \times 10^{12}$ colony-forming units (cfu) per gram and/or milliliter of inoculant composition. For example, inoculant compositions of the present disclosure may comprise about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ or more cfu of agriculturally beneficial microorganisms per gram and/or milliliter of inoculant composition.

In some embodiments, the vegetative cells are present in an amount/concentration effective for fixing atmospheric nitrogen, solubilizing phosphate, controlling one or more phytopathogenic pests, enhancing plant growth, enhancing plant stress tolerance and/or enhancing plant yield when the inoculant composition is introduced into a plant growth medium (e.g., a soil).

In some embodiments, the vegetative cells are present in an amount/concentration effective for fixing atmospheric nitrogen, solubilizing phosphate, controlling one or more phytopathogenic pests, enhancing plant growth, enhancing plant stress tolerance and/or enhancing plant yield when the inoculant composition is applied to a plant or plant part.

Inoculant compositions of the present disclosure may comprise any suitable carrier(s), including, but not limited to, foliar-compatible carriers, seed-compatible carriers and soil-compatible carriers. In some embodiments, the inoculant composition comprises one or more aqueous carriers. In some embodiments, the inoculant composition comprises one or more non-aqueous carriers. Selection of appropriate carrier materials will depend on the intended application(s) and the microorganism(s) present in the inoculant composition.

In some embodiments, the carrier material(s) will be selected to provide an inoculant composition in the form of a liquid, gel, slurry, or solid.

In some embodiments, inoculant compositions of the present disclosure comprise one or more liquid and/or gel carriers. Non-limiting examples of liquid/gel carriers that may be useful in compositions of the present disclosure include oils (e.g., mineral oil, olive oil, peanut oil, soybean oil, sunflower oil), polyethylene glycols (e.g., PEG 200, PEG 300, PEG 400, etc.), propylene glycols (e.g., PPG-9, PPG-10, PPG-17, PPG-20, PPG-26, etc.), ethoxylated alcohols (e.g., TOMADOL® (Air Products and Chemicals, Inc., Allentown, PA), TAMOL™ dispersants (The Dow Chemical Company, Midland, MI), TERGITOL™ 15-S surfactants such as TERGITOL™15-S-9 (The Dow Chemical Company, Midland, MI), etc.), polysorbates (e.g. polysorbate 20, polysorbate 40, polysorbate 60, polysorbate 80, etc.), silicones (siloxanes, trisiloxanes, etc.) and combinations thereof.

In some embodiments, inoculant compositions of the present disclosure comprise one or more non-aqueous solvents.

In some embodiments, inoculant compositions of the present disclosure comprise one or more aqueous solvents.

In some embodiments, inoculant compositions of the present disclosure comprise one or more inorganic solvents, such as decane, dodecane, hexylether and nonane, and/or one or more organic solvents, such as acetone, dichloromethane, ethanol, hexane, methanol, propan-2-ol and trichloroethylene.

Additional examples of solvents that may be included in inoculant compositions of the present disclosure may be found in BURGES, FORMULATION OF MICROBIAL BIOPESTICIDES: BENEFICIAL MICROORGANISMS, NEMATODES AND SEED TREATMENTS (Springer Science & Business Media) (2012); Inoue & Horikoshi, J. FERMENTATION BIOENG.71(3):194 (1991).

In some embodiments, inoculant compositions of the present disclosure comprise one or more solid carriers. For example, in some embodiments, inoculant compositions of the present disclosure comprise one or more powders (e.g., wettable powders) and/or granuales. Non-limiting examples of solid carriers that may be useful in compositions of the present disclosure include peat-based powders and granuales, freeze-dried powders, spray-dried powders and combinations thereof. Additional examples of solid carriers that may be included in inoculant compositions of the present disclosure may be found in BURGES, FORMULATION OF MICROBIAL BIOPESTICIDES: BENEFICIAL MICROORGANISMS, NEMATODES AND SEED TREATMENTS (Springer Science & Business Media) (2012).

Carriers incorporated into inoculant compostions of the present disclosure may comprise a growth medium suitable for culturing one or more of the microorganisms in the inoculant composition. For example, in some embodiments, inoculant compositions of the present disclosure comprise Czapek-Dox medium, glycerol yeast extract, mannitol yeast extract, potato dextrose broth and/or YEM media.

Carriers may constitute any suitable portion of the inoculant composition. In some embodiments, an aqueous carrier comprises about 1 to about 99% (by weight) of the inoculant composition. For example, an aqueous carrier may constitute about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, 99.5% or more (by weight) of the inoculant composition. In some embodiments, a non-aqueous carrier comprises about 1 to about 99% (by weight) of the inoculant composition. For example, a non-aqueous carrier may constitute about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, 99.5% or more (by weight) of the inoculant composition. In some embodiments, the carrier amount/concentration is about 50 to about 99%, about 55% to about 95%, about 60% to about 95%, about 65% to about 90%, about 70 to about 90%, about 75 to about 90%, about 80 to about 90% or about 80 to about 85% (by weight) of the inoculant composition. In some embodiments, inoculant compositions of the present disclosure comprise one or more commercial carriers used in accordance with the manufacturer's recommended amounts/concentrations.

Inoculant compositions of the present disclosure may comprise any suitable protectants(s), including, but not limited to, monosaccharides, disaccharides, oligosaccharides, maltodextrins, sugar alcohols, humic acids, malt extracts, peat extracts, skim milk extracts, betaines, prolines, sarcosines, peptones, oxidation control components, hygroscopic polymers and UV protectants.

In some embodiments, inoculant compositions of the present disclosure comprise one or more monosaccharides (e.g., allose, altrose, arabinose, fructose, galactose, glucose, gulose, iodose, lyxose, mannose, ribose, talose, threose and/or xylose). In some embodiments, one or more of allose, altrose, arabinose, fructose, galactose, glucose, gulose, iodose, lyxose, mannose, ribose, talose, threose and xylose is/are excluded from inoculant compositions of the present disclosure.

In some embodiments, inoculant compositions of the present disclosure comprise one or more disaccharides (e.g., cellobiose, chitobiose, gentiobiose, gentiobiulose, isomaltose, kojibiose, lactose, lactulose, laminaribiose, maltose (e.g., maltose monohydrate, anhydrous maltose), maltulose, mannobiose, melibiose, melibiulose, nigerose, palatinose, rutinose, rutinulose, sophorose, sucrose, trehalose, turanose and/or xylobiose). In some embodiments, one or more of cellobiose, chitobiose, gentiobiose, gentiobiulose, isomaltose, kojibiose, lactose, lactulose, laminaribiose, maltose (e.g., maltose monohydrate, anhydrous maltose), maltulose, mannobiose, melibiose, melibiulose, nigerose, palatinose, rutinose, rutinulose, sophorose, sucrose, trehalose (e.g., trehalose dihydrate, anhydrous trehalose), turanose and xylobiose is/are excluded from inoculant compositions of the present disclosure.

In some embodiments, inoculant compositions of the present disclosure comprise one or more oligosaccharides (e.g., fructo-oligosaccharides, galacto-oligosaccharides, mannon-oligosaccharides and/or raffinose). In some embodiments, inoculant compositions of the present disclosure comprise raffinose. In some embodiments, inoculant compositions of the present disclosure do not comprise raffinose.

In some embodiments, inoculant compositions of the present disclosure comprise one or more maltodextrins having a dextrose equivalent value (DEV) of about 3, 4, 5, 6, 7, 8, 9, 10, 11, 12, 13, 14, 15, 16, 17, 18, 19, 20, 21, 22, 23, 24, or 25. In some embodiments, inoculant compositions of the present disclosure comprise one or more maltodextrins having a DEV of about 5 to about 6, 7, 8, 9, 10, 11, 12, 14, 15, 16, 17, 18, 19, 20, 21, 22, 23, 24, or 25, about 10 to about 11, 12, 14, 15, 16, 17, 18, 19, 20, 21, 22, 23, 24, or 25, or about 15 to about 16, 17, 18, 19, 20, 21, 22, 23, 24, or 25. In some embodiments, inoculant compositions of the present disclosure comprise a combination of maltodextrins having a DEV of about 5 to about 6, 7, 8, 9, 10, 11, 12, 14, 15, 16, 17, 18, 19, 20, 21, 22, 23, 24, or 25, about 10 to about 11, 12, 14, 15, 16, 17, 18, 19, 20, 21, 22, 23, 24, or 25, or about 15 to about 16, 17, 18, 19, 20, 21, 22, 23, 24, or 25. In some embodiments, inoculant compositions of the present disclosure comprise one or more maltodextrins having a DEV of about 10 to about 25 (e.g., one or more maltodextrins having a DEV of about 15 to about 20). In some embodiments, inoculant compositions of the present disclosure comprise a combination of maltodextrins having a DEV of about 10 to about 25 (e.g., a combination of maltodextrins having a DEV of about 15 to about 20). Non-limiting examples of maltodextrins that may be useful in compositions of the present disclosure include MALTRIN® M040 (DEV=5; molecular weight=3600; Grain Processing Corporation, Muscatine, IA), MALTRIN® M100 (DEV=10; molecular weight=1800; Grain Processing Corporation, Muscatine, IA), MALTRIN® M150 (DEV=15; molecular weight=1200; Grain Processing Corporation, Muscatine, IA), MALTRIN® M180 (DEV=18; molecular weight=1050; Grain Processing Corporation, Muscatine, IA), MALTRIN® M200 (DEV=20; molecular weight=900; Grain Processing Corporation, Muscatine, IA), MALTRIN® M250 (DEV=25; molecular weight=720; Grain Processing Corporation, Muscatine, IA); MALTRIN QD® M580 (DEV=16.5-19.9; Grain Processing Corporation, Muscatine, IA); MALTRIN QD® M585 (DEV=15.0-19.9; Grain Processing Corporation, Muscatine, IA); MALTRIN QD® M600 (DEV=20.0-23.0; Grain Processing Corporation, Muscatine, IA); GLOBE® Plus 15 DE (Ingredion Inc., Westchester, IL); and combinations thereof. In some embodiments, the maltodextrin (or combination of maltodextrins) has a DEV of 15 to 20.

In some embodiments, inoculant compositions of the present disclosure comprise one or more sugar alcohols (e.g., arabitol, erythritol, fucitol, galactitol, glycerol, iditol, inositol, isomalt, lactitol, maltitol, maltotetraitol, maltotriitol, mannitol, polyglycitol, ribitol, sorbitol, threitol, volemitol and/or xylitol In some embodiments, one or more of arabitol, erythritol, fucitol, galactitol, glycerol, iditol, inositol, isomalt, lactitol, maltitol, maltotetraitol, maltotriitol, mannitol, polyglycitol, ribitol, sorbitol, threitol, volemitol and xylitol is/are excluded from inoculant compositions of the present disclosure.

In some embodiments, inoculant compositions of the present disclosure comprise one or more humic acids (e.g., one or more leonardite humic acids, lignite humic acids, peat humic acids and water-extracted humic acids). In some embodiments, the inoculant composition comprises ammonium humate, boron humate, potassium humate and/or sodium humate. In some embodiments, one or more of ammonium humate, boron humate, potassium humate and sodium humate is/are excluded from inoculant compositions of the present disclosure. Nonlimiting examples of humic acids that may be useful in embodiments of the present disclosure include MDL Number MFCD00147177 (CAS Number 1415-93-6), MDL Number MFCD00135560 (CAS Number 68131-04-4), MDL Number MFCS22495372 (CAS Number 68514-28-3), CAS Number 93924-35-7 and CAS Number 308067-45-0.

In some embodiments, inoculant compositions of the present disclosure comprise one or more malt extracts, peat extracts, and/or skim milk extracts.

In some embodiments, inoculant compositions of the present disclosure comprise one or more betaines (e.g., trimethylglycine).

In some embodiments, inoculant compositions of the present disclosure comprise one or more peptones (e.g., one or more bacterial peptones, meat peptones, milk peptones, vegetable peptones and/or yeast peptones).

In some embodiments, inoculant compositions of the present disclosure comprise one or more oxidation control components.

Inoculant compositions of the present disclosure may comprise any suitable oxidation control component(s), including, but not limited to, antioxidants and/or oxygen scavengers. In some embodiments, the oxidation control component is/comprises ascorbic acid and/or glutathione.

In some embodiments, inoculant compositions comprise one or more antioxidants. For example, in some embodiments, inoculant compositions of the present disclosure comprise ascorbic acid, ascorbyl palmitate, ascorbyl stearate, calcium ascorbate, carotenoids, lipoic acid, phenolic compounds (e.g., flavonoids, flavones, flavonols), potassium ascorbate, sodium ascorbate, thiols (e.g., glutathione, lipoic acid, N-acetyl cysteine), tocopherols, tocotrienols, ubiquinone and/or uric acid. Non-limiting examples of antioxidants that may be useful in compositions of the present disclosure include those that are soluble in the cell membrane (e.g., alpha tocopherol (vitamin E), ascorbyl palmitate), those that are soluble in alcohols (e.g., IRGANOX® antioxidants (BASF Schweiz AG, Basel, Switzerland)) and those that are soluble in water (e.g., ascorbic acid and isomers or ascorbic acid, sodium or potassium salts of ascorbic acid or isomers or ascorbic acid, glutathione, sodium or potassium salts of glutathione). In some embodiments, use of a membrane-soluble antioxidant necessitates the addition of one or more surfactants to adequately disperse the antioxidant within the inoculant composition.

In some embodiments, inoculant compositions comprise one or more naturally occurring or synthetic oxygen scavengers. For example, in some embodiments, inoculant compositions of the present disclosure comprise ascorbic acid, ascorbate salts, catechol and/or sodium hydrogen carbonate.

In some embodiments, inoculant compositions of the present disclosure comprise one or more hygroscopic polymers (e.g., one or more albumins, alginates, celluloses, gums (e.g., cellulose gum, guar gum, gum arabic, gum combretum, xantham gum), methyl celluloses, nylons, pectins, polyacrylic acids, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches). Non-limiting examples of hygroscopic polymers that may be useful in compositions of the present disclosure include AGRIMER™ polymers (e.g., 30, AL-10 LC, AL-22, AT/ATF, VA 3E, VA 31, VA 5E, VA 51, VA 6, VA 6E, VA 7E, VA 71, VEMA AN-216, VEMA AN-990, VEMA AN-1200, VEMA AN-1980, VEMA H-815MS; Ashland Specialty Ingredients, Wilmington, DE), EASYSPERSE™ polymers (Ashland Specialty Ingredients, Wilmington, DE); DISCO™ AG polymers (e.g., L-250, L-280, L-285, L-286, L-320, L-323, L-517, L-519, L-520, L800; Incotec Inc., Salinas, CA), KELZAN® polymers (Bri-Chem Supply Ltd., Calgary, Alberta, CA), SEEDWORX™ polymers (e.g., Bio 200; Aginnovation, LLC, Walnut Groove, CA), TABULOSE® gels (e.g., SC-580, SC-612, SC-613, SC-681; Blanver Farmoquimica, Boca Raton, FL), TICAXAN® xanthan powders (TIC Gums, White Marsh, MD) and combinations thereof. Additional examples of hygroscopic polymers that may be included in inoculant compositions of the present disclosure may be found in Pouci, et al. AM. J. AGRIC. BIOL. SCI. 3(1):299 (2008).

In some embodiments, inoculant compositions of the present disclosure comprise one or more UV protectants (e.g., one or more aromatic amino acids (e.g., tryptophan, tyrosine), carotenoids, cinnamates, lignosulfonates (e.g., calcium lignosulfonate, sodium lignosulfonate), melanins, mycosporines, polyphenols and/or salicylates). Non-limiting examples of UV protectants that may be useful in compositions of the present disclosure include Borregaard LignoTech™ lignosulfonates (e.g., Borresperse 3A, Borresperse CA, Borresperse NA, Marasperse AG, Norlig A, Norlig 1 ID, Ufoxane 3A, Ultrazine NA, Vanisperse CB;

Borregaard Lignotech, Sarpsborg, Norway) and combinations thereof. Additional examples of UV protectants that may be included in inoculanc compositions of the present disclosure may be found in BURGES, FORMULATION OF MICROBIAL BIOPESTICIDES: BENEFICIAL MICROORGANISMS, NEMATODES AND SEED TREATMENTS (Springer Science & Business Media) (2012).

Protectants may be incorporated into inoculant compositions of the present disclosure in any suitable form. In some embodiments, the protectant(s) included in inoculant compositions of the present disclosure is/are at least 70, 75, 80, 85, 90, 91, 92, 93, 94, 95, 96, 97, 98, 99, 99.5% or more pure.

Protectants may be incorporated into inoculant compositions of the present disclosure in any suitable amount(s)/concentration(s). The absolute value of the amount/concentration/dosage of protectant(s) that is/are sufficient to cause the desired effect(s) may be affected by factors such as the type, size and volume of material to which the compositon will be applied, the type(s) of microorganisms in the composition, the number of microorganisms in the composition, the stability of the microorganisms in the composition and storage conditions (e.g., temperature, relative humidity, duration). Those skilled in the art will understand how to select an effective amount/concentration/dosage using routine dose-response experiments. Guidance for the selection of appropriate amounts/concentrations can be found, for example, in International Patent Application Nos. PCT/US2016/050529 and PCT/US2016/050647 and U.S. Provisional Patent Application Nos. 62/296,798; 62/271,857; 62/347,773; 62/343,217; 62/296,784; 62/271,873; 62/347,785; 62/347,794; 62/347,805; 62/436,517 and 62/436,529.

In some embodiments, inoculant compositions of the present disclosure comprise one or more protectants in an amount/concentration of about 0.0005 to about 95% or more (by weight, based upon the total of the inoculant composition). For example, inoculant compositions of the present disclosure may comprise about 0.0005 to about 0.001, about 0.001 to about 1%, about 0.25 to about 5%, about 1 to about 10%, about 5 to about 25%, about 10% to about 30%, about 20% to about 40%, about 25% to about 50%, about 30 to about 60%, about 50 to about 75%, or about 75 to about 95% (by weight), optionally about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95%, of one or more monosaccharides, disaccharides, oligosaccharides, maltodextrins, sugar alcohols, humic acids, malt extracts, peat extracts, skim milk extracts, betaines, prolines, sarcosines, peptones, oxidation control components, hygroscopic polymers and/or UV protectants.

In some embodiments, inoculant compositions of the present disclosure comprise one or more protectants in an amount/concentration of about $1 \times 10^{-20}$ M to about $1 \times 10^{-1}$ M. For example, inoculant compositions of the present disclosure may comprise about $1 \times 10^{-15}$ M to about $1 \times 10^{-10}$ M, about $1 \times 10^{-14}$ M to about $1 \times 10^{-8}$ M, about $1 \times 10^{-14}$ M to about $1 \times 10^{-6}$ M, about $1 \times 10^{-12}$ M to about $1 \times 10^{-8}$ M, about $1 \times 10^{-12}$ M to about $1 \times 10^{-6}$ M, about $1 \times 10^{-10}$ M to about $1 \times 10^{-6}$ M, or about $1 \times 10^{-8}$ M to about $1 \times 10^{-2}$ M, optionally about $1 \times 10^{-20}$ M, $1 \times 10^{-19}$ M, $1 \times 10^{-18}$ M, $1 \times 10^{-17}$ M, $1 \times 10^{-16}$ M, $1 \times 10^{-15}$ M, $1 \times 10^{-14}$ M, $1 \times 10^{-13}$ M, $1 \times 10^{-12}$ M, $1 \times 10^{-1}$ M, $1 \times 10^{-10}$ M, $1 \times 10^{-9}$ M, $1 \times 10^{-8}$ M, $1 \times 10^{-7}$ M, $1 \times 10^{-6}$ M, $1 \times 10^{-5}$ M, $1 \times 10^{-4}$ M, $1 \times 10^{-3}$ M, $1 \times 10^{-2}$ M, $1 \times 10^{-1}$ M or more, of one or more monosaccharides, disaccharides, oligosaccharides, maltodextrins, sugar alcohols, humic acids, malt extracts, peat extracts, skim milk extracts, betaines, prolines, sarcosines, peptones, oxidation control components, hygroscopic polymers and/or UV protectants.

In some embodiments, inoculant compositions of the present disclosure comprise one or more monosaccharides in an amount/concentration of about 0.005 to about 50% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 5.5, 6, 6.5, 7, 7.5, 8, 8.5, 9, 10, 15, 20, 25% (by weight) of one or more monosaccharides (e.g., arabinose, fructose and/or glucose). In some embodiments, one or more monosaccharides is/are present in a concentration ranging from about $1\times10^{-20}$ M to about $1\times10^{-1}$ M. For example one or more monosaccharides may be included at a concentration of about/at least/less than $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M.

In some embodiments, inoculant compositions of the present disclosure comprise one or more disaccharides in an amount/concentration of about 0.005 to about 50% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 5.5, 6, 6.5, 7, 7.5, 8, 8.5, 9, 10, 15, 20, 25% (by weight) of one or more disaccharides (e.g., maltose, sucrose and/or trehalose). In some embodiments, one or more disaccharides is/are present in a concentration ranging from about $1\times10^{-20}$ M to about $1\times10^{-1}$ M. For example one or more disaccharides may be included at a concentration of about/at least/less than $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-1}$ M, $1\times10^{-10}$ M.

In some embodiments, inoculant compositions of the present disclosure comprise one or more sugar alcohols in an amount/concentration of about 0.005 to about 50% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 5.5, 6, 6.5, 7, 7.5, 8, 8.5, 9, 10, 15, 20, 25% (by weight) of one or more sugar alcohols (e.g., arabitol, mannitol, sorbitol and/or xylitol). In some embodiments, one or more sugar alcohols is/are present in a concentration ranging from about $1\times10^{-20}$ M to about $1\times10^{-1}$ M. For example one or more sugar alcohols may be included at a concentration of about/at least/less than $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M.

In some embodiments, inoculant compositions of the present disclosure comprise one or more maltodextrins in an amount/concentration of about 0.005 to about 95% or more (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 10, 15, 20, 25, 30, 35, 40, 45, 50, 55, 60, 65, 70, 75, 80, 85, 90, 95% of one or more maltodextrins (each and/or collectively) having a DEV value of about 15 to about 20. In some embodiments, the maltodextrin amount/concentration is 0.001 to about 1%, about 0.25 to about 5%, about 1 to about 10%, about 1 to about 65%, about 10% to about 30%, about 20% to about 40%, about 20% to about 50%, or about 30 to about 60% (by weight) of the inoculant composition. In some embodiments, one or more maltodextrins is/are present in a concentration ranging from about $1\times10^{-20}$ M to about $1\times10^{-1}$ M. For example one or more maltodextrins may be included at a concentration of about/at least/less than $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M.

In some embodiments, inoculant compositions of the present disclosure comprise one or more humic acids in an amount/concentration of about 0.005 to about 95% or more (by weight) of the inoculant composition. In some embodiments, the humic acid(s) (e.g., potassium humate and/or sodium humate) comprise(s) about 0.001 to about 1%, about 0.25 to about 5%, about 1 to about 10% (by weight) of the composition. For example, inoculant compositions of the present disclosure may comprise about/at least/less than 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% (by weight) of one or more humic acids (e.g., potassium humate and/or sodium humate). In some embodiments, one or more humic acids is/are present in a concentration ranging from about $1\times10^{-20}$ M to about $1\times10^{-1}$ M. For example one or more humic acids may be included at a concentration of about/at least/less than $1\times10^{-20}$ M, $1\times10^{-19}$ M, $1\times10^{-18}$ M, $1\times10^{-17}$ M, $1\times10^{-16}$ M, $1\times10^{-15}$, $1\times10^{-14}$ M, $1\times10^{-13}$ M, $1\times10^{-12}$ M, $1\times10^{-11}$ M, $1\times10^{-10}$ M. In some embodiments, inoculant compositions of the present disclosure comprise one or more malt extracts in an amount/concentration of about 0.005 to about 95% or more (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 10, 15, 20, 25% of one or more maltodextrins (each and/or collectively) having a DEV value of about 15 to about 20. In some embodiments, the malt extract amount/concentration is about 0.001 to about 1%, about 0.25 to about 5%, about 1 to about 10% (by weight) of the inoculant composition. In some embodiments, one or more malt extracts is/are present in a concentration ranging from about $1\times10^{-20}$ M to about $1\times10^{-1}$ M. For example one or more malt extracts may be included at a concentration of about/at least/less than $1\times10^{-20}$ M, $1\times10^{-19}$ M, $1\times10^{-18}$ M, $1\times10^{-17}$ M, $1\times10^{-16}$ M, $1\times10^{-15}$, $1\times10^{-14}$ M, $1\times10^{-13}$ M, $1\times10^{-12}$ M, $1\times10^{-11}$ M, $1\times10^{-10}$ M In some embodiments, inoculant compositions of the present disclosure comprise one or more peat extracts, skim milk extracts and/or peptones in an amount/concentration of about 0.005 to about 25% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of one or more peat extracts, skim milk extracts and/or peptones. In some embodiments, the peat extract, skim milk extract and/or peptone amount/concentration is about 0.5 to about 10% (by weight) of the inoculant composition.

In some embodiments, inoculant compositions of the present disclosure comprise one or more hygroscopic polymers in an amount/concentration of about 0.005 to about 25% (by weight) of the inoculant composition. In some embodiments, the hygroscopic polymer(s) comprise(s) about 0.5 to about 1, 1.5, 2, 2.5, 3, 3.5, 4, 4.5, 5, 5.5, 6, 6.5, 7, 7.5, 8, 8.5, 9, 9.5 or 10% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% (by weight) of one or more hygroscopic polymers. In some embodiments, the hygroscopic polymer amount/concentration is about 0.5 to about 10% (by weight) of the inoculant composition. In some embodiments, the hygroscopic polymer amount/concentration is about 0.5 to about 5% (by weight) of the inoculant composition. In some embodiments, inoculant compositions of the present disclosure comprise one or more commercial hygroscopic polymers used in accordance with the manufacturer's recommended amounts/concentrations.

In some embodiments, inoculant compositions of the present disclosure comprise one or more oxidation control components in an amount/concentration of about 0.0001 to about 5% or more (by weight) of the composition. For example, inoculant compositions of the present disclosure may comprise about/at least/less than 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% (by weight) or more oxidation control components. In some embodiments, the amount/concentration of oxidation control components is about 0.005 to about 2% (by weight) of the composition. In some embodiments, the oxidation control component(s) is/are present in a concentration ranging from about $1\times10^{-20}$ M to about $1\times10^{-1}$ M. For example, one or more oxidation control components may be added at a concentration of about/at least/less than $1\times10^{-20}$ M, $1\times10^{-19}$ M, $1\times10^{-18}$ M, $1\times10^{-17}$ M, $1\times10^{-16}$ M, $1\times10^{-15}$, $1\times10^{-14}$ M, $1\times10^{-13}$ M, $1\times10^{-12}$ M, $1\times10^{-11}$ M, $1\times10^{-10}$ M. In some embodiments, inoculant compositions of the present disclosure comprise one or more commercial antioxidants used in accordance with the manufacturer's recommended amounts/concentrations. In some embodiments, inoculant compositions of the present disclosure comprise one or more commercial oxygen scavengers used in accordance with the manufacturer's recommended amounts/concentrations.

Protectants may be incorporated into inoculant compositions of the present disclosure in any suitable ratio(s).

In some embodiments, inoculant compositions of the present disclosure comprise one or more maltodextrins and one or more mono-, di- and/or oligosaccharides in a ratio of about 1:99 to about 99:1 (by weight, based upon the respective weight percentages of the maltodextrin(s) and mono-, di- and/or oligosaccharide(s) in the inoculant composition). For example, inoculant compositions of the present disclosure may comprise one or more maltodextrins and one or more disaccharides (e.g. maltose, sucrose and/or trehalose) in a maltodextrin: disaccharide) ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5 or more, preferably about 50:50, 55:45, 60:40, 65:35, 70:30, 75:25, 80:20, 85:15, 90:10, 95:5 or more. Thus, in some embodiments, inoculant compositions of the present disclosure comprise one or more maltodextrins having a DEV of about 15 to about 20 and one or more mono-, di- and/or oligosaccharides in a ratio of about 45:55, 50:50, 55:45, 60:40, 65:35, 70:30, 75:25, 80:20, 85:15, 90:10, 95:5.

In some embodiments, inoculant compositions of the present disclosure comprise one or more maltodextrins and one or more sugar alcohols in a ratio of about 1:99 to about 99:1 (by weight, based upon the respective weight percentages of the maltodextrin(s) and sugar alcohol(s) in the inoculant composition). For example, inoculant compositions of the present disclosure may comprise one or more maltodextrins and one or more sugar alcohols (e.g. arabitol, mannitol. sorbitol and/or xylitol) in a maltodextrin: sugar alcohol ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5 or more, preferably about 50:50, 55:45, 60:40, 65:35, 70:30, 75:25, 80:20, 85:15, 90:10, 95:5 or more. Thus, in some embodiments, inoculant compositions of the present disclosure comprise one or more maltodextrins having a DEV of about 15 to about 20 and one or more sugar alcohols in a ratio of about 45:55, 50:50, 55:45, 60:40, 65:35, 70:30, 75:25, 80:20, 85:15, 90:10, 95:5.

In some embodiments, inoculant compositions of the present disclosure comprise one or more monosaccharides and/or disaccharides and one or more sugar alcohols in a ratio of about 1:99 to about 99:1 (by weight, based upon the respective weight percentages of the mono- and/or disaccharide(s) and sugar alcohol(s) in the inoculant composition). For example, inoculant compositions of the present disclosure may comprise one or more monosaccharides and/or disaccharides (e.g. arabinose, fructose, glucose, maltose, sucrose and/or trehalose) and one or more sugar alcohols (e.g. arabitol, mannitol. sorbitol and/or xylitol) in a mono- and/or disaccharide: sugar alcohol ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5 or more, preferably about 50:50, 55:45, 60:40, 65:35, 70:30, 75:25, 80:20, 85:15, 90:10, 95:5 or more.

In some embodiments, inoculant compositions of the present disclosure comprise one or more protectants in an amount/concentration sufficient to ensure microbial spores/vegetative cells microorganisms remain viable in inoculant compositions of the present disclosure following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application to plant propagation material (optionally, seed);

application to plant propagation material and desiccation by about 5, 10, 15, 20, 25, 30, 35, 40, 45, 50, 55, 60, 65, 70, 75, 80, 85, 90, 95% or more;

application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

foliar application;

foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, the amount(s)/concentration(s) of the stabilizer(s) included in the inoculant composition is/are selected to ensure at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of the microorganisms in the inoculant composition remain viable following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application to plant propagation material (optionally, seed);

application to plant propagation material and desiccation by about 5, 10, 15, 20, 25, 30, 35, 40, 45, 50, 55, 60, 65, 70, 75, 80, 85, 90, 95% or more;

application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

foliar application;

foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, the amount(s)/concentration(s) of the stabilizer(s) included in the inoculant composition is/are selected to ensure at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$ or more colony-forming units per gram and/or milliliter of inoculant composition remain viable following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application to plant propagation material (optionally, seed);

application to plant propagation material and desiccation by about 5, 10, 15, 20, 25, 30, 35, 40, 45, 50, 55, 60, 65, 70, 75, 80, 85, 90, 95% or more;

application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

foliar application;

foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

Inoculant compositions of the present disclosure may comprise any suitable agriculturally acceptable dispersant(s), including, but not limited to, surfactants and wetting agents.

In some embodiments, inoculant compositions of the present disclosure comprise one or more anionic surfactants. For example, in some embodiments, inoculant compositions of the present disclosure comprise one or more water-soluble anionic surfactants and/or one or more water-in-soluble anionic surfactants, optionally one or more anionic surfactants selected from the group consisting of alkyl carboxylates (e.g., sodium stearate), alkyl sulfates (e.g., alkyl lauryl sulfate, sodium lauryl sulfate), alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarconsinates, acyl isethionates, N-acyl taurates, N-acyl-N-alkyltaurates, benzene sulfonates, cumene sulfonates, dioctyl sodium sulfosuccinate, ethoxylated sulfo-succinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and xylene sulfonates.

In some embodiments, inoculant compositions of the present disclosure comprise one or more cationic surfactants. For example, in some embodiments, inoculant compositions of the present disclosure comprise one or more pH-dependent amines and/or one or more quaternary ammonium cations, optionally one or more cationic surfactants selected from the group consisting of alkyltrimethylammonium salts (e.g., cetyl trimethylammonium bromide, cetyl trimethylammonium chloride), cetylpyridinium chloride, benzalkonium chloride, benzethonium chloride, 5-Bromo-5-nitro-1,3-dioxane, dimethyldioctadecylammonium chloride, cetrimonium bromide, dioctadecyldimethylammonium bromide and/or octenidine dihydrochloride.

In some embodiments, inoculant compositions of the present disclosure comprise one or more nonionic surfactants. For example, in some embodiments, inoculant compositions of the present disclosure comprise one or more water-soluble nonionic surfactants and/or one or more water-insoluble nonionic surfactants, optionally one or more nonionic surfactants selected from the group consisting of alcohol ethoxylates (e.g., TERGITOL™ 15-S surfactants, such as TERGITOL™15-S-9 (The Dow Chemical Company, Midland, MI)), alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers (e.g.,), glycerol esters, glycol alkyl ethers (e.g., polyoxyethylene glycol alkyl ethers, polyoxypropylene glycol alkyl ethers,), glycol alkylphenol ethers (e.g., polyoxyethylene glycol alkylphenol ethers,), glycol esters, monolaurin, pentaethylene glycol monododecyl ethers, poloxamer, polyamines, polyglycerol polyricinoleate, polysorbate, poly-oxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pynolidones, sugar-based alkyl polyglycosides, sulfoanylamides, sorbitan fatty acid alcohol ethoxylates, sorbitan fatty acid ester ethoxylates, sorbitan fatty acid ester and/or tertiary acetylenic glycols.

In some embodiments, inoculant compositions of the present disclosure comprise at least one nonionic surfactant. In some embodiments, inoculant compositions of the present disclosure comprise at least one water insoluble nonionic surfactant and at least one water soluble nonionic surfactant. In some embodiments, inoculant compositions of the present disclosure comprise a combination of nonionic surfactants having hydrocarbon chains of substantially the same length.

In some embodiments, inoculant compositions of the present disclosure comprise one or more zwitterionic surfactants. For example, in some embodiments, inoculant compositions of the present disclosure comprise one or more betaines and/or one or more sultaines, optionally one or more zwitterionic surfactants selected from the group consisting of 3-[(3-cholamidopropyl)dimethylammonio]-1-propanesulfonate, cocamidopropyl betaine, cocamidopropyl hydroxysultaine, phosphatidylserine, phosphatidyletha-nolamine, phosphatidylcholine and/or one or more sphingo-myelins.

In some embodiments, inoculant compositions of the present disclosure comprise one or more soaps and/or organosilicone surfactants. For example, in some embodiments, inoculant compositions of the present disclosure comprise one or more alkali metal salts of fatty acids.

In some embodiments, inoculant compositions of the present disclosure comprise one or more wetting agents. For example, in some embodiments, inoculant compositions of the present disclosure comprise one or more naphthalene sulfonates, optionally one or more alkyl naphthalene sulfonates (e.g., sodium alkyl naphthalene sulfonate), one or more isopropyl naphthalene sulfonates (e.g., sodium isopropyl naphthalene sulfonate) and/or one or more butyl naphthalene sulfonates (e.g., sodium n-butyl naphthalene sulfonate).

Selection of appropriate surfactants will depend on the intended application(s) and the microorganism(s) present in the inoculant composition. In general, the surfactant(s) will have low toxicity for the microorganism(s) in the inoculant composition and for the plant part(s) to which the inoculant composition is to be applied. In some embodiments, the surfactant(s) will be selected to wet and/or emulsify one or more soils.

Non-limiting examples of dispersants that may be useful in compositions of the present disclosure include Atlox™ (e.g., 4916, 4991; Croda International PLC, Edison, NJ), BIO-SOFT® (e.g., N series, such as N1-3, N1-7, N1-5, N1-9, N23-3, N2.3-6.5, N25-3, N25-7, N25-9, N91-2.5, N91-6, N91-8; Stepan Company, Northfield, IL), MAKON® nonionic surfactants (e.g., DA-4, DA-6 and DA-9; Stepan Company, Northfield, IL), MORWET® powders (Akzo Nobel Surface Chemistry LLC, Chicago, IL), MULTIWET™ surfactants (e.g., MO-70R, MO-85P, MO-85P-PW-(AP); Croda International PLC, Edison, NJ), SILWET® L-77 (Helena Chemical Company, Collierville, TN), SPAN™ surfactants (e.g., 20, 40, 60, 65, 80 and 85; Croda Inc., Edison NJ), TAMOL™ dispersants (The Dow Chemical Company, Midland, MI), TERGITOL™ surfactants (e.g., 15-S-9, TMN-6, TMN-100X and XD; The Dow Chemical Company, Midland, MI), TERSPERSE surfactants (e.g., 2001, 2020, 2100, 2105, 2158, 2700, 4894 and 4896; Hunstman Corp., The Woodlands, TX), TRITON™ surfactants (e.g., X-100; The Dow Chemical Company, Midland, MI), TWEEN® surfactants (e.g., TWEEN® 20, 21, 22, 23, 28, 40, 60, 61, 65, 80, 81 and 85; Croda International PLC, Edison, NJ) and combinations thereof. Additional examples of dispersants that may be included in inoculant compositions of the present disclosure may be found in BAIRD & ZUBLENA. 1993. SOIL FACTS: USING WETTING AGENTS (NONIONIC SURFACTANTS) ON SOIL (North Carolina Cooperative Extension Service Publication AG-439-25) (1993); BURGES, FORMULATION OF MICROBIAL BIOPESTICIDES: BENEFICIAL MICROORGANISMS, NEMATODES AND SEED TREATMENTS (Springer Science & Business Media) (2012); MCCARTY, WETTING AGENTS (Clemson University Cooperative Extension Service Publication) (2001).

Dispersants may be incorporated into inoculant compositions of the present disclosure in any suitable amount(s)/concentration(s). In some embodiments, inoculant compositions of the present disclosure comprise one or more dispersants in an amount/concentration of about 0.01 to about 25% (by weight) of the composition. For example, inoculant compositions of the present disclosure may comprise about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25% or more (by weight) of one or more dispersants. In some embodiments, inoculant compositions of the present disclosure comprise one or more dispersants in an amount/concentration of about 0.1, 0.2, 0.3, 0.4, 0.5, 0.6, 0.7, 0.8, 0.9 or 1 to about 1, 1.5, 2, 2.5, 3, 3.5, 4, 4.5, 5, 5.5, 6, 6.5, 7, 7.5, 8, 8.5, 9, 9.5 or 10% (by weight) of the composition. In some embodiments, inoculant compositions of the present disclosure comprise two, three, four, five or more dispersants in a combined amount/concentration of about 1 to about 10% (by weight), optionally about 1, 1.5, 2, 2.5, 3, 3.5, 4, 4.5, 5, 5.5, 6, 6.5, 7, 7.5, 8, 8.5, 9, 9.5 or 10% (by weight), of the composition. In some embodiments, inoculant compositions of the present disclosure comprise one or more commercial wetting agents and/or one or more surfactants used in accordance with the manufacturer's recommended amounts/concentrations.

As noted above, inoculant compositions of the present invention may comprise myriad agriculturally beneficial microbial spores. It is to understood that inoculant compositions of the present disclosure may comprise other agriculturally beneficial constituents such as biostimulants, microbial extracts, nutrients, pest attractants, pesticides and plant signal molecules.

Inoculant compositions of the present disclosure may comprise any suitable biostimulant(s), including, but not limited to, seaweed extracts (e.g., Ascophyllum nodosum extracts, such as alginate, Ecklonia maxima extracts, etc.), humic acids (e.g., potassium humate), fulvic acids, myoinositol, glycine and combinations thereof.

Inoculant compositions of the present disclosure may comprise any suitable microbial extract(s), including, but not limited to, bacterial extracts (e.g., extracts of media comprising one or more diazotrophs, phosphate-solubilizing microorganisms and/or biopesticides), fungal extracts and combinations thereof.

In some embodiments, inoculant compositions of the present disclosure comprise one or more aqueous microbial extracts. For example, in some embodiments, inoculant compositions of the present disclosure comprise one or more microbial extracts that contains more then 0.5% water by weight, based upon to the total weight of the composition, but less than 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5% water by weight, based upon the total weight of the composition.

In some embodiments, inoculant compositions of the present disclosure comprise one or more Azospirillum extracts (e.g., an extract of media comprising A. brasilense INTA Az-39), one or more Bradyrhizobium extracts (e.g., an extract of media comprising B. elkanii SEMIA 501, B. elkanii SEMIA 587, B. elkanii SEMIA 5019, B. japonicum NRRL B-50586 (also deposited as NRRL B-59565), B. japonicum NRRL B-50587 (also deposited as NRRL B-59566), B. japonicum NRRL B-50588 (also deposited as NRRL B-59567), B. japonicum NRRL B-50589 (also deposited as NRRL B-59568), B. japonicum NRRL B-50590 (also deposited as NRRL B-59569), B. japonicum NRRL B-50591 (also deposited as NRRL B-59570), B. japonicum NRRL B-50592 (also deposited as NRRL B-59571), B. japonicum NRRL B-50593 (also deposited as NRRL B-59572), B. japonicum NRRL B-50594 (also deposited as NRRL B-50493), B. japonicum NRRL B-50608, B. japonicum NRRL B-50609, B. japonicum NRRL B-50610, B. japonicum NRRL B-50611, B. japonicum NRRL B-50612, B. japonicum NRRL B-50726, B. japonicum NRRL B-50727, B. japonicum NRRL B-50728, B. japonicum NRRL B-50729, B. japonicum NRRL B-50730, B. japonicum SEMIA 566, B. japonicum SEMIA 5079, B. japonicum SEMIA 5080, B. japonicum USDA 6, B. japonicum USDA 110, B. japonicum USDA 122, B. japonicum USDA 123, B. japonicum USDA 127, B. japonicum USDA 129 and/or B. japonicum USDA 532C), one or more Rhizobium extracts (e.g., an extract of media comprising R. leguminosarum SO12A-2), one or more Sinorhizobium extracts (e.g., an extract of media comprising S. fredii CCBAU114 and/or S. fredii USDA 205), one or more Penicillium extracts (e.g., an extract of media comprising P. bilaiae ATCC 18309, P. bilaiae ATCC 20851, P. bilaiae ATCC 22348, P. bilaiae NRRL 50162, P. bilaiae NRRL 50169, P. bilaiae NRRL 50776, P. bilaiae NRRL 50777, P. bilaiae NRRL 50778, P. bilaiae NRRL 50777, P. bilaiae NRRL 50778, P. bilaiae NRRL 50779, P. bilaiae NRRL 50780, P. bilaiae NRRL 50781, P. bilaiae NRRL 50782, P. bilaiae NRRL 50783, P. bilaiae NRRL 50784, P. bilaiae NRRL 50785, P. bilaiae NRRL 50786, P. bilaiae NRRL 50787, P. bilaiae NRRL 50788, P. bilaiae RS7B-SD1, P. brevicompactum AgRF18, P. canescens ATCC 10419, P. expansum ATCC 24692, P. expansum YT02, P. fellatanum ATCC 48694, P. gaestrivorus NRRL 50170, P. glabrum DAOM 239074, P. glabrum CBS 229.28, P. janthinellum ATCC 10455, P. lanosocoeruleum ATCC 48919, P. radicum ATCC 201836, P. radicum FRR 4717, P. radicum FRR 4719, P. radicum N93/47267 and/or P. raistrickii ATCC 10490), one or more Pseudomonas extracts (e.g., an extract of media comprising P. jessenii PS06), one or more acaricidal, insecticidal and/or nematicidal extracts (e.g., an extract of media comprising Bacillus firmus I-1582, Bacillus mycoides AQ726, NRRL B-21664; Beauveria bassiana ATCC-74040, Beauveria bassiana ATCC-74250, Burkholderia sp. A396 sp. nov. rinojensis, NRRL B-50319, Chromobacterium subtsugae NRRL B-30655, Chromobacterium vaccinii NRRL B-50880, Flavobacterium H492, NRRL B-50584, Metarhizium anisopliae F52 (also known as Metarhizium anisopliae strain 52, Metarhizium anisopliae strain 7, Metarhizium anisopliae strain 43 and Metarhizium anisopliae BIO-1020, TAE-001; deposited as DSM 3884, DSM 3885, ATCC 90448, SD170 and ARSEF 7711) and/or *Paecilomyces fumosoroseus* FE991), and/or one or more fungicidal extracts (e.g., an extract of media comprising *Ampelomyces quisqualis* AQ 10@ (Intrachem Bio GmbH & Co. KG, Germany), *Aspergillus flavus* AFLA-GUARD® (Syngenta Crop Protection, Inc., CH), *Aureobasidium pullulans* BOTECTOR® (bio-ferm GmbH, Germany), *Bacillus pumilus* AQ717 (NRRL B-21662), *Bacillus pumilus* NRRL B-30087, *Bacillus* AQ175 (ATCC 55608), *Bacillus* AQ177 (ATCC 55609), *Bacillus subtilis* AQ713 (NRRL B-21661), *Bacillus subtilis* AQ743 (NRRL B-21665), *Bacillus amyloliquefaciens* FZB24, *Bacillus amyloliquefaciens* NRRL B-50349, *Bacillus amyloliquefaciens* TJ1000 (also known as 1BE, isolate ATCC BAA-390), *Bacillus thuringiensis* AQ52 (NRRL B-21619), *Candida oleophila* I-82 (e.g., ASPIRE®, Ecogen Inc., USA), *Candida saitoana* BIO-CURE® (in mixture with lysozyme; BASF, USA) and BIOCOAT® (ArystaLife Science, Ltd., Cary, NC), *Clonostachys rosea* f. *catenulata* (also referred to as *Gliocladium catenulatum*) J1446 (PRESTOP®, Verdera, Finland), *Coniothyrium minitans* CONTANS® (Prophyta, Germany), *Cryphonectria parasitica* (CNICM, France), *Cryptococcus albidus* YIELD PLUS® (Anchor Bio-Technologies, South Africa), *Fusarium oxysporum* BIOFOX® (from S.I.A.P.A., Italy) and FUSACLEAN® (Natural Plant Protection, France), *Gliocladium virens* GL-21 (SOILGARD®, Certis LLC, USA), *Metschnikowia fructicola* SHEMER® (Agrogreen, Israel), *Microdochium dimerum* ANTIBOT® (Agrauxine, France), *Muscodor albus* NRRL 30547, *Muscodor roseus* NRRL 30548, *Phlebiopsis gigantea* ROTSOP® (Verdera, Finland), *Pseudozyma flocculosa* SPORODEX® (Plant Products Co. Ltd., Canada), *Pythium oligandrum* DV74 (POLYVERSUM®, Remeslo SSRO, Biopreparaty, Czech Rep.), *Reynoutria* sachlinensis (e.g., REGALIA®, Marrone BioInnovations, USA), *Streptomyces* NRRL B-30145, *Streptomyces* M1064, *Streptomyces galbus* NRRL 30232, *Streptomyces lydicus* WYEC 108 (ATCC 55445), *Streptomyces violaceusniger* YCED 9 (ATCC 55660), *Streptomyces* WYE 53 (ATCC 55750), *Talaromyces flavus* V117b (PROTUS®, Prophyta, Germany), *Trichoderma asperellum* SKT-1 (ECO-HOPE®, Kumiai Chemical Industry Co., Ltd., Japan), *Trichoderma atroviride* LC52 (SENTINEL®, Agrimm Technologies Ltd, NZ), *Trichoderma harzianum* T-22 (PLANTSHIELD®, BioWorks Inc., USA), *Trichoderma harzianum* TH-35 (ROOT PRO®, from Mycontrol Ltd., Israel), *Trichoderma harzianum* T-39 (TRICHODEX®, Mycontrol Ltd., Israel; *TRICHODERMA* 2000®, Makhteshim Ltd., Israel), *Trichoderma harzianum* ICC012 and *Trichoderma viride* TRICHOPEL (Agrimm Technologies Ltd, NZ), *Trichoderma harzianum* ICC012 and *Trichoderma viride* ICC080 (REMEDIER® WP, Isagro Ricerca, Italy), *Trichoderma polysporum* and *Trichoderma harzianum* (BINAB®, BINAB Bio-Innovation AB, Sweden), *Trichoderma stromaticum* TRICOVAB® (C.E-.P.L.A.C., Brazil), *Trichoderma virens* GL-3, ATCC 58678, *Trichoderma viride* TRIECO® (Ecosense Labs. (India) Pvt. Ltd., India, BIO-CURE® F, T. Stanes & Co. Ltd., India), *Trichoderma viride* TV1 (Agribiotec srl, Italy), *Trichoderma viride* ICC080, and/or *Ulocladium oudemansii* HRU3 (BOTRY-ZEN®, Botry-Zen Ltd, NZ)).

Inoculant compositions of the present disclosure may comprise any suitable nutrient(s), including, but not limited to, organic acids (e.g., acetic acid, citric acid, lactic acid, malic acid, taurine, etc.), macrominerals (e.g., phosphorous, calcium, magnesium, potassium, sodium, iron, etc.), trace minerals (e.g., boron, cobalt, chloride, chromium, copper, fluoride, iodine, iron, manganese, molybdenum, selenium, zinc, etc.), vitamins, (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$, choline) vitamin C, vitamin D, vitamin E, vitamin K, carotenoids ((α-carotene, β-carotene, cryptoxanthin, lutein, lycopene, zeaxanthin, etc.) and combinations thereof. In some embodiments, inoculant compositions of the present disclosure comprise phosphorous, boron, chlorine, copper, iron, manganese, molybdenum and/or zinc.

Inoculant compositions of the present disclosure may comprise any suitable pest attractant(s) and/or feeding stimulant(s), including, but not limited to, brevicomin, ceralure, codlelure, cue-lure, disparlure, dominicalure, eugenol, frontalin, gossyplure, grandlure, hexalure, ipsdienol, ipsenol, japonilure, latitlure, lineatin, litlure, looplure, medlure, megatomic acid, methyl eugenol, moguchun, α-multistriatin, muscalure, orfalure, oryctalure, ostramone, rescalure, siglure, sulcatol, trimedlure and/or trunc-call.

Inoculant compositions of the present disclosure may comprise any suitable pesticide(s), including, but not limited to, fungicides, herbicides, insecticides, and nematicides. In some embodiments, inoculant compositions of the present disclosure comprise one or more biopesticides (e.g., one or more biofungicides, bioinsecticides and/or bionematicides).

Inoculant compositions of the present disclosure may comprise any suitable insecticide(s), including, but not limited to, biological insecticides and chemical insecticides. Insecticides may be selected so as to provide effective control against a broad spectrum of insects, including, but not limited to, insects from the orders Coleoptera, Dermaptera, Diptera, Hemiptera, Homoptera, Hymenoptera, Lepidoptera, Orthoptera and Thysanoptera. For example, inoculant compositions of the present disclosure may comprise one or more insecticides toxic to insects from the families Acrididae, Aleytodidae, Anobiidae, Anthomyiidae, Aphididae, Bostrichidae, Bruchidae, Cecidomyiidae, Cerambycidae, Cercopidae, Chrysomelidae, Cicadellidae, Coccinellidae, Cryllotalpidae, Cucujidae, Curculionidae, Dermestidae, Elateridae, Gelechiidae, Lygaeidae, Meloidae, Membracidae, Miridae, Noctuidae, Pentatomidae, Pyralidae, Scarabaeidae, Silvanidae, Spingidae, Tenebrionidae and/or Thripidae. In some embodiments, inoculant compositions of the present disclosure comprise an insecticide (or combination of insecticides) that is toxic to one or more species of *Acalymma*, *Acanthaoscelides* (e.g., *A. obtectus*,), *Anasa* (e.g., *A. tristis*), *Anastrepha* (e.g., A. ludens), *Anoplophora* (e.g., *A. glabripennis*), *Anthonomus* (e.g., *A. eugenii*), *Acyrthosiphon* (e.g., *A. pisum*), *Bactrocera* (e.g., *B. dosalis*), *Bemisia* (e.g., *B. argentifolii*, *B. tabaci*), *Brevicoryne* (e.g., *B. brassicae*), *Bruchidius* (e.g., *B. atrolineatus*), *Bruchus* (e.g., *B. atomarius*, *B. dentipes*, *B. lentis*, *B. pisorum* and/or *B. rufipes*), *Callosobruchus* (e.g., *C. chinensis*, *C. maculatus*, *C. rhodesianus*, *C. subinnotatus*, *C. theobromae*), *Caryedon* (e.g., *C. serratus*), Cassadinae, *Ceratitis* (e.g., *C. capitata*), Chrysomelinae, *Circulifer* (e.g., *C. tenellus*), Criocerinae, Cryptocephalinae, *Cryptolestes* (e.g., *C. ferrugineus*, *C. pusillis*, *C. pussilloides*), *Cylas* (e.g., *C. formicarius*), *Delia* (e.g., *D. antiqua*), *Diabrotica*, *Diaphania* (e.g., *D. nitidalis*), *Diaphorina* (e.g., *D. citri*), Donaciinae, *Ephestia* (e.g, *E. cautella*, *E. elutella*, *E.*, *keuhniella*), *Epilachna* (e.g., *E. varivestris*), *Epiphyas* (e.g., *E. postvittana*), Eumolpinae, Galerucinae, *Helicoverpa* (e.g., *H. zea*), *Heteroligus* (e.g., *H. meles*), *Iobesia* (e.g., *I. botrana*), *Lamprosomatinae*, *Lasioderma* (e.g., *L. serricorne*), *Leptinotarsa* (e.g., *L. decemlineata*), *Leptoglossus*, *Liriomyza* (e.g., *L. trifolii*), *Manducca*, *Melittia* (e.g., *M. cucurbitae*), *Myzus*

(e.g., *M. persicae*), *Nezara* (e.g., *N. viridula*), *Orzaephilus* (e.g., *O. merator, O. surinamensis*), *Ostrinia* (e.g., *O. nubilalis*), *Phthorimaea* (e.g., *P. operculella*), *Pieris* (e.g., *P. rapae*), *Plodia* (e.g., *P. interpunctella*), *Plutella* (e.g., *P. xylostella*), *Popillia* (e.g., *P. japonica*), *Prostephanus* (e.g., *P. truncates*), *Psila, Rhizopertha* (e.g., *R. dominica*), *Rhopalosiphum* (e.g., *R. maidis*), *Sagrinae, Solenopsis* (e.g., *S. Invicta*), *Spilopyrinae, Sitophilus* (e.g., *S. granaries, S. oryzae* and/or *S. zeamais*), *Sitotroga* (e.g., *S. cerealella*), *Spodoptera* (e.g., *S. frugiperda*), *Stegobium* (e.g., *S. paniceum*), *Synetinae, Tenebrio* (e.g., *T. malens* and/or *T. molitor*), *Thrips* (e.g., *T. tabaci*), *Trialeurodes* (e.g., *T. vaporariorum*), *Tribolium* (e.g., T. castaneum and/or *T. confusum*), *Trichoplusia* (e.g., *T. ni*), *Trogoderma* (e.g., *T. granarium*) and *Trogossitidae* (e.g., *T. mauritanicus*). Additional species of insects that may be targeted by inoculant compositions of the present disclosure may be found in CAPINERA, HANDBOOK OF VEGETABLE PESTS (2001) and Steffey and Gray, *Managing Insect Pests*, in ILLINOIS AGRONOMY HANDBOOK (2008).

Inoculant compositions of the present disclosure may comprise any suitable nematicide(s) including, but not limited to, biological nematicides and chemical nematicides. Nematicides may be selected so as to provide effective control against a broad spectrum of *nematodes*, including, but not limited to, phytoparasitic *nematodes* from the classes Chromadorea and Enoplea. In some embodiments, inoculant compositions of the present disclosure comprise a nematicide (or combination of nematicides) that is toxic to one or more strains of *Anguina, Aphelenchoides, Belonolaimus, Bursaphelenchus, Ditylenchus, Globodera, Helicotylenchus, Heterodera, Hirschmanniella, Meloidogyne, Naccobus, Pratylenchus, Radopholus, Rotylenshulus, Trichodorus, Tylenchulus* and/or *Xiphinema*. Additional examples of *nematodes* that may be targeted by inoculant compositions of the present disclosure may be found in CAPINERA, HANDBOOK OF VEGETABLE PESTS (2001) and Niblack, *Nematodes*, in ILLINOIS AGRONOMY HANDBOOK (2008).

As discussed above, inoculant compositions of the present disclosure may comprise one or more biological insecticides and/or nematicides (i.e., one or more microorganisms the presence and/or output of which is toxic to an acarid, insect and/or nematode).

In some embodiments, inoculant compositions of the present disclosure comprise one or more chemical insecticides and/or nematicides. For example, in some embodiments, inoculant compositions of the present disclosure comprise one or more carbamates, diamides, macrocyclic lactones, neonicotinoids, organophosphates, phenylpyrazoles, pyrethrins, spinosyns, synthetic pyrethroids, tetronic acids and/or tetramic acids. Non-limiting examples of chemical insecticides and nematicides that may be useful in inoculant compositions of the present disclosure include acrinathrin, alpha-cypermethrin, betacyfluthrin, cyhalothrin, cypermethrin, deltamethrin, csfenvalcrate, etofenprox, fenpropathrin, fenvalerate, flucythrinate, fosthiazate, lambda-cyhalothrin, gamma-cyhalothrin, permethrin, taufluvalinate, transfluthrin, zeta-cypermethrin, cyfluthri, bifenthrin, tefluthrin, eflusilanat, fubfenprox, pyrethrin, resmethrin, imidacloprid, acetamiprid, thiamethoxam, nitenpyram, thiacloprid, dinotefuran, clothianidin, imidaclothiz, chlorfluazuron, diflubenzuron, lufenuron, teflubenzuron, triflumuron, novaluron, flufenoxuron, hexaflumuron, bistrifluoron, noviflumuron, buprofezin, cyromazine, methoxyfenozide, tebufenozide, halofenozide, chromafenozide, endosulfan, fipronil, ethiprole, pyrafluprole, pyriprole, flubendiamide, chlorantraniliprole (e.g., Rynaxypyr), cyazypyr, emamectin, emamectin benzoate, abamectin, ivermectin, milbemectin, lepimectin, tebufenpyrad, fenpyroximate, pyridaben, fenazaquin, pyrimidifen, tolfenpyrad, dicofol, cyenopyrafen, cyflumetofen, acequinocyl, fluacrypyrin, bifenazate, diafenthiuron, etoxazole, clofentezine, spinosad, triarathen, tetradifon, propargite, hexythiazox, bromopropylate, chinomethionat, amitraz, pyrifluquinazon, pymetrozine, flonicamid, pyriproxyfen, diofenolan, chlorfenapyr, metaflumizone, indoxacarb, chlorpyrifos, spirodiclofen, spiromesifen, spirotetramat, pyridalyl, spinctoram, acephate, triazophos, profenofos, oxamyl, spinetoram, fenamiphos, fenamipclothiahos, 4-{[(6-chloropyrid-3-yl)methyl](2,2-difluoroethyl)amino}furan-2(5H)-one, cadusaphos, carbaryl, carbofuran, ethoprophos, thiodicarb, aldicarb, aldoxycarb, metamidophos, methiocarb, sulfoxaflor, cyantraniliprole and tioxazafen and combinations thereof. In some embodiments, inoculant compositions of the present disclosure comprise abamectin, aldicarb, aldoxycarb, bifenthrin, carbofuran, chlorantraniliporle, chlothianidin, cyfluthrin, cyhalothrin, cypermethrin, cyantraniliprole, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, spinetoram, spinosad, spirodichlofen, spirotetramat, tefluthrin, thiacloprid, thiamethoxam and/or thiodicarb. In some embodiments, inoculant compositions of the present disclosure comprise an insecticide selected from the group consisting of clothianidin, thiamethoxam, imidacloprid, cyantraniliprole, chlorantraniliprole, fluopyram and tioxazafen.

Additional examples of insecticides and nematicides that may be included in inoculant compositions of the present disclosure may be found in Steffey and Gray, *Managing Insect Pests*, in ILLINOIS AGRONOMY HANDBOOK (2008) and Niblack, *Nematodes*, in ILLINOIS AGRONOMY HANDBOOK (2008).

In some embodiments, inoculant compositions of the present disclosure comprise one or more commercial insecticides and nematicides used in accordance with the manufacturer's recommended amounts/concentrations.

Inoculant compositions of the present disclosure may comprise any suitable fungicide(s), including, but not limited to, biological fungicides and chemical fungicides. Fungicides may be selected so as to provide effective control against a broad spectrum of phytopathogenic fungi (and fungus-like organisms), including, but not limited to, soilborne fungi from the classes Ascomycetes, Basidiomycetes, Chytridiomycetes, Deuteromycetes (syn. Fungi imperfecti), Peronosporomycetes (syn. Oomycetes), Plasmodiophoromycetes and Zygomycetes. In some embodiments, inoculant compositions of the present disclosure comprise a fungicide (or combination of fungicides) that is toxic to one or more strains of Albugo (e.g., *A. candida*), *Alternaria* (e.g., *A. alternata*), *Aspergillus* (e.g., *A. candidus, A. clavatus, A. flavus, A. fumigatus, A. parasiticus, A. restrictus, A. sojae, A. solani*), *Blumeria* (e.g., *B. graminis*), *Botrytis* (e.g., *B. cinerea*), *Cladosporum* (e.g., *C. cladosporioides*), *Colletotrichum* (e.g., *C. acutatum, C. boninense, C. capsici, C. caudatum, C. coccodes, C. crassipes, C. dematium, C. destructivum, C. fragariae, C. gloeosporioides, C. graminicola, C. kehawee, C. lindemuthianum, C. musae, C. orbiculare, C. spinaceae, C. sublineolum, C. trifolii, C. truncatum*), *Fusarium* (e.g., *F. graminearum, F. moniliforme, F. oxysporum, F. roseum, F. tricinctum*), *Helminthosporium, Magnaporthe* (e.g., *M. grisea, M. oryzae*), *Melamspora* (e.g., *M. lini*), *Mycosphaerella* (e.g., *M. graminicola*), *Nematospora*,

*Penicillium* (e.g., *P. rugulosum, P. verrucosum*), *Phakopsora* (e.g., *P. pachyrhizi*), *Phomopsis, Phytiphtoria* (e.g., *P. infestans*), *Puccinia* (e.g., *P. graminis, P. striiformis, P. tritici, P. triticina*), *Pucivinia* (e.g., *P. graministice*), *Pythium, Pytophthora, Rhizoctonia* (e.g., *R. solani*), *Scopulariopsis, Selerotinia, Thielaviopsis* and/or *Ustilago* (e.g., *U. maydis*). Additional examples of fungi that may be targeted by inoculant compositions of the present disclosure may be found in Bradley, *Managing Diseases*, in ILLINOIS AGRONOMY HANDBOOK (2008).

As discussed above, inoculant compositions of the present disclosure may comprise one or more biological fungicides (i.e., one or more microorganisms the presence and/or output of which is toxic to a fungus).

In some embodiments, inoculant compositions of the present disclosure comprise one or more chemical fungicides. For example, in some embodiments, inoculant compositions of the present disclosure comprise one or more aromatic hydrocarbons, benzimidazoles, benzthiadiazole, carboxamides, carboxylic acid amides, morpholines, phenylamides, phosphonates, quinone outside inhibitors (e.g. strobilurins), thiazolidines, thiophanates, thiophene carboxamides and/or triazoles. Non-limiting examples of chemical fungicides that may be useful in inoculant compositions of the present disclosure include strobilurins, such as azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide; carboxamides, such as carboxanilides (e.g., benalaxyl, benalaxyl-M, benodanil, bixafen, boscalid, carboxin, fenfuram, fenhexamid, flutolanil, fluxapyroxad, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methyl-thiazole-5-carboxanilide, N-(4'-trifluoromethylthio-biphenyl-2-yl)-3-difluoromethyl-1-methyl-1H-pyrazole-4-carboxamide, N-(2-(1,3,3-trimethylbutyl)-phenyl)-1,3-dimethyl-5-fluoro-1H-pyrazole-4-carboxamide), carboxylic morpholides (e.g., dimethomorph, flumorph, pyrimorph), benzoic acid amides (e.g., flumetover, fluopicolide, fluopyram, zoxamide), carpropamid, dicyclomet, mandiproamid, oxytetracyclin, silthiofam and N-(6-methoxy-pyridin-3-yl) cyclopropanecarboxylic acid amide; azoles, such as triazoles (e.g., azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole) and imidazoles (e.g., cyazofamid, imazalil, pefurazoate, prochloraz, triflumizol); heterocyclic compounds, such as pyridines (e.g., fluazinam, pyrifenox (cf.D1b), 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine), pyrimidines (e.g., bupirimate, cyprodinil, diflumetorim, fenarimol, ferimzone, mepanipyrim, nitrapyrin, nuarimol, pyrimethanil), piperazines (e.g., triforine), pirroles (e.g., fenpiclonil, fludioxonil), morpholines(e.g., aldimorph, dodemorph, dodemorph-acetate, fenpropimorph, tridemorph), piperidines (e.g., fenpropidin); dicarboximides (e.g., fluoroimid, iprodione, procymidone, vinclozolin), non-aromatic 5-membered heterocycles (e.g., famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester), acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo-[1,5-a]pyrimidine; benzimidazoles, such as carbendazim; and other active substances, such as guanidines (e.g., guanidine, dodine, dodine free base, guazatine, guazatine-acetate, iminoctadine), iminoctadine-triacetate and iminoctadine-tris(albesilate); antibiotics (e.g., kasugamycin, kasugamycin hydrochloride-hydrate, streptomycin, polyoxine and validamycin A), nitrophenyl derivates (e.g., binapacryl, dicloran, dinobuton, dinocap, nitrothal-isopropyl, tecnazen). organometal compounds (e.g., fentin salts, such as fentin-acetate, fentin chloride, fentin hydroxide); sulfur-containing heterocyclyl compounds (e.g., dithianon, isoprothiolane), organophosphorus compounds (e.g., edifenphos, fosetyl, fosetyl-aluminum, iprobenfos, phosphorus acid and its salts, pyrazophos, tolclofos-methyl), organochlorine compounds (e.g., chlorothalonil, dichlofluanid, dichlorophen, flusulfamide, hexachlorobenzene, pencycuron, pentachlorphenole and its salts, phthalide, quintozene, thiophanate-methyl, thiophanate, tolylfluanid, N-(4-chloro-2-nitro-phenyl)-N-ethyl-4-methyl-benzenesulfonamide) and inorganic active substances (e.g., Bordeaux mixture, copper acetate, copper hydroxide, copper oxychloride, basic copper sulfate, sulfur) and combinations thereof. In some embodiments, inoculant compositions of the present disclosure comprise acibenzolar-S-methyl, azoxystrobin, benalaxyl, bixafen, boscalid, carbendazim, cyproconazole, dimethomorph, epoxiconazole, fludioxonil, fluopyram, fluoxastrobin, flutianil, flutolanil, fluxapyroxad, fosetyl-Al, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thiabendazole, thifluzamide, thiophanate, tolclofos-methyl, trifloxystrobin and triticonazole. In some embodiments, inoculant compositions of the present disclosure comprise azoxystrobin, pyraclostrobin, fluoxastrobin, trifloxystrobin, ipconazole, prothioconazole, sedaxane, fludioxonil, metalaxyl, mefenoxam, thiabendazole, fluxapyroxad and/or fluopyram.

Additional examples of fungicides that may be included in inoculant compositions of the present disclosure may be found in Bradley, *Managing Diseases*, in ILLINOIS AGRONOMY HANDBOOK (2008).

Inoculant compositions of the present disclosure may comprise any suitable herbicide(s), including, but not limited to, biological herbicides and chemical herbicides. Herbicides may be selected so as to provide effective control against a broad spectrum of plants, including, but not limited to, plants from the families Asteraceae, Caryophyllaceae, Poaceae and Polygonaceae. In some embodiments, inoculant compositions of the present disclosure comprise an herbicide (or combination of herbicides) that is toxic to one or more strains of *Echinochloa* (e.g., *E. brevipedicellata, E. callopus, E. chacoensis, E. colona, E. crus-galli, E. cruspavonis, E. elliptica, E. esculenta, E. frumentacea, E. glabrescens, E. haploclada, E. helodes, E. holciformis, E.*

*inundata, E. jaliscana, E. Jubata, E. kimberleyensis, E. lacunaria, E. macrandra, E. muricata, E. obtusiflora, E. oplismenoides, E. orzyoides, E. paludigena, E. picta, E. pithopus, E. polystachya, E. praestans, E. pyramidalis, E. rotundiflora, E. stagnina, E. telmatophila, E. turneriana, E. ugandensis, E. walteri), Fallopia* (e.g., *F. baldschuanica, F. japonica, F. sachalinensis*), *Stellaria* (e.g., *S. media*) and/or *Taraxacum* (e.g., *T. albidum, T. aphrogenes, T. brevicorniculatum, T. californicum, T. centrasiatum, T. ceratophorum, T. erythrospermum, T. farinosum, T. holmboei, T. japonicum, T. kok-saghyz, T. laevigatum T. officinale, T. platycarpum*). Additional species of plants that may be targeted by inoculant compositions of the present disclosure may be found in Hager, *Weed Management*, in ILLINOIS AGRONOMY HANDBOOK (2008) and LOUX ET AL., WEED CONTROL GUIDE FOR OHIO, INDIANA AND ILLINOIS (2015).

As discussed above, inoculant compositions of the present disclosure may comprise one or more biological herbicides (i.e., one or more microorganisms the presence and/or output of which is toxic to a plant).

In some embodiments, inoculant compositions of the present disclosure comprise one or more chemical herbicides. For example, in some embodiments, inoculant compositions of the present disclosure comprise one or more acetyl CoA carboxylase (ACCase) inhibitors, acetolactate synthase (ALS) inhibitors, acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin herbicide salts, auxin transport inhibitors, nucleic acid inhibitors and/or one or more salts, esters, racemic mixtures and/or resolved isomers thereof. Non-limiting examples of chemical herbicides that may be useful in inoculant compositions of the present disclosure include 2,4-dichlorophenoxyacetic acid (2,4-D), 2,4,5-trichlorophenoxyacetic acid (2,4,5-T), ametryn, amicarbazone, aminocyclopyrachlor, acetochlor, acifluorfen, alachlor, atrazine, azafenidin, bentazon, benzofenap, bifenox, bromacil, bromoxynil, butachlor, butafenacil, butroxydim, carfentrazone-ethyl, chlorimuron, chlorotoluro, clethodim, clodinafop, clomazone, cyanazine, cycloxydim, cyhalofop, desmedipham, desmetryn, dicamba, diclofop, dimefuron, diuron, dithiopyr, fenoxaprop, fluazifop, fluazifop-P, fluometuron, flufenpyr-ethyl, flumiclorac-pentyl, flumioxazin, fluoroglycofen, fluthiacet-methyl, fomesafe, fomesafen, glyphosate, glufosinate, haloxyfop, hexazinone, imazamox, imazaquin, imazethapyr, ioxynil, isoproturon, isoxaflutole, lactofen, linuron, mecoprop, mecoprop-P, mesotrione, metamitron, metazochlor, methibenzuron, metolachlor (and S-metolachlor), metoxuron, metribuzin, monolinuron, oxadiargyl, oxadiazon, oxyfluorfen, phenmedipham, pretilachlor, profoxydim, prometon, prometry, propachlor, propanil, propaquizafop, propisochlor, pyraflufen-ethyl, pyrazon, pyrazolynate, pyrazoxyfen, pyridate, quizalofop, quizalofop-P (e.g., quizalofop-ethyl, quizalofop-P-ethyl, clodinafop-propargyl, cyhalofop-butyl, diclofop-methyl, fenoxaprop-P-ethyl, fluazifop-P-butyl, haloxyfop-methyl, haloxyfop-R-methyl), saflufenacil, sethoxydim, siduron, simazine, simetryn, sulcotrione, sulfentrazone, tebuthiuron, tembotrione, tepraloxydim, terbacil, terbumeton, terbuthylazine, thaxtomin (e.g., the thaxtomins described in U.S. Pat. No. 7,989,393), thenylchlor, tralkoxydim, triclopyr, trietazine, tropramezone, salts and esters thereof; racemic mixtures and resolved isomers thereof and combinations thereof. In some embodiments, inoculant compositions of the present disclosure comprise acetochlor, clethodim, dicamba, flumioxazin, fomesafen, glyphosate, glufosinate, mesotrione, quizalofop, saflufenacil, sulcotrione, ethyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate and/or 2,4-D. In some embodiments, inoculant compositions of the present disclosure comprise glyphosate, glufosinate, dicamba, 2,4-D, acetochlor, metolachlor, pyroxasulfone, flumioxazin, fomesafen, lactofen, metribuzin, mesotrione, and/or ethyl 2-((3-(2-chloro-4-fluoro-5-(3-methyl-2,6-dioxo-4-(trifluoromethyl)-2,3-dihydropyrimidin-1(6H)-yl)phenoxy)pyridin-2-yl)oxy)acetate.

Additional examples of herbicides that may be included in inoculant compositions of the present disclosure may be found in Hager, *Weed Management*, in ILLINOIS AGRONOMY HANDBOOK (2008) and LOUX ET AL., WEED CONTROL GUIDE FOR OHIO, INDIANA AND ILLINOIS (2015).

Inoculant compositions of the present disclosure may comprise any suitable plant signal molecule(s), including, but not limited to, lipo-chitooligosaccharides (LCOs), chitooligosaccharides (COs), chitinous compounds, flavonoids, jasmonic acid or derivatives thereof, *linoleic* acid or derivatives thereof, linolenic acid or derivatives thereof and karrikins.

Inoculant compositions of the present disclosure may comprise any suitable LCO(s). LCOs, sometimes referred to as symbiotic nodulation (Nod) signals or Nod factors, consist of an oligosaccharide backbone of β-1,4-linked N-acetyl-D-glucosamine ("GlcNAc") residues with an N-linked fatty acyl chain condensed at the non-reducing end. LCOs differ in the number of GlcNAc residues in the backbone, in the length and degree of saturation of the fatty acyl chain and in the substitutions of reducing and non-reducing sugar residues. See, e.g., Denarie, et al., ANN. REV. BIOCHEM. 65:503 (1996); Hamel, et al., PLANTA 232:787 (2010); Prome, et al., PURE & APPL. CHEM. 70(1):55 (1998). Non-limiting examples of LCOs include the LCOs described in International Patent Application No. PCT/US2016/050529. In some embodiments, inoculant compositions of the present disclosure comprise one, two, three, four, five, six, seven, eight, nine, ten, or more of the LCOs represented by structures V-XXXIII of International Patent Application No. PCT/US2016/050529 and/or one, two, three, four, five, six, seven, eight, nine, ten, or more analogues, derivatives, hydrates, isomers, salts and/or solvates of LCOs represented by structures V-XXXIII of International Patent Application No. PCT/US2016/050529.

LCOs included in compositions and methods of the present disclosure may be obtained from any suitable source. According to some embodiments, the LCO is obtained (i.e., isolated and/or purified) from a bacterial strain. According to some embodiments, the inoculant composition comprises one or more LCOs obtained from a of *Azorhizobium, Bradyrhizobium* (e.g., *B. japonicum*), *Mesorhizobium, Rhizobium* (e.g., *R. leguminosarum*), or *Sinorhizobium* (e.g., *S. meliloti*). According to some embodiments, the LCO is obtained (i.e., isolated and/or purified) from a mycorrhizal fungus. For example, in some embodiments, inoculant compositions of the present disclosure comprise one or more LCOs obtained from a strain of Glomerocycota (e.g., *Glomus intraradicus*). See, e.g., WO 2010/049751 (in which the LCOs are referred to as "Myc factors"). According to some embodiments, the LCO is synthetic. According to some embodiments, the inoculant composition comprises one or more of the synthetic LCOs described in WO 2005/063784, WO 2007/117500 and/or WO 2008/071674. In some embodiments, the synthetic LCO contains one or more modifications or substitutions, such as those described in Spaink, CRIT. REV. PLANT SCI. 54:257 (2000) and D'Haeze, supra. LCOs and precursors for the construction of LCOs (e.g., COs, which are themselves useful as plant signal molecules) may be synthesized by genetically engineered organisms. See, e.g., Samain et al., CARBOHYDRATE RES. 302:35 (1997); Cottaz, et al., METH. ENG. 7(4):311 (2005); and Samain, et al., J. BIO-TECHNOL. 72:33 (1999) (e.g., FIG. 1 therein, which shows structures of COs that can be made recombinantly in *E. coli* harboring different combinations of genes nodBCHL).

LCOs (and derivatives thereof) may be utilized in various forms of purity and may be used alone or in the form of a culture of LCO-producing bacteria or fungi. In some embodiments, the LCO(s) included in inoculant compositions of the present disclosure is/are at least 70%, 75%, 80%, 85%, 90%, 91%, 92%, 93%, 94%, 95%, 96%, 97%, 98%, 99%, 99.5% or more pure.

Inoculant compositions of the present disclosure may comprise any suitable CO(s). COs, sometimes referred to as N-acetylchitooligosaccharides, are also composed of GlcNAc residues but have side chain decorations that make them different from chitin molecules [$(C_8H_{13}NO_5)_n$, CAS No. 1398-61-4] and chitosan molecules [$(C_5H_{11}NO_4)_n$, CAS No. 9012-76-4]. See, e.g., D'Haeze et al., GLYCOBIOL. 12(6):79R (2002); Demont-Caulet et al., PLANT PHYSIOL. 120(1):83 (1999); Hanel et al., PLANTA 232: 787 (2010); Muller et al., PLANT PHYSIOL.124:733 (2000); Robina et al., TETRAHEDRON 58:521-530 (2002); Rouge et al., *Docking of Chitin Oligomers and Nod Factors on Lectin Domains of the LysM-RLK Receptors in the Medicago-Rhizobium Symbiosis*, in THE MOLECULAR IMMUNOLOGY OF COMPLEX CARBOHYDRATES-3 (Springer Science, 2011); Van der Holst et al., CURR. OPIN. STRUC. BIOL. 11:608 (2001); and Wan et al., PLANT CELL 21:1053 (2009); PCT/F100/00803 (2000). COs differ from LCOs in that they lack the pendant fatty acid chain that is characteristic of LCOs. Non-limiting examples of LCOs include the COs described in International Patent Application No. PCT/US2016/050529. In some embodiments, inoculant compositions of the present disclosure comprise one, two, three, four, five, six, seven, eight, nine, ten, or more of the COs represented by structures XXXVI-XXXIX of International Patent Application No. PCT/US2016/ 050529 and/or one, two, three, four, five, six, seven, eight, nine, ten, or more analogues, derivatives, hydrates, isomers, salts and/or solvates of COs represented by structures XXXVI-XXXIX of International Patent Application No. PCT/US2016/050529.

COs included in compositions and methods of the present disclosure may be obtained from any suitable source. According to some embodiments, the CO is derived from an LCO. According to some embodiments, the inoculant composition comprises one or more COs derived from an LCO obtained (i.e., isolated and/or purified) from a strain of *Azorhizobium, Bradyrhizobium* (e.g., *B. japonicum*), *Mesorhizobium, Rhizobium* (e.g., *R. leguminosarum*), *Sinorhizobium* (e.g., *S. meliloti*), or mycorhizzal fungus (e.g., *Glomus intraradicus*). In some embodiments, the CO is derived from an LCO represented by one or more of formulas I—IV and/or structures V-XXXIII of International Patent Application No. PCT/US2016/050529. Thus, in some embodiments, inoculant compositions of the present disclosure may comprise one or more COs represented by one or more of structures V-XXXIII of International Patent Application No. PCT/US2016/050529 except that the pendant fatty acid is replaced with a hydrogen or methyl group. According to some embodiments, the CO is synthetic. Methods for the preparation of recombinant COs are known in the art. See, e.g., Cottaz et al., METH. ENG. 7(4):311 (2005); Samain et al., CARBOHYDRATE RES. 302:35 (1997.); and Samain et al., J. BIOTECHNOL. 72:33 (1999).

COs (and derivatives thereof) may be utilized in various forms of purity and may be used alone or in the form of a culture of CO-producing bacteria or fungi. In some embodiments, the CO(s) included in inoculant compositions of the present disclosure is/are at least 70%, 75%, 80%, 85%, 90%, 91%, 92%, 93%, 94%, 95%, 96%, 97%, 98%, 99%, 99.5% or more pure.

Inoculant compositions of the present disclosure may comprise any suitable chitinous compound(s), including, but not limited to, chitin (IUPAC: N-[5-[[3-acetylamino-4,5-dihydroxy-6-(hydroxymethyl)oxan-2yl]methoxymethyl]-2-[[5-acetylamino-4,6-dihydroxy-2-(hydroxymethyl)oxan-3-yl]methoxymethyl]-4-hydroxy-6-(hydroxymethyl)oxan-3-ys]ethanamide), chitosan(IUPAC: 5-amino-6-[5-amino-6-[5-amino-4,6-dihydroxy-2(hydroxymethyl)oxan-3-yl]oxy-4-hydroxy-2-(hydroxymethyl)oxan-3-yl]oxy-2-(hydroxymethyl)oxane-3,4-diol) and isomers, salts and solvates thereof. Chitins and chitosans, which are major components of the cell walls of fungi and the exoskeletons of insects and crustaceans, are composed of GlcNAc residues. Chitins and chitosans included in compositions and methods of the present disclosure may be obtained from any suitable source. Chitins and chitosans may be obtained commercially or prepared from insects, crustacean shells, or fungal cell walls. Methods for the preparation of chitin and chitosan are known in the art. See, e.g., U.S. Pat. Nos. 4,536,207 (preparation from crustacean shells) and 5,965, 545 (preparation from crab shells and hydrolysis of commercial chitosan); Pochanavanich, et al., LETT. APPL. MICROBIOL. 35:17 (2002) (preparation from fungal cell walls). Deacetylated chitins and chitosans may be obtained that range from less than 35% to greater than 90% deacetylation and cover a broad spectrum of molecular weights, e.g., low molecular weight chitosan oligomers of less than 15kD and chitin oligomers of 0.5 to 2kD; "practical grade" chitosan with a molecular weight of about 15kD; and high molecular weight chitosan of up to 70kD. Chitin and chitosan compositions formulated for seed treatment are commercially available. Commercial products include, for example, ELEXA® (Plant Defense Boosters, Inc.) and BEYOND™ (Agrihouse, Inc.).

Inoculant compositions of the present disclosure may comprise any suitable flavonoid(s), including, but not limited to, anthocyanidins, anthoxanthins, chalcones, coumarins, flavanones, flavanonols, flavans and isoflavonoids, as well as analogues, derivatives, hydrates, isomers, polymers, salts and solvates thereof. Flavonoids are phenolic compounds having the general structure of two aromatic rings connected by a three-carbon bridge. Classes of flavonoids include are known in the art. See, e.g., Jain et al., J. PLANT BIOCHEM. & BIOTECHNOL. 11:1 (2002); Shaw et al., ENVIRON. MICROBIOL. 11:1867 (2006). Flavonoid compounds are commercially available, e.g., from Novozymes BioAg, Saskatoon, Canada; Natland International Corp., Research Triangle Park, NC; MP Biomedicals, Irvine, CA; LC Laboratories, Woburn MA. Flavonoid compounds may be isolated from plants or seeds, e.g., as described in U.S. Pat. Nos. 5,702,752; 5,990,291; and 6,146, 668. Flavonoid compounds may also be produced by genetically engineered organisms, such as yeast, as described in Ralston et al., PLANT PHYSIOL. 137:1375 (2005).

In some embodiments, inoculant compositions of the present disclosure comprise one or more anthocyanidins. For example, in some embodiments, inoculant compositions of the present disclosure comprise cyanidin, delphinidin, malvidin, pelargonidin, peonidin and/or petunidin.

In some embodiments, inoculant compositions of the present disclosure comprise one or more anthoxanthins. For example, in some embodiments, inoculant compositions of the present disclosure comprise one or more flavones (e.g., apigenin, baicalein, chrysin, 7,8-dihydroxyflavone, diosmin, flavoxate, 6-hydroxyflavone, luteolin, scutellarein, tangeritin and/or wogonin) and/or flavonols (e.g., amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, pyranoflavonols quercetin, quericitin, rhamnazin, rhamnetin, robinin, rutin, spiraeoside, troxerutin and/or zanthorhamnin).

In some embodiments, inoculant compositions of the present disclosure comprise one or more flavanones. For example, in some embodiments, inoculant compositions of the present disclosure comprise butin, eriodictyol, hesperetin, hesperidin, homoeriodictyol, isosakuranetin, naringenin, naringin, pinocembrin, poncirin, sakuranetin, sakuranin and/or sterubin.

In some embodiments, inoculant compositions of the present disclosure comprise one or more flavanonols. For example, in some embodiments, inoculant compositions of the present disclosure comprise dihydrokaempferol and/or taxifolin.

In some embodiments, inoculant compositions of the present disclosure comprise one or more flavans. For example, in some embodiments, inoculant compositions of the present disclosure comprise one or more flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3, 4-diols (e.g., leucocyanidin, leucodelphinidin, leucofisetinidin, leucomalvidin, luecopelargonidin, leucopeonidin, leucorobinetinidin, melacacidin and/or teracacidin) and/or dimers, trimers, oligomers and/or polymers thereof (e.g., one or more proanthocyanidins).

In some embodiments, inoculant compositions of the present disclosure comprise one or more isoflavonoids. For example, in some embodiments, inoculant compositions of the present disclosure comprise one or more isoflavones (e.g, biochanin A, daidzein, formononetin, genistein and/or glycitein), isoflavanes (e.g., equol, ionchocarpane and/or laxifloorane), isoflavandiols, isoflavenes (e.g., glabrene, haginin D and/or 2-methoxyjudaicin), coumestans (e.g., coumestrol, plicadin and/or wedelolactone), pterocarpans and/or roetonoids.

Inoculant compositions of the present disclosure may comprise any suitable flavonoid derivative, including, but not limited to, neoflavonoids (e.g, calophyllolide, coutareagenin, dalbergichromene, dalbergin, nivetin) and pterocarpans (e.g., bitucarpin A, bitucarpin B, erybraedin A, erybraedin B, erythrabyssin II, erthyrabissin-1, erycristagallin, glycinol, glyceollidins, glyceollins, glycyrrhizol, maackiain, medicarpin, morisianine, orientanol, phaseolin, pisatin, striatine, trifolirhizin).

Flavonoids and derivatives thereof may be incorporated into inoculant compostions of the present disclosure in any suitable form, including, but not limited to, polymorphic and crystalline forms.

Inoculant compositions of the present disclosure may comprise any suitable non-flavonoid node-gene inducer(s), including, but not limited to, jasmonic acid ([1R-[1$\alpha$,2$\beta$ (Z)]]-3-oxo-2-(pentenyl)cyclopentaneacetic acid; JA), linoleic acid ((Z,Z)-9,12-Octadecadienoic acid) and linolenic acid ((Z,Z,Z)-9,12,15-octadecatrienoic acid), as well as analogues, derivatives, hydrates, isomers, polymers, salts and solvates thereof.

Jasmonic acid and its methyl ester, methyl jasmonate (MeJA), collectively known as jasmonates, are octadecanoid-based compounds that occur naturally in some plants (e.g., wheat), fungi (e.g., Botryodiplodia theobromae, Gibberella fujikuroi), yeast (e.g., Saccharomyces cerevisiae) and bacteria (e.g., Escherichia coli). Linoleic acid and linolenic acid may be produced in the course of the biosynthesis of jasmonic acid. Jasmonates, linoleic acid and linolenic acid (and their derivatives) are reported to be inducers of nod gene expression or LCO production by rhizobacteria. See, e.g., Mabood, et al. PLANT PHYSIOL. BIOCHEM. 44(11):759 (2006); Mabood et al., AGR. J. 98(2):289 (2006); Mabood, et al., FIELD CROPS RES.95(2-3):412 (2006); Mabood & Smith, Linoleic and linolenic acid induce the expression of nod genes in Bradyrhizobium japonicum USDA 3, PLANT BIOL. (2001).

Useful derivatives of jasmonic acid, linoleic acid, linolenic acid that may be useful in compositions of the present disclosure include esters, amides, glycosides and salts. Representative esters are compounds in which the carboxyl group of linoleic acid, linolenic acid, or jasmonic acid has been replaced with a —COR group, where R is an —OR$^1$ group, in which R$^1$ is: an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of linoleic acid, linolenic acid, or jasmonic acid has been replaced with a —COR group, where R is an NR$^2$R$^3$ group, in which R$^2$ and R$^3$ are independently: hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of linoleic acid, linolenic acid and jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of *linoleic* acid, linolenic acid, or jasmonic acid with a solution of the base. The salts may be precipitated from solution and be collected by filtration or may be recovered by other means such as by evaporation of the solvent.

Inoculant compositions of the present disclosure may comprise karrakin(s), including, but not limited to, 2H-furo [2,3-c]pyran-2-ones, as well as analogues, derivatives, hydrates, isomers, polymers, salts and solvates thereof. In some embodiments, the inoculant composition comprises one or more karrakins represented by formula XXXX of International Patent Application No. PCT/US2016/050529 in which Z is O, S or NR$_5$; R$_1$, R$_2$, R$_3$ and R$_4$ are each independently H, alkyl, alkenyl, alkynyl, phenyl, benzyl, hydroxy, hydroxyalkyl, alkoxy, phenyloxy, benzyloxy, CN, COR$_6$, COOR═, halogen, NR$_6$R$_7$, or NO$_2$; and R$_5$, R$_6$ and R$_7$ are each independently H, alkyl or alkenyl, or a biologically acceptable salt thereof. Non-limiting examples of biologically acceptable salts of karrakins may include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Examples of compounds embraced by formula XXXX and which may be suitable for use in the present disclosure include 3-methyl-2H-furo[2,3-c]pyran-2-one (where R$_1$═CH$_3$, R$_2$, R$_3$, R$_4$═H), 2H-furo[2,3-c]pyran-2-one (where R$_1$, R$_2$, R$_3$, R$_4$═H), 7-methyl-2H-furo[2,3-c] pyran-2-one (where R$_1$, R$_2$, R$_4$═H, R$_3$═CH$_3$), 5-methyl-2H-furo[2,3-c]pyran-2-one (where R$_1$, R$_2$, R$_3$═H, R$_4$═CH$_3$), 3,7-dimethyl-2H-furo[2,3-c]pyran-2-one (where R$_1$, R$_3$═CH$_3$, R$_2$, R$_4$═H), 3,5-dimethyl-2H-furo[2,3-c] pyran-2-one (where R$_1$, R$_4$═CH$_3$, R$_2$, R$_3$═H), 3,5,7-trimethyl-2H-furo[2,3-c]pyran-2-one (where R$_1$, R$_3$, R$_4$═CH$_3$, R$_2$═H), 5-methoxymethyl-3-methyl-2H-furo[2,3-c]pyran-2-one (where R$_1$═CH$_3$, R$_2$, R$_3$═H, R$_4$═CH$_2$OCH$_3$), 4-bromo-3,7-dimethyl-2H-furo[2,3-c]pyran-2-one (where R$_1$, R$_3$═CH$_3$, R$_2$═Br, R$_4$═H), 3-methylfuro[2,3-c]pyridin-2(3H)-one (where Z═NH, R$_1$═CH$_3$, R$_2$, R$_3$, R$_4$═H) and 3,6-dimethylfuro[2,3-c]pyridin-2(6H)-one (where Z═N—CH$_3$, R$_1$═CH$_3$, R$_2$, R$_3$, R$_4$═H). See, e.g., U.S. Pat. No. 7,576,213; Halford, Smoke Signals, in CHEM. ENG. NEWS (Apr. 12, 2010) (reporting that karrikins or butenolides contained in smoke act as growth stimulants and spur seed germination after a forest fire and can invigorate seeds such as corn, tomatoes, lettuce and onions that had been stored).

Inoculant compositions of the present disclosure may comprise gluconolactone and/or one or more analogues, derivatives, hydrates, isomers, polymers, salts and/or solvates thereof.

Inoculant compositions of the present disclosure may comprise any suitable excipient(s), including, but not limited to, anti-freezing agents, drying agents, safeners and pH bufferss.

Inoculant compositions of the present disclosure may comprise any suitable agriculturally acceptable anti-freezing agent(s), including, but not limited to, ethylene glycol, glycerin, propylene glycol and urea.

Inoculant compositions of the present disclosure may comprise any suitable agriculturally acceptable drying agent(s), including, but not limited to, drying powders. For example, in some embodiments, inoculant compositions of the present disclosure comprise calcium stearate, clay (e.g., attapulgite clay, montmorillonite clay), graphite, magnesium stearate, magnesium sulfate, powdered milk, silica (e.g., fumed silica, hydrophobically-coated silica, precipitated silica), soy lecithin and/or talc. Non-limiting examples of drying agents that may be useful in compositions of the present disclosure include AEROSIL® hydrophobic fumed silica powders (Evonik Corporation, Parsippany, NJ), BEN-TOLITE® powders (BYK-Chemie GmbH, Wesel, Germany), SIPERNAT® silica powders (Evonik Corporation, Parsippany, NJ) and combinations thereof. Additional examples of drying agents that may be included in inoculant compositions of the present disclosure may be found in BURGES, FORMULATION OF MICROBIAL BIOPESTI-CIDES: BENEFICIAL MICROORGANISMS, NEMA-TODES AND SEED TREATMENTS (Springer Science & Business Media) (2012).

Inoculant compositions of the present disclosure may comprise any seed flowability agent to improve the lubricity of the treated seeds. The flowability agent may comprise one or more liquid lubricants, solid lubricants, liquid emulsions, or suspensions of solid lubricants. Non-limiting examples of flowability agents include, for example, lubricants such as fats and oils, natural and synthetic waxes, graphite, talc, fluoropolymers (e.g., polytetrafluoroethylene), and solid lubricants such as molybdenum disulfide and tungsten disulfide. In some instances, the flowability agent comprises a wax material. Non-limiting examples of wax materials that can be incorporated into the liquid seed treatment composition include plant and animal-derived waxes such as carnauba wax, candelilla wax, ouricury wax, beeswax, spermaceti, and petroleum derived waxes, such as paraffin wax. For example, in some instances, the flowability agent comprises carnauba wax. In some instances, the flowability agent comprises an oil. For example, the flowability agent may comprise soybean oil. Non-limiting examples of commercially available wax materials suitable for use as flowability agents include AQUAKLEAN 418 supplied by Micro Powders, Inc. (an anionic aqueous emulsion comprising extra light carnauba wax at 35% solids content).

Inoculant compositions of the present disclosure may comprise any suitable safener(s), including, but not limited to, napthalic anhydride.

Inoculant compositions of the present disclosure may comprise any suitable pH buffer(s), including, but not limited to, potassium phosphate monobasic and potassium phosphate dibasic.

Inoculant compositions of the present disclosure may comprise any suitable adhesive(s), including, but not limited to, adhesive compositions comprising one or more maltodextrins and/or one or more mono-, di- or oligosaccharides. Inoculant compositions of the present disclosure may be formulated into any suitable type of composition, including, but not limited to, seed coatings, soil inoculants and foliar inoculants.

Inoculant compositions of the present disclosure may comprise any suitable anti-settling agent(s), including, but not limited to, polyvinyl acetate, polyvinyl alcohols with different degrees of hydrolysis, polyvinylpyrrolidones, polyacrylates, acrylate-, polyol- or polyester-based paint system binders which are soluble or dispersible in water, moreover copolymers of two or more monomers such as acrylic acid, methacrylic acid, itaconic acid, maleic acid, fumaric acid, maleic anhydride, vinylpyrrolidone, ethylenically unsaturated monomers such as ethylene, butadiene, isoprene, chloroprene, styrene, divinylbenzene, ot-methylstyrene or p-methylstyrene, further vinyl halides such as vinyl chloride and vinylidene chloride, additionally vinyl esters such as vinyl acetate, vinyl propionate or vinyl stearate, moreover vinyl methyl ketone or esters of acrylic acid or methacrylic acid with monohydric alcohols or polyols such as methyl acrylate, methyl methacrylate, ethyl acrylate, ethylene methacrylate, lauryl acrylate, lauryl methacrylate, decyl acrylate, N,N-dimethylamino-ethyl methacrylate, 2-hydroxyethyl methacrylate, 2-hydroxypropyl methacrylate or glycidyl methacrylate, furthermore diethyl esters or monoesters of unsaturated dicarboxylic acids, furthermore (meth)acrylamido-N-methylol methyl ether, amides or nitriles such as acrylamide, methacrylamide, N-methylol(meth)acrylamide, acrylonitrile, methacrylonitrile, and also N-substituted maleiraides and ethers such as vinyl butyl ether, vinyl isobutyl ether or vinyl phenyl ether, and combinations thereof.

Biostimulants, microbial extracts, nutrients, pest attractants and/or feeding stimulants, pesticides, plant signal molecules, disperants, drying agents, anti-freezing agents, safeners, flowability agents, anti-settling agents, buffers, etc. may be incorporated into inoculant compositions of the present disclosure in any suitable amount(s)/concentration(s). The absolute value of the amount/concentration that is/are sufficient to cause the desired effect(s) may be affected by factors such as the type, size and volume of material to which the compositon will be applied, the type(s) of microorganisms in the composition, the number of microorganisms in the composition, the stability of the microorganism(s) in the composition and storage conditions (e.g., temperature, relative humidity, duration). Those skilled in the art will understand how to select effective amounts/concentrations using routine dose-response experiments. Guidance for the selection of appropriate amounts/concentrations can be found, for example, in International Patent Application Nos. PCT/US2016/050529 and PCT/US2016/050647.

In some embodiments, inoculant compositions of the present disclosure comprise one or more biostimulants in an amount/concentration of about 0.0001 to about 5% or more (by weight) of the inoculant composition. In some embodiments, the biostimulant(s) (e.g., glycine and/or seaweed extract) comprise(s) about about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more biostimulants (e.g., glycine and/or seaweed extract).

In some embodiments, inoculant compositions of the present disclosure comprise one or more microbial extracts in an amount/concentration of about 0.0001 to about 5% or more (by weight) of the inoculant composition. In some embodiments, the microbial extract(s) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more microbial extracts.

In some embodiments, inoculant compositions of the present disclosure comprise one or more nutrients in an amount/concentration of about 0.0001 to about 5% or more (by weight) of the inoculant composition. In some embodiments, the nutrient(s) (e.g., phosphorous, boron, chlorine, copper, iron, manganese, molybdenum and/or zinc) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more the nutrients (e.g., phosphorous, boron, chlorine, copper, iron, manganese, molybdenum and/or zinc).

In some embodiments, inoculant compositions of the present disclosure comprise one or more pest attractant(s) and/or feeding stimulant(s) in an amount/concentration of about 0.0001 to about 5% or more (by weight) of the inoculant composition. In some embodiments, the pest attractant(s) and/or feeding stimulant(s) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more pest attractants and/or feeding stimulants.

In some embodiments, inoculant compositions of the present disclosure comprise one or more LCOs at a concentration of about $1\times10^{-15}$ M to about $1\times10^{-10}$ M, about $1\times10^{-14}$ M to about $1\times10^{-8}$ M, about $1\times10^{-14}$ M to about $1\times10^{-6}$ M, about $1\times10^{-12}$ M to about $1\times10^{-8}$ M, about $1\times10^{-12}$ M to about $1\times10^{-6}$ M, about $1\times10^{-10}$ M to about $1\times10^{-6}$ M, or about $1\times10^{-8}$ M to about $1\times10^{-2}$ M. For example, inoculant compositions of the present disclosure may comprise about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more of one or more LCOs (e.g., one, two, three, four or more of the LCOs set forth in International Patent Application No. PCT/US2016/050529). In some embodiments, one or more LCOs comprise(s) about 0.0001 to about 5% or more (by weight) of the composition. For example, inoculant compositions of the present disclosure may comprise about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% or more of one or more LCOs. In some embodiments, the amount/concentration of LCO(s) is about 0.005 to about 2% (by weight) of the composition.

In some embodiments, inoculant compositions of the present disclosure comprise one or more COs at a concentration of about $1\times10^{-15}$ M to about $1\times10^{-10}$ M, about $1\times10^{-14}$ M to about $1\times10^{-8}$ M, about $1\times10^{-14}$ M to about $1\times10^{-6}$ M, about $1\times10^{-12}$ M to about $1\times10^{-8}$ M, about $1\times10^{-12}$ M to about $1\times10^{-6}$ M, about $1\times10^{-10}$ M to about $1\times10^{-6}$ M, or about $1\times10^{-8}$ M to about $1\times10^{-2}$ M. For example, inoculant compositions of the present disclosure may comprise about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more of one or more COs (e.g., one, two, three, four or more of the COs set forth in International Patent Application No. PCT/US2016/050529). In some embodiments, one or more COs comprise(s) about 0.0001 to about 5% or more (by weight) of the composition. For example, inoculant compositions of the present disclosure may comprise about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% or more of one or more COs. In some embodiments, the amount/concentration of CO(s) is about 0.005 to about 2% (by weight) of the composition.

In some embodiments, inoculant compositions of the present disclosure comprise one or more chitins at a concentration of about $1\times10^{-15}$ M to about $1\times10^{-10}$ M, about $1\times10^{-14}$ M to about $1\times10^{-8}$ M, about $1\times10^{-14}$ M to about $1\times10^{-6}$ M, about $1\times10^{-12}$ M to about $1\times10^{-8}$ M, about $1\times10^{-12}$ M to about $1\times10^{-6}$ M, about $1\times10^{-10}$ M to about $1\times10^{-6}$ M, or about $1\times10^{-8}$ M to about $1\times10^{-2}$ M. For example, inoculant compositions of the present disclosure may comprise about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more of one or more chitins. In some embodiments, one or more chitins comprise(s) about 0.0001 to about 5% or more (by weight) of the composition. For example, inoculant compositions of the present disclosure may comprise about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% or more of one or more chitins. In some embodiments, the amount/concentration of chitin(s) is about 0.005 to about 2% (by weight) of the composition.

In some embodiments, inoculant compositions of the present disclosure comprise one or more chitosans at a concentration of about $1\times10^{-15}$ M to about $1\times10^{-10}$ M, about $1\times10^{-14}$ M to about $1\times10^{-8}$ M, about $1\times10^{-14}$ M to about $1\times10^{-6}$ M, about $1\times10^{-12}$ M to about $1\times10^{-8}$ M, about $1\times10^{-12}$ M to about $1\times10^{-6}$ M, about $1\times10^{-10}$ M to about $1\times10^{-6}$ M, or about $1\times10^{-8}$ M to about $1\times10^{-2}$ M. For example, inoculant compositions of the present disclosure may comprise about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more of one or more chitosans. In some embodiments, one or more chitosans comprise(s) about 0.0001 to about 5% or more (by weight) of the composition. For example, inoculant compositions of the present disclosure may comprise about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% or more of one or more chitosans. In some embodiments, the amount/concentration of chitosan(s) is about 0.005 to about 2% (by weight) of the composition.

In some embodiments, the inoculant compositions of the present disclosure comprise one or more flavonoids at a concentration of about $1\times10^{-20}$ M to about $1\times10^{-1}$ M. For example, inoculant compositions of the present disclosure may comprise one or more flavonoids at a concentration of about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M. In some embodiments, the flavonoid concentration is $1\times10^{-14}$ M to $1\times10^{-5}$ M, $1\times10^{-12}$ M to $1\times10^{-6}$ M, or $1\times10^{-10}$ M to $1\times10^{-M}$. In some embodiments, one or more flavonoids comprise(s) about 0.0001 to about 5% or more (by weight) of the composition. For example, inoculant compositions of the present disclosure may comprise about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% or more of one or more flavonoids. In some embodiments, the amount/concentration of flavonoid(s) is about 0.005 to about 2% (by weight) of the composition.

In some embodiments, inoculant compositions of the present disclosure comprise one or more dispersants in an amount/concentration of about 0.001 to about 25% or more (by weight) of the inoculant composition. In some embodiments, the dispersant(s) comprise(s) 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9 or 10 to about 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20% or more (by weight) of one or more dispersants (e.g., one or more surfactants and/or wetting agents).

In some embodiments, inoculant compositions of the present disclosure comprise one or more drying agents in an amount/concentration of about 0.001 to about 95% or more (by weight) of the inoculant composition. In some embodiments, the drying agent(s) comprise(s) about) 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9 or 10 to about 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more drying agents (e.g., lecithin and/or talc).

In some embodiments, the inoculant compositions of the present disclosure comprise about 0.5 to about 10 grams of drying powder per liter of inoculant composition. For example, inoculant compositions of the present disclosure may comprise about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 grams or more of drying powder per liter of inoculant composition.

In some embodiments, In some embodiments, inoculant compositions of the present disclosure comprise one or more abti-settling agents in an amount/concentration of about 0.0001 to about 10% or more (by weight) of the composition. For example, inoculant compositions of the present disclosure may comprise about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 5.5, 6, 6.5, 7, 7.5, 8, 8.5, 9, 9.5, 10% or more of one or more anti-settling agents. In some embodiments, the amount/concentration of anti-settling agents is about 0.01 to about 5% (by weight) of the composition.

In some embodiments, inoculant compositions of the present disclosure comprise one or more buffers in an amount/concentration of about 0.0001 to about 5% or more (by weight) of the inoculant composition. In some embodiments, the buffer(s) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% (by weight) of the inoculant composition.

For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of one or more buffers (e.g., potassium phosphate monobasic and/or potassium phosphate dibasic).

In some embodiments, inoculant compositions of the present disclosure comprise one or more commercial carriers, antioxidants, oxygen scavengers, hygroscopic polymers, UV protectants, biostimulants, microbial extracts, nutrients, pest attractants and/or feeding stimulants, pesticides, plant signal molecules, disperants, drying agents, anti-freezing agents, safeners, flowability agents, anti-settling agents, buffers and/or adhesives used in accordance with the manufacturer's recommended amounts/concentrations.

In some embodiments, inoculant compositions of the present disclosure are formulated as aqueous formulations in which at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of the microbial spores and/or vegetative cells in the inoculant composition remain viable following:

> storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

> desiccation by about 5, 10, 15, 20, 25, 30, 35, 40, 45, 50, 55, 60, 65, 70, 75, 80, 85, 90, 95% or more;

> desiccation by about 5, 10, 15, 20, 25, 30, 35, 40, 45, 50, 55, 60, 65, 70, 75, 80, 85, 90, 95% or more and > storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

> cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

> application to plant propagation material (optionally, seed);

> application to plant propagation material and desiccation by about 5, 10, 15, 20, 25, 30, 35, 40, 45, 50, 55, 60, 65, 70, 75, 80, 85, 90, 95% or more;

> application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; foliar application;

foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, inoculant compositions of the present disclosure are formulated as aqueous formulations in which at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$ or more colony-forming units per gram and/or milliliter of inoculant composition remain viable following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application to plant propagation material (optionally, seed);

application to plant propagation material and desiccation by about 5, 10, 15, 20, 25, 30, 35, 40, 45, 50, 55, 60, 65, 70, 75, 80, 85, 90, 95% or more;

application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

foliar application;

foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, inoculant compositions of the present disclosure improve both the survival rate and one, two, three, four, five, six, seven, eight, nine, ten or more microbial stability characteristics of the microbial spores and/or vegetative cells contained therein.

In some embodiments, inoculant compositions of the present disclosure improve the dispersion of microbial spores and/or vegetative cells contained therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure). For example, inoculant compositions of the present disclosure may improve the dispersion of one or more of the microbial spores and/or vegetative cells contained therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the protectants/dispersants found in the inoculant composition and/or comprises a reduced amount/concentration of one or more of the protectants/dispersants found in the inoculant composition.

In some embodiments, inoculant compositions of the present disclosure improve the dispersion of one or more of the microbial spores and/or vegetative cells contained therein to the extent that at least about 50, 55, 60, 65, 70, 75, 80, 85, 90, 95% or more of the microbial spores and/or vegetative cells are present as single cells/spores (rather than as members of a clump comprising two or more cells/spores).

In some embodiments, inoculant compositions of the present disclosure exhibit enhanced flowability as compared to a control composition (e.g., a control composition that is identical to the inoculant composition of the present disclosure except that it lacks one or more of the components found in the inoculant composition and/or contains one or more components not found in the inoculant composition of the present disclosure). For example, the flowability of inoculant compositions of the present disclosure may be improved by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the protectants/dispersants found in the inoculant composition and/or comprises a reduced amount/concentration of one or more of the protectants/dispersants found in the inoculant composition.

In some embodiments, inoculant compositions of the present disclosure are formulated as amorphous liquids.

In some embodiments, inoculant compositions of the present disclosure comprise less than 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5% water by weight, based upon the total weight of the composition.

In some embodiments, inoculant compositions of the present disclosure have a pH of about 4.5 to about 9.5. In some embodiments, inoculant compositions of the present disclosure have a pH of about 6 to about 7.5. In some embodiments, inoculant compositions of the present disclosure have a pH of about 5, 5.5, 6, 6.5, 7, 7.5, 8 or 8.5.

As noted above, inoculant compositions of the present disclosure may comprise agriculturally beneficial constituents, such as biostimulants, microbial extracts, nutrients, pesticides and plant signal molecules. It is to be understood that agriculturally beneficial constituents may also be used in conjunction with inoculant compositions of the present disclosure. Thus, the present disclosure extends to systems and methods of using inoculant compositions of the present disclosure in conjunction with compositions comprising one or more agriculturally beneficial constituents (e.g., a second composition comprising one or more LCOs and/or COs, a third composition comprising one or more fungicides, herbicides, insectides and/or netamicides, etc.).

Inoculant compositions of the present disclosure may be formulated for the treatment of any suitable plant type, including, but not limited to, row crops and vegetables. In some embodiments, inoculant compositions of the present disclosure are formulated for the treatment of one or more plants selected from Amaranthaceae (e.g., chard, spinach, sugar beet, *quinoa*), Asteraceae (e.g., artichoke, asters, chamomile, chicory, chrysanthemums, dahlias, daisies, *echinacea*, goldenrod, guayule, lettuce, marigolds, safflower, sunflowers, zinnias), Brassicaceae (e.g., arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, *Arabidopsis thaliana*), Cucurbitaceae (e.g., cantaloupe, cucumber, honeydew, melon, pumpkin, squash (e.g., acorn squash, butternut squash, summer squash), watermelon, zucchini), Fabaceae (e.g., alfalfa, beans, carob, clover, guar, lentils, mesquite, peas, peanuts, soybeans, tamarind, tragacanth, vetch), Malvaceae (e.g., cacao, cotton, durian, hibiscus, kenaf, kola, okra), Poaceae (e.g., bamboo, barley, corn, fonio, lawn grass (e.g., Bahia grass, Bermudagrass, bluegrass, Buffalograss, Centipede grass, Fescue, or *Zoysia*), millet, oats, ornamental grasses, rice, rye, sorghum, sugar cane, triticale, wheat), Polygonaceae (e.g., buckwheat), Rosaceae (e.g., almonds, apples, apricots, blackberry, blueberry, cherries, peaches, plums, quinces, raspberries, roses, strawberries), Solanaceae (e.g., bell peppers, chili peppers, eggplant, *petunia*, potato, tobacco, tomato) and Vitaceae (e.g., grape). In some embodiments, inoculant compositions of the present disclosure are formulated for the treatment of one or more fungicide-, herbicide-, insecticide- and/or nematicide-resistant plants (e.g., one or more plants resistant to acetolactate synthase inhibitors. Non-limiting examples of plants that may be treated with inoculant compositions of the present disclosure include plants sold by Monsanto Company (St. Louis, MO) under the BOLLGARD II®, DROUGHTGARD®, GENUITY®, RIB COMPLETE®, ROUNDUP READY®, ROUNDUP READY 2 YIELD®, ROUNDUP READY 2 EXTEND™, SMARTSTAX®, VT DOUBLE PRO®, VT TRIPLE PRO®, YIELDGARD®, YIELDGARD VT ROOTWORM/RR2®, YIELDGARD VT TRIPLE® and/or XTENDFLEX™ tradenames.

The present disclosure extends to plants that have been treated with inoculant compositions of the present disclosure, plant parts harvested from plants that have been treated with inoculant compositions of the present disclosure, processed products derived from plants that have been treated with inoculant compositions of the present disclosure and crops comprising a plurality of plants that have been treated with inoculant compositions of the present disclosure.

The present disclosure also provides coated plant propagation materials comprising, consisting essentially of, or consisting of a plant propagation material and a coating that covers at least a portion of the outer surface of the plant propagation material, said coating comprising, consisting essentially of, or consisting of an inoculant composition of the present disclosure.

The coating may comprise one, two, three, four, five or more layers. In some embodiments, the coating comprises an inner layer that contains one or more microorganisms and one or more outer layers free or substantially free of microorganisms. In some embodiments, the inner layer of the coating is an inoculant composition of the present disclosure and the outer layer is equivalent to an inoculant composition of the present disclosure but it lacks one or more microorganisms. For example, coated plant propagation materials of the present disclosure may comprise a seed that is coated with an inner layer that comprises microbial spores (e.g., spores of one or more strains of *Bacillus*, one or more strains of *Gliocladium*, one or more strains of *Glomus*, one or more strains of *Metarhizium*, one or more strains of *Penicillium* and/or one or more strains of *Trichoderma*), one or more protectants, one or more dispersants and one or more aqueous additives in a non-aqueous carrier and an outer layer that comprises the same carrier but is free of microbial spores. In some embodiments, the coating comprises, consists essentially of, or consists of an inoculant composition of the present disclosure and a drying powder. For example, coated plant propagation materials of the present disclosure may comprise a seed that is coated with an inoculant composition comprising microbial spores (e.g., spores of one or more strains of *Bacillus*, one or more strains of *Gliocladium*, one or more strains of *Glomus*, one or more strains of *Metarhizium*, one or more strains of *Penicillium* and/or one or more strains of *Trichoderma*), one or more protectants, one or more dispersants and one or more aqueous additives in a non-aqueous carrier and is then covered with a drying powder (e.g., a drying power that comprises calcium stearate, one or more clays, graphite, magnesium stearate, magnesium sulfate, powdered milk, silica, soy lecithin and/or talc).

Inoculant compositions of the present disclosure may be coated on plant propagation materials in any suitable amount(s)/concentration(s). In some embodiments, the inoculant composition is applied in an amount ranging from about 0.5 to about 1000 milliliters of inoculant composition per kilogram of plant propagation material. For example, in some embodiments, about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90, 100, 150, 200, 250, 300, 350, 400, 450, 500 milliliters or more of inoculant composition is applied per kilogram of seed. In some embodiments, an inoculant composition comprising one or more protectants and one or more microbial spores (e.g., spores of one or more strains of *Bacillus*, one or more strains of *Gliocladium*, one or more strains of *Glomus*, one or more strains of *Metarhizium*, one or more strains of *Penicillium* and/or one or more strains of *Trichoderma*) is applied at a rate of about 2, 2.25, 2.5, 2.75, 3, 3.25, 3.5, 3.75, or 4 milliliters per kilogram of seed.

Drying powders may be applied in any suitable amount(s)/concentration(s). In some embodiments, the drying powder is applied in an amount ranging from about 0.5 to about 10 grams of drying powder per kilogram of plant propagation material. For example, in some embodiments, about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 grams or more of drying powder (e.g., drying powder comprising magnesium stearate, magnesium sulfate, powdered milk, silica, soy lecithin and/or talc) is applied per kilogram of seed. In some embodiments, a drying powder comprising calcium stearate, attapulgite clay, montmorillonite clay, graphite, magnesium stearate, silica (e.g., fumed silica, hydrophobically-coated silica and/or precipitated silica) and/or talc is applied to seeds coated with an inoculant composition comprising one or more maltodextrins (e.g., one or more maltodextrins having a DEV of about 15 to about 20) and one or more microbial spores (e.g., spores of one or more strains of *Bacillus*, one or more strains of *Gliocladium*, one or more strains of *Glomus*, one or more strains of *Metarhizium*, one or more strains of *Penicillium* and/or one or more strains of *Trichoderma*) at a rate of about 1, 1.25, 1.5, 1.75, 2, 2.25, 2.5, 2.75, or 3 grams per kilogram of seed.

In some embodiments, the coating covers about 50, 55, 60, 65, 70, 75, 80, 85, 90, 95, 96, 97, 98, 99, 99.5% or more of the outer surface of the plant propagation material.

In some embodiments, the average thickness of the coating is at least 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5 μm or more. In some embodiments, the average thickness of the coating is about 1.5 to about 3.0 μm.

In some embodiments, the coating comprises one or more effect pigments. Effect pigments, which are sometimes also referred to in the art as "pearl pigments," are a class of materials that provide reflectivity, shine, and/or a pearlescent effect when applied as a coating. In some instances, the effect pigment is in the form of a powder comprising a substrate material and a metal oxide coating. For example, the effect pigment may comprise a substrate material including but not limited to talc, silicate materials (e.g., mica), clay minerals, calcium carbonate, kaolin, phlogopite, alumina, and similar substances. In some instances, the substrate material comprises a hydrophilic material. The substrate material may be coated with a semi-transparent layer of a metal oxide, including but not limited to titanium dioxide, iron oxide, chromium oxide, or zirconium oxide. Alternatively, in some instances, the effect pigment comprises metal powder or metal flakes. The metal powder or metal flakes may comprise a metal including, but not limited to aluminum, copper, silver, or bronze. In some instances, the effect pigment comprises a silicate based substrate. Non-limiting examples of particulate silicates that can be incorporated into the dry powder coating include mica coated with titanium dioxide (e.g., SUNMICA FINE WHITE 2800102, which is commercially available from Sun Chemical Corp.). Other non-limiting examples of commercially available effect pigments that can be incorporated into the dry powder include MAGNA PEARL, LUMINA and MEARLIN pigments from BASF Corporation; PHIBRO PEARL from PhibroChem; and IRIDESIUM 120 from Aakash Chemicals. In some instances, the dry powder has a mean particle size of from about 1 to about 25 microns.

Inoculant compositions of the present disclosure may be used to coat any suitable plant propagation materials, including, but not limited to, cuttings (e.g., leaves, stems), rhizomes, seeds and tubers. In some embodiments, the plant propagation material is a seed.

Inoculant compositions of the present disclosure may be used to coat plant propagation materials of any suitable plant type, including, but not limited to, row crops and vegetables. In some embodiments, inoculant compositions of the present disclosure are coated on propagation material derived from one or more plants selected from Amaranthaceae (e.g., chard, spinach, sugar beet, *quinoa*), Asteraceae (e.g., artichoke, asters, chamomile, chicory, chrysanthemums, dahlias, daisies, *echinacea*, goldenrod, guayule, lettuce, marigolds, safflower, sunflowers, zinnias), Brassicaceae (e.g., arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, *Arabidopsis thaliana*), Cucurbitaceae (e.g., cantaloupe, cucumber, honeydew, melon, pumpkin, squash (e.g., acorn squash, butternut squash, summer squash), watermelon, zucchini), Fabaceae (e.g., alfalfa, beans, carob, clover, guar, lentils, mesquite, peas, peanuts, soybeans, tamarind, tragacanth, vetch), Malvaceae (e.g., cacao, cotton, durian, hibiscus, kenaf, kola, okra), Poaceae (e.g., bamboo, barley, corn, fonio, lawn grass (e.g., Bahia grass, Bermudagrass, bluegrass, Buffalograss, Centipede grass, Fescue, or *Zoysia*), millet, oats, ornamental grasses, rice, rye, sorghum, sugar cane, triticale, wheat), Polygonaceae (e.g., buckwheat), Rosaceae (e.g., almonds, apples, apricots, blackberry, blueberry, cherries, peaches, plums, quinces, raspberries, roses, strawberries), Solanaceae (e.g., bell peppers, chili peppers, eggplant, *petunia*, potato, tobacco, tomato) and Vitaceae (e.g., grape). Non-limiting examples of plant propagation materials that may be coated with inoculant compositions of the present disclosure include seeds sold by Monsanto Company (St. Louis, MO) under the BOLLGARD II®, DROUGHTGARD®, GENUITY®, RIB COMPLETE®, ROUNDUP READY®, ROUNDUP READY 2 YIELD®, ROUNDUP READY 2 EXTEND™, SMARTSTAX®, VT DOUBLE PRO®, VT TRIPLE PRO®, YIELDGARD®, YIELDGARD VT ROOTWORM/RR2®, YIELDGARD VT TRIPLE® and/or XTENDFLEX™ tradenames.

The present disclosure extends to plants that grow from coated plant propagation materials of the present disclosure, plant parts harvested from plants that grow from coated plant propagation materials of the present disclosure, processed products derived from plants that grow from coated plant propagation materials of the present disclosure and crops comprising a plurality of plants that grow from coated plant propagation materials of the present disclosure.

The present disclosure also provides kits comprising, consisting essentially of, or consisting of a coated plant propagation material of the present disclosure and a container housing the coated plant propagation material. In some embodiments, the kit further comprises one or more oxygen scavengers, such as activated carbon, ascorbic acid, iron powder, mixtures of ferrous carbonate and metal halide catalysts, sodium chloride and/or sodium hydrogen carbonate.

The container may comprise any suitable material(s), including, but not limited to, materials that reduce the amount of light, moisture and/or oxygen that contact the coated plant propagation material when the container is sealed.

In some embodiments, the container comprises, consists essentially of, or consists of a material having light permeability of less than about 1, 2, 3, 4, 5, 6, 7, 8, 9, 10, 15, 20, 25, 30, 35, 40, 45, 50, 55, 60, 65, 70 or 75%.

In some embodiments, the container reduces the amount of ambient light that reaches said coated plant propagation material by about 5, 10, 15, 20, 25, 30, 35, 40, 45, 50, 55, 60, 65, 70, 75, 80, 85, 90, 95 or 100% when sealed.

In some embodiments, the container reduces the amount of ambient moisture that reaches said plant propagation material by about 5, 10, 15, 20, 25, 30, 35, 40, 45, 50, 55, 60, 65, 70, 75, 80, 85, 90, 95 or 100% when sealed.

In some embodiments, the container comprises, consists essentially of, or consists of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 cm$^3$/m$^2$·day (as measured in accordance with ASTM D3985).

In some embodiments, the container reduces the amount of ambient oxygen that reaches said plant propagation material by about 5, 10, 15, 20, 25, 30, 35, 40, 45, 50, 55, 60, 65, 70, 75, 80, 85, 90, 95 or 100% when sealed.

In some embodiments, kits of the present disclosure comprise 1, 2, 3, 4, 5 or more additional containers. The additional containers may comprise any suitable component(s) or composition(s), including, but not limited to, agriculturally beneficial microorganisms, biostimulants, drying agents, nutrients, oxidation control components and pesticides. Examples of agriculturally beneficial microorganisms, biostimulants, drying agents, nutrients, oxidation control components and pesticides that may be included in the additional containers are described above.

The present disclosure also provides animal feed compositions comprising, consisting essentially of, or consisting of a food component and a microbial component, said microbial component comprising, consisting essentially of, or consisting of an inoculant composition of the present disclosure.

Animal feed compositions of the present disclosure may comprise any suitable food component, including, but not limited to, fodder (e.g., grains, hay, legumes, silage and/or straw) and forage (e.g., grass).

Animal feed compositions of the present disclosure may be fed to any suitable animal, including, but not limited to, farm animals, zoo animals, laboratory animals and/or companion animals. In some embodiments, the animal feed composition is formulated to meet the dietary needs of birds (e.g., chickens, ducks, quails and/or turkeys), bovids (e.g., antelopes, bison, cattle, gazelles, goats, impala, oxen, sheep and/or wildebeests), canines, cervids (e.g., caribou, deer, elk and/or moose), equines (e.g., donkeys, horses and/or zebras), felines, fish, pigs, rabbits, rodents (e.g., guinea pigs, hamsters, mice and/or rats) and the like.

The present disclosure also provides methods comprising, consisting essentially of, or consisting of applying an inoculant composition of the present disclosure to a plant or plant part.

Inoculant compositions of the present disclosure may be applied in any suitable manner, including, but not limited to, on-seed application, in-furrow application and foliar application.

In some embodiments, inoculant compositions of the present disclosure are applied to plant propagation materials (e.g., seeds) at least 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more prior to planting.

In some embodiments, inoculant compositions of the present disclosure are applied to plant propagation materials (e.g., seeds) at the time of planting.

Plant propagation materials may be treated using any suitable method(s), including, but not limited to, coating, dripping, spraying and soaking. Batch systems, in which predetermined batch sizes of material and inoculant composition are delivered into a mixer, may be employed. Continuous treatment systems, which are calibrated to apply inoculant composition at a predefined rate in proportion to a continuous flow of material, may also be employed.

In some embodiments, plant propagation materials are soaked for at least 0.1, 0.2, 0.3, 0.4, 0.5, 0.6, 0.7, 0.8, 0.9, 1, 1.25, 1.5, 1.75, 2, 3, 4, 5, 6, 9, 12, 15, 18, 21, 24, 36, 48 hours or more in an inoculant composition of the present disclosure.

In some embodiments, plant propagation materials (e.g., seeds) are coated by applying an inoculant composition of the present disclosure to the inside wall of a round container, adding the seeds, then rotating the container such that the seeds come into contact with the composition, a process known in the art as "container coating".

In some embodiments, an inoculant composition of the present disclosure is freeze-spray- or spray-freeze-dried and then applied to plant propagation material. For examples, in some embodiments, an inoculant composition comprising one or more maltodextrins (e.g., one or more maltodextrins having a DEV of about 15 to about 20), one or more microbial spores (e.g., spores of one or more strains of *Bacillus*, one or more strains of *Gliocladium*, one or more strains of *Glomus*, one or more strains of *Metarhizium*, one or more strains of *Penicillium* and/or one or more strains of *Trichoderma*) and one or more disaccharides (e.g., maltose) is freeze-spray- or spray-freeze-dried, mixed with a drying powder (e.g., a drying powder comprising calcium stearate, attapulgite clay, montmorillonite clay, graphite, magnesium stearate, silica (e.g., fumed silica, hydrophobically-coated silica and/or precipitated silica) and/or talc), then coated on seed that was been pre-treated with one or more adhesives (e.g., an adhesive composition comprising one or more maltodextrins, one or more mono-, di- or oligosaccharides, one or more peptones, etc.), one or more pesticides and/or one or more plant signal molecules (e.g., one or more LCOs).

The present disclosure also provides methods comprising, consisting essentially of, or consisting of planting a coated seed of the present disclosure.

The present disclosure also provides methods of enhancing the survival and/or stability of microbial spores in a composition, said methods comprising, consisting essentially of, or consisting of adding an effective amount of one or more protectants to said composition.

Protectants may be used to improve any suitable microbial stability characteristic(s) of the microbial spores in a composition, including, but not limited to, the ability of the microbial spores in a composition to enhance plant yield after being coated on a seed and stored for a defined period of time prior to planting the seed. For example, the addition of one or more protectants to a composition enhances the ability of the microbial spores therein to propagate and increase yield after being coated on a plant propagation material (e.g., seed) and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the addition of one or more protectants to a composition improves the stability of one or more microbial spores therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to microbial spores in a control composition (e.g., a control composition that is identical to the inoculant composition of the present disclosure except that it lacks one or more of the components found in the inoculant composition and/or contains one or more components not found in the inoculant composition of the present disclosure). For example, the addition of one or more protectants to a composition may improve one or more microbial stability characteristics of one or more microbial spores therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the protectants found in the inoculant composition and/or comprises a reduced amount of one or more of the protectants found in the inoculant composition.

In some embodiments, the addition of one or more protectants to a composition improves the stability of one or more microbial spores therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure). For example, the addition of one or more protectants to a composition may improve the survival rate of one or more of the microbial spores contained therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more of the protectants found in the inoculant composition and/or comprises a reduced amount of one or more of the protectants found in the inoculant composition.

In some embodiments, the addition of one or more protectants to a composition improves the survival of one or more of the microbial spores in an inoculant composition to the extent that at least at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of the microbial spores and/or vegetative cells in the inoculant composition remain viable following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application to plant propagation material (optionally, seed);

application to plant propagation material and desiccation by about 5, 10, 15, 20, 25, 30, 35, 40, 45, 50, 55, 60, 65, 70, 75, 80, 85, 90, 95% or more;

application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

foliar application;

foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, the addition of one or more protectants to a composition improves the survival of one or more of the microbial spores in an inoculant composition to the extent that at least $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$ or more colony-forming units per gram and/or milliliter of inoculant composition remain viable following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application to plant propagation material (optionally, seed);

application to plant propagation material and desiccation by about 5, 10, 15, 20, 25, 30, 35, 40, 45, 50, 55, 60, 65, 70, 75, 80, 85, 90, 95% or more;

application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

foliar application;

foliar application and desiccation by about 5, 10, 15, 20, 25, 30, 35, 40, 45, 50, 55, 60, 65, 70, 75, 80, 85, 90, 95% or more; and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, the addition of one or more maltodextrins to a composition improves both the survival rate and one, two, three, four, five, six, seven, eight, nine, ten or more microbial stability characteristics of the microbial spore(s) contained therein.

Any suitable protectant(s) may be added to the composition, including, but not limited to monosaccharides, disaccharides, oligosaccharides, maltodextrins, sugar alcohols, humic acids, malt extracts, peat extracts, skim milk extracts, betaines, prolines, sarcosines, peptones, oxidation control components, hygroscopic polymers and UV protectants.

In some embodiments, one or more of the protectants described above with respect to inoculant compositions of the present disclosure is/are added to the composition. For example, in some embodiments, one or more monosaccharides and/or disaccharides (e.g., arabinose, fructose, glucose, maltose, sucrose and/or trehalose) and one or more sugar alcohols (e.g., arabitol, mannitol, sorbitol and/or xylitol) are added to the composition to enhance the stability and/or survival of the microbial spores therein.

Protectants may be added to the composition in any suitable amount(s)/concentration(s). The absolute value of the amount/concentration/dosage of protectant(s) sufficient to cause the desired effect may be affected by factors such as the type, size and volume of material to which the compositon will be applied, the stability of the microbial spores in the composition, the identity and amounts/concentrations of other components in the inoculant composition, and storage conditions (e.g., temperature, relative humidity, duration). Those skilled in the art will understand how to select an effective amount/concentration/dosage using routine dose-response experiments. Those skilled in the art will understand how to select an effective amount/concentration/dosage using routine dose-response experiments. Guidance for the selection of appropriate amounts/concentrations can be found, for example, in International Patent Application Nos. PCT/US2016/050529 and PCT/US2016/050647 and U.S. Provisional Patent Application Nos. 62/296,798; 62/271,857; 62/347,773; 62/343,217; 62/296,784; 62/271,873; 62/347,785; 62/347,794; 62/347,805; 62/436,517 and 62/436,529.

In some embodiments, the protectant(s) is/are added to the composition until it/they are present in an amount/concentration described above with respect to inoculant compositions of the present disclosure. For example, in some embodiments, one or more monosaccharides, disaccharides, maltodextrins, sugar alcohols and/or humic acids may be added to the composition until it/they comprise about/at least/less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 5.5, 6, 6.5, 7, 7.5, 8, 8.5, 9, 10% of the composition (by weight, based upon the total weight of the composition).

Similarly, one or more oxidation control components and/or UV protectants may be added the composition until it/they comprise about/at least/less than 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% of the composition (by weight, based upon the total weight of the composition). In some embodiments, In some embodiments, one or more monosaccharides and/or disaccharides (e.g., arabinose, fructose, glucose, maltose, sucrose and/or trehalose) and one or more sugar alcohols (e.g., arabitol, mannitol, sorbitol and/or xylitol) are added to the composition until it are present in amounts/concentrations described above with respect to inoculant compositions of the present disclosure. For example, in some embodiments, one or more monosaccharides and/or disaccharides (e.g., arabinose, fructose, glucose, maltose, sucrose and/or trehalose) and one or more sugar alcohols (e.g., arabitol, mannitol, sorbitol and/or xylitol) are added to the composition until they each/collectively comprise about/at least/less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 5.5, 6, 6.5, 7, 7.5, 8, 8.5, 9, 10% of the composition (by weight, based upon the total weight of the composition).

Protectants may be added to the composition in any suitable ratio(s). For example, in some embodiments, one or more monosaccharides and/or disaccharides (e.g., arabinose, fructose, glucose, maltose, sucrose and/or trehalose) and one or more sugar alcohols (e.g., arabitol, mannitol, sorbitol and/or xylitol) are added to the composition in a mono- and/or disaccharide:sugar alcohol ratio of about 50:50, 55:45, 60:40, 65:35, 70:30, 75:25, 80:20, 85:15, 90:10, 95:5. The present disclosure also provides systems and methods of using inoculant compositions of the present disclosure in conjunction with additional compositions comprising one or more agriculturally beneficial constituents. The additional composition(s) may comprise any suitable agriculturally beneficial constituent(s), including, but not limited to, the agriculturally beneficial constituents described above.

In some embodiments, inoculant compositions of the present disclosure are used in conjunction with one or more on-seed compositions, one or more in-furrow compositions and/or one or more foliar-applied compositions.

In some embodiments, inoculant compositions of the present disclosure are used as part of an integrated disease and/or pest management system.

Particular embodiments of the present disclosure are described in the following numbered paragraphs:

1. An aqueous inoculant composition, comprising, consisting essentially of, or consisting of: microbial spores; and a non-aqueous carrier, said inoculant composition comprising more than 0.5% water, by weight, based upon the total weight of the composition.

2. The inoculant composition of any one of the preceding paragraphs, wherein said microbial spores comprise about 0.1% to about 50% (by weight) of said inoculant composition, optionally about 5 to about 15% (by weight) of said composition, optionally about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50% (by weight) of said inoculant composition.

3. The inoculant composition of any one of the preceding paragraphs, wherein said microbial spores are present in said inoculant composition in a concentration ranging from about $1 \times 10^1$ to about $1 \times 10^{20}$ colony-forming units per gram and/or milliliter of said inoculant composition, optionally $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$ or more colony-forming units per gram and/or milliliter of said inoculant composition.

4. The inoculant composition of any one of the preceding paragraphs, wherein said microbial spores comprise, consist essentially of, or consist of spores of one or more diazotrophic microorganisms.

5. The inoculant composition of any one of the preceding paragraphs, wherein said microbial spores comprise, consist essentially of, or consist of spores of one or more strains of *Bacillus*, optionally one or more strains of *Bacillus circulans*, *Bacillus lichenmformis*, *Bacillus macerans*, *Bacillus megatarium*, *Bacillus polymyxa* and/or *Bacillus pumilus*.

6. The inoculant composition of any one of the preceding paragraphs, wherein said microbial spores comprise, consist essentially of, or consist of spores of one or more phosphate-solubilizing microorganisms.

7. The inoculant composition of any one of the preceding paragraphs, wherein said microbial spores comprise, consist essentially of, or consist of spores of one or more strains of *Penicillium*, optionally one or more strains of *P. bilaiae* and/or *P. gaestrivorus*.

8. The inoculant composition of any one of the preceding paragraphs, wherein said microbial spores comprise, consist essentially of, or consist of spores of one or more strains of *Trichoderma*, optionally one or more strains of *T. asperellum*, *T. atroviride*, *T. fertile*, *T. gamsii*, *T. hamatum*, *T. harzianum*, *T. reesi*, *T. virens* and/or *T. viridae*.

9. The inoculant composition of any one of the preceding paragraphs, wherein said microbial spores comprise, consist essentially of, or consist of spores of one or more mycorrhizal fungi.

10. The inoculant composition of any one of the preceding paragraphs, wherein said microbial spores comprise, consist essentially of, or consist of spores of one or more strains of *Gliocladium*, optionally one or more strains of *Gliocladium virens*, one or more strains of *Glomus*, optionally one or more strains of *Glomus intraradices*, and/or one or more strains of *Metarhizium*, optionally, one or more strains of *Metarhizium anisopliae*.

11. The inoculant composition of any one of the preceding paragraphs, wherein said microbial spores comprise, consist essentially of, or consist of spores of one or more strains of *Bacillus*, optionally *Bacillus amyloliquefaciens* D747, *Bacillus amyloliquefaciens* NRRL B-50349, *Bacillus amyloliquefaciens* TJ1000, *Bacillus amyloliquefaciens* FZB24, *Bacillus amyloliquefaciens* FZB42, *Bacillus amyloliquefaciens* IN937a, *Bacillus amyloliquefaciens* IT-45, *Bacillus amyloliquefaciens* TJ1000, *Bacillus amyloliquefaciens* MBI600, *Bacillus amyloliquefaciens* BS27 (deposited as NRRL B-5015), *Bacillus amyloliquefaciens* BS2084 (deposited as NRRL B-50013), *Bacillus amyloliquefaciens* 15AP4 (deposited as ATCC PTA-6507), *Bacillus amyloliquefaciens* 3AP4 (deposited as ATCC PTA-6506), *Bacillus amyloliquefaciens* LSSA01 (deposited as NRRL B-50104), *Bacillus amyloliquefaciens* ABP278 (deposited as NRRL B-50634), *Bacillus amyloliquefaciens*

1013 (deposited as NRRL B-50509), *Bacillus amyloliquefaciens* 918 (deposited as NRRL B-50508), *Bacillus amyloliquefaciens* 22CP1 (deposited as ATCC PTA-6508) and *Bacillus amyloliquefaciens* BS18 (deposited as NRRL B-50633), *Bacillus cereus* I-1562, *Bacillus firmus* I-1582, *Bacillus lichenformis* BA842 (deposited as NRRL B-50516), *Bacillus lichenformis* BL21 (deposited as NRRL B-50134), *Bacillus mycoides* NRRL B-21664, *Bacillus pumilus* NRRL B-21662, *Bacillus pumilus* NRRL B-30087, *Bacillus pumilus* ATCC 55608, *Bacillus pumilus* ATCC 55609, *Bacillus pumilus* GB34, *Bacillus pumilus* KFP9F, *Bacillus pumilus* QST 2808, *Bacillus subtilis* ATCC 55078, *Bacillus subtilis* ATCC 55079, *Bacillus subtilis* MBI600, *Bacillus subtilis* NRRL B-21661, *Bacillus subtilis* NRRL B-21665, *Bacillus subtilis* CX-9060, *Bacillus subtilis* GB03, *Bacillus subtilis* GB07, *Bacillus subtilis* QST-713, *Bacillus subtilis* FZB24, *Bacillus subtilis* D747, *Bacillus subtilis* 3BP5 (deposited as NRRL B-50510), *Bacillus thuringiensis* ATCC 13367, *Bacillus thuringiensis* GC-91, *Bacillus thuringiensis* NRRL B-21619, *Bacillus thuringiensis* ABTS-1857, *Bacillus thuringiensis* SAN 401 I, *Bacillus thuringiensis* ABG-6305, *Bacillus thuringiensis* ABG-6346, *Bacillus thuringiensis* AM65-52, *Bacillus thuringiensis* SA-12, *Bacillus thuringiensis* SB4, *Bacillus thuringiensis* ABTS-351, *Bacillus thuringiensis* HD-1, *Bacillus thuringiensis* EG 2348, *Bacillus thuringiensis* EG 7826, *Bacillus thuringiensis* EG 7841, *Bacillus thuringiensis* DSM 2803, *Bacillus thuringiensis* NB-125 and/or *Bacillus thuringiensis* NB-176.

12. The inoculant composition of any one of the preceding paragraphs, wherein said microbial spores comprise, consist essentially of, or consist of spores of one or more strains of *Gliocladium*, optionally *Gliocladium virens* ATCC 52045 *Gliocladium virens* GL-3, and/or *Gliocladium virens* GL-21, one or more strains of *Glomus*, optionally *Glomus intraradices* RTI-801, one or more strains of *Metarhizium*, optionally *Metarhizium anisopliae* F52, *Penicillium*, optionally *Penicillium bilaiae* ATCC 18309, *Penicillium bilaiae* ATCC 20851, *Penicillium bilaiae* ATCC 22348, *Penicillium bilaiae* NRRL 50162, *Penicillium bilaiae* NRRL 50169, *Penicillium bilaiae* NRRL 50776, *Penicillium bilaiae* NRRL 50777, *Penicillium bilaiae* NRRL 50778, *Penicillium bilaiae* NRRL 50777, *Penicillium bilaiae* NRRL 50778, *Penicillium bilaiae* NRRL 50779, *Penicillium bilaiae* NRRL 50780, *Penicillium bilaiae* NRRL 50781, *Penicillium bilaiae* NRRL 50782, *Penicillium bilaiae* NRRL 50783, *Penicillium bilaiae* NRRL 50784, *Penicillium bilaiae* NRRL 50785, *Penicillium bilaiae* NRRL 50786, *Penicillium bilaiae* NRRL 50787, *Penicillium bilaiae* NRRL 50788, *Penicillium bilaiae* RS7B-SD1, *Penicillium brevicompactum* AgRF18, *Penicillium canescens* ATCC 10419, *Penicillium expansum* ATCC 24692, *Penicillium expansum* YT02, *Penicillium fellatanum* ATCC 48694, *Penicillium gaestrivorus* NRRL 50170, *Penicillium glabrum* DAOM 239074, *Penicillium glabrum* CBS 229.28, *Penicillium janthinellum* ATCC 10455, *Penicillium lanosocoeruleum* ATCC 48919, *Penicillium radicum* ATCC 201836, *Penicillium radicum* FRR 4717, *Penicillium radicum* FRR 4719, *Penicillium radicum* N93/47267 and/or *Penicillium raistrickii* ATCC 10490, and/or one or more strains of *Trichoderma*, optionally *Trichoderma asperellum* SKT-1, *Trichoderma asperellum* ICC 012, *Trichoderma atroviride* LC52, *Trichoderma atroviride* CNCM 1-1237, *Trichoderma fertile* JM41R, *Trichoderma gamsii* ICC 080, *Trichoderma hamatum* ATCC 52198, *Trichoderma harzianum* ATCC 52445, *Trichoderma harzianum* KRL-AG2, *Trichoderma harzianum* T-22, *Trichoderma harzianum* TH-35, *Trichoderma harzianum* T-39, *Trichoderma harzianum* ICC012, *Trichoderma reesi* ATCC 28217, *Trichoderma virens* ATCC 58678, *Trichoderma virens* GL-3, *Trichoderma virens* GL-21, *Trichoderma virens* G-41, *Trichoderma viridae* ATCC 52440, *Trichoderma viridae* ICC080 and/or *Trichoderma viridae* TV1.

13. The inoculant composition of any one of the preceding paragraphs, wherein said microbial spores comprise, consist essentially of, or consist of spores of one or more strains having a genomic sequence that is at least 75, 80, 85, 90, 95, 96, 97, 98, 99% or more identical to any of the strains recited in paragraph 11 on the basis of 16S rDNA sequence identity.

14. The inoculant composition of any one of the preceding paragraphs, wherein said microbial spores comprise, consist essentially of, or consist of spores of one or more strains having a genomic sequence that is at least 75, 80, 85, 90, 95, 96, 97, 98, 99% or more identical to any of the strains recited in paragraph 12 on the basis of internal transcribed spacer (ITS) and/or cytochrome c oxidase (CO1) sequence identity.

15. The inoculant composition of any one of the preceding paragraphs, wherein said microbial spores comprises, consists essentially of, or consists of spores of one or more biopesticides, optionally one or more biofungicides, one or more bioinsecticides and/or one or more bionematicides.

16. The inoculant composition of any one of the preceding paragraphs, wherein said non-aqueous carrier comprises about 70 to about 99% (by weight) of said inoculant composition, optionally about 75 to about 95% (by weight) of said composition, optionally about 80, 80.5, 81, 81.5, 82, 82.5, 83, 83.5, 84, 84.5, 85, 85.5, 86, 86.5, 87, 87.5, 88, 88.5, 89, 89.5 or 90% (by weight) of said inoculant composition.

17. The inoculant composition of any one of the preceding paragraphs, wherein said non-aqueous carrier comprises, consists essentially of or consists of a non-aqueous liquid carrier.

18. The inoculant composition of any one of the preceding paragraphs, wherein said non-aqueous carrier comprises, consists essentially of or consists of a non-aqueous solid carrier.

19. The inoculant composition of any one of the preceding paragraphs, wherein said non-aqueous carrier comprises less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95 or 1% water by weight, based upon the total weight of the composition.

20. The inoculant composition of any one of the preceding paragraphs, wherein said non-aqueous carrier comprises no water.

21. The inoculant composition of any one of the preceding paragraphs, wherein said non-aqueous carrier comprise, consist essentially of or consists of a seed- and/or soil-compatible carrier.

22. The inoculant composition of any one of the preceding paragraphs, wherein said non-aqueous carrier comprises, consists essentially of or consists of one or more oils, optionally one or more mineral oils and/or vegetable oils.

23. The inoculant composition of any one of the preceding paragraphs, wherein said non-aqueous carrier comprises, consists essentially of or consists of one or more polyethylene glycols, optionally PEG 200, PEG 300 and/or PEG 400.

24. The inoculant composition of any one of the preceding paragraphs, wherein said non-aqueous carrier comprises, consists essentially of or consists of one or more polypropylene glycols, optionally PPG-9, PPG-10, PPG-17, PPG-20 and/or PPG-26.

25. The inoculant composition of any one of the preceding paragraphs, wherein said inoculant composition comprises one or more protectants.

26. The inoculant composition of paragraph 25, wherein said one or more protectants comprise about 0.0001 to about 10% (by weight) of said composition, optionally about 2 to about 6% (by weight) of said composition, optionally about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 1, 1.5, 2, 2.5, 3, 3.5, 4, 4.5, 5, 5.5, 6, 7, 7.5, 8, 8.5, 9, 9.5 or 10% (by weight) of said composition.

27. The inoculant composition of any one of paragraphs 25-26, wherein said one or more protectants comprises:
one or more monosaccharides, optionally arabinose, fructose and/or glucose;
one or more disaccharides, optionally maltose, sucrose and/or trehalose;
one or more maltodextrins, optionally one or more maltodextrins (e.g., one or more maltodextrins (each and/or collectively) having a DEV value of about 15 to about 20;
one or more sugar alcohols, optionally arabitol, mannitol, sorbitol and/or xylitol;
one or more humic acids, optionally potassium humate and/or sodium humate;
one or more hygroscopic polymers, optionally one or more albumins, alginates, celluloses, gums (e.g., cellulose gum, guar gum, gum arabic, gum combretum, xantham gum), methyl celluloses, nylons, pectins, polyacrylic acids, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches;
one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid) and/or one or more oxygen scavengers, optionally ascorbic acid and/or sodium hydrogen carbonate; and/or
one or more UV protectants, optionally one or more lignosulfites.

28. The inoculant composition of any one of paragraphs 25-27, wherein said one or more protectants comprises, consists essentially of or consists of:
one or more monosaccharides, optionally arabinose, fructose and/or glucose, and one or more disaccharides, optionally maltose, sucrose and/or trehalose;
one or more monosaccharides, optionally arabinose, fructose and/or glucose, one or more maltodextrins, optionally one or more maltodextrins (e.g., one or more maltodextrins (each and/or collectively) having a DEV value of about 15 to about 20;
one or more monosaccharides, optionally arabinose, fructose and/or glucose, and one or more sugar alcohols, optionally arabitol, mannitol, sorbitol and/or xylitol;
one or more monosaccharides, optionally arabinose, fructose and/or glucose, and one or more humic acids, optionally potassium humate and/or sodium humate;

one or more monosaccharides, optionally arabinose, fructose and/or glucose, and one or more oxidation control components, optionally ascorbic acid and/or glutathione;

one or more monosaccharides, optionally arabinose, fructose and/or glucose, and one or more UV protectants, optionally one or more lignosulfites;

one or more disaccharides, optionally maltose, sucrose and/or trehalose, and one or more maltodextrins, optionally one or more maltodextrins (e.g., one or more maltodextrins (each and/or collectively) having a DEV value of about 15 to about 20;

one or more disaccharides, optionally maltose, sucrose and/or trehalose, and one or more sugar alcohols, optionally arabitol, mannitol, sorbitol and/or xylitol;

one or more disaccharides, optionally maltose, sucrose and/or trehalose, and one or more humic acids, optionally potassium humate and/or sodium humate;

one or more disaccharides, optionally maltose, sucrose and/or trehalose, and one or more oxidation control components, optionally ascorbic acid and/or glutathione;

one or more disaccharides, optionally maltose, sucrose and/or trehalose, and one or more UV protectants, optionally one or more lignosulfites;

one or more maltodextrins, optionally one or more maltodextrins (e.g., one or more maltodextrins (each and/or collectively) having a DEV value of about 15 to about 20, and one or more sugar alcohols, optionally arabitol, mannitol, sorbitol and/or xylitol;

one or more maltodextrins, optionally one or more maltodextrins (e.g., one or more maltodextrins (each and/or collectively) having a DEV value of about 15 to about 20, and one or more humic acids, optionally potassium humate and/or sodium humate;

one or more maltodextrins, optionally one or more maltodextrins (e.g., one or more maltodextrins (each and/or collectively) having a DEV value of about 15 to about 20, and one or more oxidation control components, optionally ascorbic acid and/or glutathione;

one or more maltodextrins, optionally one or more maltodextrins (e.g., one or more maltodextrins (each and/or collectively) having a DEV value of about 15 to about 20, and one or more UV protectants, optionally one or more lignosulfites;

one or more sugar alcohols, optionally arabitol, mannitol, sorbitol and/or xylitol, and one or more humic acids, optionally potassium humate and/or sodium humate;

one or more sugar alcohols, optionally arabitol, mannitol, sorbitol and/or xylitol, and one or more oxidation control components, optionally ascorbic acid and/or glutathione;

one or more sugar alcohols, optionally arabitol, mannitol, sorbitol and/or xylitol, and one or more UV protectants, optionally one or more lignosulfites; or one or more oxidation control components, optionally ascorbic acid and/or glutathione, and one or more UV protectants, optionally one or more lignosulfites.

29. The inoculant composition of any one of the preceding paragraphs, wherein said inoculant composition comprises one or more dispersants.

30. The inoculant composition of paragraph 29, wherein said one or more dispersants comprise about 0.1 to about 5% (by weight) of said composition, optionally about 0.1 to about 2% (by weight) of said composition, optionally about 0.1, 0.2, 0.3, 0.4, 0.5, 0.6, 0.7, 0.8, 0.9, 1, 1.5, 2, 2.5, 3, 3.5, 4, 4.5 or 5% (by weight) of said composition.

31. The inoculant composition of any one of paragraphs 29-30, wherein said one or more dispersants comprises:

one or more anionic surfactants, optionally one or more alkyl carboxylates, alkyl sulfates, alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarconsinates, acyl isethionates, N-acyl taurates, N-acyl-N-alkyltaurates, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and/or xylene sulfonates one or more cationic surfactants, optionally one or more alkyltrimethylammonium salts, cetylpyridinium chloride, benzalkonium chloride, benzethonium chloride, 5-Bromo-5-nitro-1,3-dioxane, dimethyldioctadecylammonium chloride, cetrimonium bromide, dioctadecyldimethylammonium bromide and/or octenidine dihydrochloride; and/or one or more non-ionic surfactants, optionally one or more alcohol ethoxylates, alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers, glycerol esters, glycol alkyl ethers, glycol alkylphenol ethers, glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pynolidones, sugar-based alkyl polyglycosides, sulfoanylamides, sorbitan fatty acid alcohol ethoxylates, sorbitan fatty acid ester ethoxylates, sorbitan fatty acid ester and/or tertiary acetylenic glycols; and/or one or more wetting agents, optionally one or more naphthalene sulfonates, optionally one or more alkyl naphthalene sulfonates, one or more isopropyl naphthalene sulfonates and/or one or more butyl naphthalene sulfonates.

32. The inoculant composition of any one of paragraphs 29-31, wherein said one or more dispersants comprises one or more polyoxyethylene alkyl ethers, one or more acrylic copolymers, one or more polyoxyethylene sorbitan trioleates and/or one or more secondary alcohol ethoxylates.

33. The inoculant composition of any one of the preceding paragraphs, wherein said inoculant composition comprises one or more pesticides, optionally:

one or more insecticides and/or nematicides, optionally one or more carbamates, diamides, macrocyclic lactones, neonicotinoids, organophosphates, phenylpyrazoles, pyrethrins, spinosyns, synthetic pyrethroids, tetronic acids and/or tetramic acids;

one or more fungicides, optionally one or more aromatic hydrocarbons, benzimidazoles, benzthiadiazole, carboxamides, carboxylic acid amides, morpholines, phenylamides, phosphonates, quinone outside inhibitors, thiazolidines, thiophanates, thiophene carboxamides and/or triazoles; and/or one or more herbicides, optionally one or more acetyl CoA carboxylase (ACCase) inhibitors, acetolactate synthase (ALS) inhibitors, acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin herbicide salts, auxin transport inhibitors, and/or nucleic acid inhibitors.

34. The inoculant composition of any one of the preceding paragraphs, wherein said inoculant composition comprises one more lipo-chitooligosaccharides, optionally one or more lipo-chitooligosaccharides represented by formulas I-IV.

35. The inoculant composition of any one of the preceding paragraphs, wherein said inoculant composition comprises one more lipo-chitooligosaccharides, optionally one or more of the lipo-chitooligosaccharides represented by structures V-XXXIII.

36. The inoculant composition of any one of the preceding paragraphs, wherein said inoculant composition comprises one or more chitooligosaccharides, optionally one or more chitooligosaccharides represented by formulas XXXIV-XXXV.

37. The inoculant composition of any one of the preceding paragraphs, wherein said inoculant composition comprises one or more chitooligosaccharides, optionally one or more chitooligosaccharides represented by structures XXXVI-XXXIX.

38. The inoculant composition of any one of the preceding paragraphs, wherein said inoculant composition comprises one or more chitinous compounds, optionally one or more chitins and/or one or more chitosans.

39. The inoculant composition of any one of the preceding paragraphs, wherein said inoculant composition comprises one or more flavonoids, optionally:

one or more anthocyanidins, optionally cyanidin, delphinidin, malvidin, pelargonidin, peonidin and/or petunidin;

one or more anthoxanthins, optionally one or more flavones, such as apigenin, baicalein, chrysin, 7,8-dihydroxyflavone, diosmin, flavoxate, 6-hydroxyflavone, luteolin, scutellarein, tangeritin and/or wogonin; and/or flavonols, such as amurensin, astragalin, azaleatin, azalein, fisetin, furanoflavonols galangin, gossypetin, 3-hydroxyflavone, hyperoside,icariin, isoquercetin, kaempferide, kaempferitrin, kaempferol, isorhamnetin, morin, myricetin, myricitrin, natsudaidain, pachypodol, pyranoflavonols quercetin, quericitin, rhamnazin, rhamnetin, robinin, rutin, spiraeoside, troxerutin and/or zanthorhamnin;

one or more flavanones, optionally butin, eriodictyol, hesperetin, hesperidin, homoeriodictyol, isosakuranetin, naringenin, naringin, pinocembrin, poncirin, sakuranetin, sakuranin and/or sterubin;

one or more flavanonols, optionally dihydrokaempferol and/or taxifolin; flavans, such as flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3,4-diols (e.g., leucocyanidin, leucodelphinidin, leucofisetinidin, leucomalvidin, luecopelargonidin, leucopeonidin, leucorobinetinidin, melacacidin and/or teracacidin); and/or one or more isoflavonoids, optionally one or more isoflavones, such as biochanin A, daidzein, formononetin, genistein and/or glycitein; isoflavanes, such as equol, ionchocarpane and/or laxifloorane; isoflavandiols; isoflavenes, such asglabrene, haginin D and/or 2-methoxyjudaicin; coumestans, such as coumestrol, plicadin and/or wedelolactone; pterocarpans; and/or roetonoids; and/or one or more neoflavonoids, optionally calophyllolide, coutareagenin, dalbergichromene, dalbergin and/or nivetin; and/or one or more pterocarpans, optionally bitucarpin A, bitucarpin B, erybraedin A, erybraedin B, erythrabyssin II, erthyrabissin-1, erycristagallin, glycinol, glyceollidins, glyceollins, glycyrrhizol, maackiain, medicarpin, morisianine, orientanol, phaseolin, pisatin, striatine and/or trifolirhizin.

40. The inoculant composition of any one of the preceding paragraphs, wherein said inoculant composition comprises jasmonic acid and/or one or more derivatives thereof.

41. The inoculant composition of any one of the preceding paragraphs, wherein said inoculant composition comprises *linoleic* acid and/or one or more derivatives thereof.

42. The inoculant composition of any one of the preceding paragraphs, wherein said inoculant composition comprises linolenic acid and/or one or more derivatives thereof.

43. The inoculant composition of any one of the preceding paragraphs, wherein said inoculant composition comprises one or more karrakins, optionally one or more karrakins represented by formula XXXX.

44. The inoculant composition of any one of the preceding paragraphs, wherein said inoculant composition comprises gluconolactone.

45. The inoculant composition of any one of the preceding paragraphs, wherein said inoculant composition comprises one or more drying agents, optionally calcium stearate, one or more clays, graphite, magnesium stearate, magnesium sulfate, powdered milk, one or more silica powders, soy lecithin and/or talc.

46. The inoculant composition of any one of the preceding paragraphs, wherein said inoculant composition comprises one or more biostimulants, optionally one or more seaweed extracts, one or more humic acids, one or more fulvic acids, myo-inositol and/or glycine.

47. The inoculant composition of any one of the preceding paragraphs, wherein said inoculant composition comprises one or more microbial extracts, optionally one or more extracts from media comprising one or more diazotrophic, phosphosphate-solubilizing and/or biopesticidal microorganisms.

48. The inoculant composition of any one of the preceding paragraphs, wherein said inoculant composition comprises one or more nutrients, optionally one or more vitamins (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$, choline) vitamin C, vitamin D, vitamin E, vitamin K, carotenoids ($\alpha$-carotene, $\beta$-carotene, cryptoxanthin, lutein, lycopene and/or zeaxanthin), macro-minerals (e.g., calcium, iron, magnesium, nitrogen, phosphorous, potassium and/or sodium), trace minerals (e.g., boron, cobalt, chloride, chromium, copper, fluoride, iodine, iron, manganese, molybdenum, selenium and/or zinc) and/or organic acids (e.g., acetic acid, citric acid, lactic acid, malic acid and/or taurine).

49. The inoculant composition of any one of the preceding paragraphs, wherein said inoculant composition comprises one or more growth media, optionally YEM media, mannitol yeast extract, glycerol yeast extract, Czapek-Dox media and/or potato dextrose broth.

50. The inoculant composition of any one of the preceding paragraphs, wherein said inoculant composition comprises one or more agriculturally acceptable anti-freezing agents, optionally ethylene glycol, glycerin, propylene glycol and/or urea.

51. The inoculant composition of any one of the preceding paragraphs, wherein said inoculant composition comprises less than 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5% water by weight, based upon the total weight of the composition.

52. The composition of any one of the preceding paragraphs, wherein said inoculant composition comprises, consists essentially of or is a liquid.

53. The composition of any one of the preceding paragraphs, wherein said inoculant composition comprises, consists essentially of or is an amorphous liquid.

54. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microbial spores remain viable when said inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more.

55. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microbial spores remain viable when said inoculant composition is coated on a plant propagation material.

56. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microbial spores remain viable when said inoculant composition is coated on a plant propagation material and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more.

57. The inoculant composition of any one of the preceding paragraphs, wherein at least about $1 \times 10^1$ to about $1 \times 10^{10}$ colony-forming units of said one or more microbial spores per gram and/or milliliter of said inoculant composition remain viable when said inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more, optionally at least $1 \times 10^4$, $1 \times 10$, $1 \times 10^6$, $1 \times 10^7$ or more colony-forming units per gram and/or milliliter of said inoculant composition.

58. The inoculant composition of any one of the preceding paragraphs, wherein at least about $1 \times 10^1$ to about $1 \times 10^{10}$ colony-forming units of said one or more microbial spores per seed remain viable when said inoculant composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more, optionally $1 \times 10^4$, $1 \times 10^5$, $1 \times 10^6$, $1 \times 10^7$ or more colony-forming units per seed.

59. A coated plant propagation material, comprising, consisting essentially of, or consisting of: a plant propagation material; and a coating that covers at least a portion of an outer surface of said seed, said coating comprising, consisting essentially of, or consisting of the inoculant composition of any one of paragraphs 1-58.

60. The coated plant propagation material paragraph 59, wherein said coating comprises, consists essentially of, or consists of an inner coating layer that comprises said microbial spores and an outer coating layer that is devoid of said microbial spores.

61. The coated plant propagation material of any one of paragraphs 59-60, wherein said coating comprises, consists essentially of or is an amorphous liquid.

62. The coated plant propagation material of any one of paragraphs 59-60, wherein said coating comprises, consists essentially of or is an amorphous solid.

63. The coated plant propagation material of any one of paragraphs 59-62, wherein said coating comprises about $1 \times 10^1$ to about $1 \times 10^{15}$ colony-forming units of said microbial spores, optionally $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ or more colony-forming units.

64. The coated plant propagation material any one of paragraphs 59-63, wherein said plant propagation material is a seed.

65. The coated plant propagation material of paragraph 64, wherein said seed is a monocot seed.

66. The coated plant propagation material of paragraph 64, wherein said seed is a dicot seed.

67. The coated plant propagation material of paragraph 64, wherein said seed is a leguminous seed.

68. The coated plant propagation material of paragraph 64, wherein said seed is a non-leguminous seed.

69. The coated plant propagation material of any one of paragraphs 59-64, wherein said plant propagation material is of the family Amaranthaceae, optionally chard, spinach, sugar beet, or *quinoa*.

70. The coated plant propagation material of any one of paragraphs 59-64, wherein said plant propagation material is of the family Asteraceae, optionally artichoke, asters, chamomile, chicory, chrysanthemums, dahlias, daisies, *echinacea*, goldenrod, guayule, lettuce, marigolds, safflower, sunflowers, or zinnias.

71. The coated plant propagation material of any one of paragraphs 59-64, wherein said plant propagation material is of the family Brassicaceae, optionally arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, or *Arabidopsis thaliana.*

72. The coated plant propagation material of any one of paragraphs 59-64, wherein said plant propagation material is of the family Cucurbitaceae, optionally cantaloupe, cucumber, honeydew, melon, pumpkin, squash (e.g., acorn squash, butternut squash, summer squash), watermelon, or zucchini.

73. The coated plant propagation material of any one of paragraphs 59-64, wherein said plant propagation material is of the family Fabaceae, optionally alfalfa, beans, carob, clover, guar, lentils, mesquite, peas, peanuts, soybeans, tamarind, tragacanth, or vetch.

74. The coated plant propagation material of any one of paragraphs 59-64, wherein said plant propagation material is of the family Malvaceae, optionally cacao, cotton, durian, hibiscus, kenaf, kola, or okra.

75. The coated plant propagation material of any one of paragraphs 59-64, wherein said plant propagation material is of the family Poaceae, optionally bamboo, barley, corn, fonio, lawn grass (e.g., Bahia grass, Bermudagrass, bluegrass, Buffalograss, Centipede grass, Fescue, or *Zoysia*), millet, oats, ornamental grasses, rice, rye, sorghum, sugar cane, triticale, or wheat.

76. The coated plant propagation material of any one of paragraphs 59-64, wherein said plant propagation material is of the family Polygonaceae, optionally buckwheat.

77. The coated plant propagation material of any one of paragraphs 59-64, wherein said plant propagation material is of the family Rosaceae, optionally almonds, apples, apricots, blackberry, blueberry, cherries, peaches, plums, quinces, raspberries, roses, or strawberries.

78. The coated plant propagation material of any one of paragraphs 59-64, wherein said plant propagation material is of the family Solanaceae, optionally bell peppers, chili peppers, eggplant, *petunia*, potato, tobacco, or tomato.

79. The coated plant propagation material of any one of paragraphs 59-64, wherein said plant propagation material is of the family Vitaceae, optionally grape.

80. A kit, comprising: the coated plant propagation material of any one of paragraphs 59 to 79; and a container housing said coated plant propagation material.

81. The kit of paragraph 80, wherein said container reduces the amount of ambient light that reaches said coated plant propagation material by about 5, 10, 15, 20, 25, 30, 35, 40, 45, 50, 55, 60, 65, 70, 75, 80, 85, 90, 95 or 100% when sealed.

82. The kit of any one of paragraphs 80-81, wherein said container reduces the amount of ambient oxygen that reaches said plant propagation material by about 5, 10, 15, 20, 25, 30, 35, 40, 45, 50, 55, 60, 65, 70, 75, 80, 85, 90, 95 or 100% when sealed.

83. The kit of any one of paragraphs 80-82, wherein said container comprises, consists essentially of, or consists of a material having light permeability of less than about 1, 2, 3, 4, 5, 6, 7, 8, 9, 10, 15, 20, 25, 30, 35, 40, 45, 50, 55, 60, 65, 70 or 75%.

84. The kit of any one of paragraphs 80-83, wherein said container comprises, consists essentially of, or consists of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 cm$^3$/m$^2$-day (as measured in accordance with ASTM D3985).

85. The kit of any one of paragraphs 80-84, wherein said kit further comprises one or more oxygen-absorbing compound, optionally activated carbon, iron powder, sodium chloride, ferrous carbonate, one or more metal halide catalysts and/or sodium hydrogen carbonate.

86. A plant treated with the inoculant composition of any one of paragraphs 1-58.

87. A plant germinated from the coated plant propagation material of any one of paragraphs 59-79.

88. A plant part harvested from the plant of any one of paragraphs 86-87.

89. A processed product produced from the plant part of paragraph 88.

90. A crop comprising, consisting essentially of, or consisting of a plurality of the plant or plant part of any one of paragraphs 86-88.

91. A method, comprising, consisting essentially of, or consisting of: applying the inoculant composition of any one of paragraphs 1-58 to a plant propagation material.

92. The method of paragraph 91, further comprising planting said plant propagation material in a growth medium, optionally soil.

93. The method of paragraph 92, wherein said plant propagation material is planted in soil in which plants of the same genus were cultivated in at least one of the three years prior to said planting, optionally in each of the one, two or three years immediately preceding said planting.

94. The method of any one of paragraphs 91-93, wherein said inoculant composition is applied to the plant propagation material at the time of planting.

95. The method of any one of paragraphs 91-93, wherein said inoculant composition is applied to the plant propagation material at least 1, 2, 3, 4, 5, 6, 7, 8, 9, 10, 11, 12, 15, 18, 21, 24, 27, 30, 33, 36, 39, 42, 45, 48 hours or more prior to planting.

96. The method of any one of paragraphs 91-93, wherein said inoculant composition is applied to the plant propagation material at least 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more prior to planting.

97. The method of any one of paragraphs 91-93, wherein said inoculant composition is applied to the plant propagation material about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 months or more prior to planting 98. The method of any one of paragraphs 91-97, wherein said plant propagation material is a seed.

99. The method of any one of paragraphs 91-97, wherein said plant propagation material is a monocot seed.

100. The method of any one of paragraphs 91-97, wherein said plant propagation material is a dicot seed.

101. The method of any one of paragraphs 91-97, wherein said plant propagation material is a leguminous seed.

102. The method of any one of paragraphs 91-97, wherein said plant propagation material is a non-leguminous seed.

103. The method of any one of paragraphs 91-98, wherein said plant propagation material is of the family Amaranthaceae, optionally chard, spinach, sugar beet, or *quinoa.*

104. The method of any one of paragraphs 91-98, wherein said plant propagation material is of the family Asteraceae, optionally artichoke, asters, chamomile, chicory, chrysanthemums, dahlias, daisies, *echinacea*, goldenrod, guayule, lettuce, marigolds, safflower, sunflowers, or zinnias.

105. The method of any one of paragraphs 91-98, wherein said plant propagation material is of the family Brassicaceae, optionally arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, or *Arabidopsis thaliana.*

106. The method of any one of paragraphs 91-98, wherein said plant propagation material is of the family Cucurbitaceae, optionally cantaloupe, cucumber, honeydew, melon, pumpkin, squash (e.g., acorn squash, butternut squash, summer squash), watermelon, or zucchini.

107. The method of any one of paragraphs 91-98, wherein said plant propagation material is of the family Fabaceae, optionally alfalfa, beans, carob, clover, guar, lentils, mesquite, peas, peanuts, soybeans, tamarind, tragacanth, or vetch.

108. The method of any one of paragraphs 91-98, wherein said plant propagation material is of the family Malvaceae, optionally cacao, cotton, durian, hibiscus, kenaf, kola, or okra.

109. The method of any one of paragraphs 91-98, wherein said plant propagation material is of the family Poaceae, optionally bamboo, barley, corn, fonio, lawn grass (e.g., Bahia grass, Bermudagrass, bluegrass, Buffalograss, Centipede grass, Fescue, or *Zoysia*), millet, oats, ornamental grasses, rice, rye, sorghum, sugar cane, triticale, or wheat.

110. The method of any one of paragraphs 91-98, wherein said plant propagation material is of the family Polygonaceae, optionally buckwheat.

111. The method of any one of paragraphs 91-98, wherein said plant propagation material is of the family Rosaceae, optionally almonds, apples, apricots, blackberry, blueberry, cherries, peaches, plums, quinces, raspberries, roses, or strawberries.

112. The method of any one of paragraphs 91-98, wherein said plant propagation material is of the family Solanaceae, optionally bell peppers, chili peppers, eggplant, *petunia*, potato, tobacco, or tomato.

113. The method of any one of paragraphs 91-98, wherein plant propagation material seed is of the family Vitaceae, optionally grape.

114. A method comprising, consisting essentially of, or consisting of: planting the coated plant propagation material of any one of paragraphs 59-79 in a growth medium, optionally soil.

115. The method of any one of paragraphs 91-114, further comprising applying the inoculant composition of any one of paragraphs 1-94 to the plant that grows from the plant propagation material.

116. A method of enhancing the stability and/or survivability of one or more microorganisms in a composition, comprising, consisting essentially of, or consisting of:

adding one or more protectants to said composition, said one or more protectants comprising:

one or more monosaccharides, optionally arabinose, fructose and/or glucose;

one or more disaccharides, optionally maltose, sucrose and/or trehalose;

one or more maltodextrins, optionally one or more maltodextrins (e.g., one or more maltodextrins (each and/or collectively) having a DEV value of about 15 to about 20;

one or more sugar alcohols, optionally arabitol, mannitol, sorbitol and/or xylitol;

one or more humic acids, optionally potassium humate and/or sodium humate;

one or more hygroscopic polymers, optionally one or more albumins, alginates, celluloses, gums (e.g., cellulose gum, guar gum, gum arabic, gum combretum, xantham gum), methyl celluloses, nylons, pectins, polyacrylic acids, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches;

one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid) and/or one or more oxygen scavengers, optionally ascorbic acid and/or sodium hydrogen carbonate; and/or one or more UV protectants, optionally one or more lignosulfites.

117. The method of paragraph 152, wherein said one or more protectants comprises, consists essentially of, or consists of:

one or more monosaccharides, optionally arabinose, fructose and/or glucose, and one or more disaccharides, optionally maltose, sucrose and/or trehalose;

one or more monosaccharides, optionally arabinose, fructose and/or glucose, one or more maltodextrins, optionally one or more maltodextrins (e.g., one or more maltodextrins (each and/or collectively) having a DEV value of about 15 to about 20;

one or more monosaccharides, optionally arabinose, fructose and/or glucose, and one or more sugar alcohols, optionally arabitol, mannitol, sorbitol and/or xylitol;

one or more monosaccharides, optionally arabinose, fructose and/or glucose, and one or more humic acids, optionally potassium humate and/or sodium humate;

one or more monosaccharides, optionally arabinose, fructose and/or glucose, and one or more oxidation control components, optionally ascorbic acid and/or glutathione;

one or more monosaccharides, optionally arabinose, fructose and/or glucose, and one or more UV protectants, optionally one or more lignosulfites;

one or more disaccharides, optionally maltose, sucrose and/or trehalose, and one or more maltodextrins, optionally one or more maltodextrins (e.g., one or more maltodextrins (each and/or collectively) having a DEV value of about 15 to about 20;

one or more disaccharides, optionally maltose, sucrose and/or trehalose, and one or more sugar alcohols, optionally arabitol, mannitol, sorbitol and/or xylitol;

one or more disaccharides, optionally maltose, sucrose and/or trehalose, and one or more humic acids, optionally potassium humate and/or sodium humate;

one or more disaccharides, optionally maltose, sucrose and/or trehalose, and one or more oxidation control components, optionally ascorbic acid and/or glutathione;

one or more disaccharides, optionally maltose, sucrose and/or trehalose, and one or more UV protectants, optionally one or more lignosulfites;

one or more maltodextrins, optionally one or more maltodextrins (e.g., one or more maltodextrins (each and/or collectively) having a DEV value of about 15 to about 20, and one or more sugar alcohols, optionally arabitol, mannitol, sorbitol and/or xylitol;

one or more maltodextrins, optionally one or more maltodextrins (e.g., one or more maltodextrins (each and/or collectively) having a DEV value of about 15 to about 20, and one or more humic acids, optionally potassium humate and/or sodium humate;

one or more maltodextrins, optionally one or more maltodextrins (e.g., one or more maltodextrins (each and/or collectively) having a DEV value of about 15 to about 20, and one or more oxidation control components, optionally ascorbic acid and/or glutathione;

one or more maltodextrins, optionally one or more maltodextrins (e.g., one or more maltodextrins (each and/or collectively) having a DEV value of about 15 to about 20, and one or more UV protectants, optionally one or more lignosulfites;

one or more sugar alcohols, optionally arabitol, mannitol, sorbitol and/or xylitol, and one or more humic acids, optionally potassium humate and/or sodium humate;

one or more sugar alcohols, optionally arabitol, mannitol, sorbitol and/or xylitol, and one or more oxidation control components, optionally ascorbic acid and/or glutathione;

one or more sugar alcohols, optionally arabitol, mannitol, sorbitol and/or xylitol, and one or more UV protectants, optionally one or more lignosulfites; or one or more oxidation control components, optionally ascorbic acid and/or glutathione, and one or more UV protectants, optionally one or more lignosulfites.

118. The method of any one of paragraphs 116-117, wherein said one or more protectants is added until it comprises about 0.0001 to about 10% (by weight) of said composition, optionally about 2 to about 6% (by weight) of said composition, optionally about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 1, 1.5, 2, 2.5, 3, 3.5, 4, 4.5, 5, 5.5, 6, 7, 7.5, 8, 8.5, 9, 9.5 or 10% (by weight) of said composition.

119. The method of any one of paragraphs 116-118, wherein said one or more protectants is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said microbial spores remain viable when said inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more.

120. The method of any one of paragraphs 116-119, wherein said one or more protectants is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said microbial spores remain viable when said inoculant composition is coated on a plant propagation material.

121. The method of any one of paragraphs 116-120, wherein said one or more protectants is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said microbial spores remain viable when said inoculant composition is coated on a plant propagation material and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more.

122. The method of any one of paragraphs 116-121, wherein said one or more protectants is added in an amount sufficient to ensure that at least about $1 \times 10^1$ to about $1 \times 10^{15}$ colony-forming units of said microbial spores per gram and/or milliliter of said inoculant composition remain viable when said inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more, optionally at least $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ or more colony-forming units per gram and/or milliliter of said inoculant composition.

123. The method of any one of paragraphs 116-122, wherein said one or more protectants is added in an amount sufficient to ensure that at least about $1 \times 10^1$ to about $1 \times 10^{15}$ colony-forming units of said microbial spores per seed remain viable when said inoculant composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more, optionally $1 \times 10^1$, $1 \times 10^2$, $1 \times 10^3$, $1 \times 10^4$, $1 \times 10^5$, $1 \times 10^6$, $1 \times 10^7$, $1 \times 10^1$, $1 \times 10^9$, $1 \times 10^1$, $1 \times 10^{11}$, $1 \times 10^{12}$ or more colony-forming units per seed.

124. The method of any of paragraphs 116-123, further comprising: adding one or more dispersants to said composition.

125. The method of paragraph 124, wherein said one or more dispersants comprises:

one or more anionic surfactants, optionally one or more alkyl carboxylates, alkyl sulfates, alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarconsinates, acyl isethionates, N-acyl taurates, N-acyl-N-alkyltaurates, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and/or xylene sulfonates one or more cationic surfactants, optionally one or more alkyltrimethylammonium salts, cetylpyridinium chloride, benzalkonium chloride, benzethonium chloride, 5-bromo-5-nitro-1,3-dioxane, dimethyldioctadecylammonium chloride, cetrimonium bromide, dioctadecyldimethylammonium bromide and/or octenidine dihydrochloride; and/or one or more non-ionic surfactants, optionally one or more alcohol ethoxylates, alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers, glycerol esters, glycol alkyl ethers, glycol alkylphenol ethers, glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pynolidones, sugar-based alkyl polyglycosides, sulfoanylamides, sorbitan fatty acid alcohol ethoxylates, sorbitan fatty acid ester ethoxylates, sorbitan fatty acid ester and/or tertiary acetylenic glycols; and/or one or more wetting agents, optionally one or more naphthalene sulfonates, optionally one or more alkyl naphthalene sulfonates, one or more isopropyl naphthalene sulfonates and/or one or more butyl naphthalene sulfonates.

126. The inoculant composition of any one of paragraphs 124-125, wherein said one or more dispersants comprises one or more polyoxyethylene alkyl ethers, one or more acrylic copolymers, one or more polyoxyethylene sorbitan trioleates and/or one or more secondary alcohol ethoxylates.

127. The method of any one of paragraphs 116-123, further:

adding one or more aqueous additives to said composition.

128. The method of paragraph 127, wherein said one or more aqueous additives comprises: one or more *Bacillus* extracts, optionally an extract of media comprising *B. amyloliquefaciens* D747, *B. amyloliquefaciens* NRRL B-50349, *B. amyloliquefaciens* TJ1000, *B. amyloliquefaciens* FZB24, *B. amyloliquefaciens* FZB42, *B. amyloliquefaciens* IN937a, *B. amyloliquefaciens* IT-45, *B. amyloliquefaciens* TJ1000, *B. amyloliquefaciens* MBI600, *B. amyloliquefaciens* BS27 (deposited as NRRL B-5015), *B. amyloliquefaciens* BS2084 (deposited as NRRL B-50013), *B. amyloliquefaciens* 15AP4 (deposited as ATCC PTA-6507), *B. amyloliquefaciens* 3AP4 (deposited as ATCC PTA-6506), *B. amyloliquefaciens* LSSA01 (deposited as NRRL B-50104), *B. amyloliquefaciens* ABP278 (deposited as NRRL B-50634), *B. amyloliquefaciens* 1013 (deposited as NRRL B-50509), *B. amyloliquefaciens* 918 (deposited as NRRL B-50508), *B. amyloliquefaciens* 22CP1 (deposited as ATCC PTA-6508) and *B. amyloliquefaciens* BS18 (deposited as NRRL B-50633), *B. cereus* I-1562, *B. firmus* I-1582, *B. lichenformis* BA842 (deposited as NRRL B-50516), *B. lichenformis* BL21 (deposited as NRRL B-50134), *B. mycoides* NRRL B-21664, *B. pumilus* NRRL B-21662, *B.*

*pumilus* NRRL B-30087, *B. pumilus* ATCC 55608, *B. pumilus* ATCC 55609, *B. pumilus* GB34, *B. pumilus* KFP9F, *B. pumilus* QST 2808, *B. subtilis* ATCC 55078, *B. subtilis* ATCC 55079, *B. subtilis* MBI600, *B. subtilis* NRRL B-21661, *B. subtilis* NRRL B-21665, *B. subtilis* CX-9060, *B. subtilis* GB03, *B. subtilis* GB07, *B. subtilis* QST-713, *B. subtilis* FZB24, *B. subtilis* D747, *B. subtilis* 3BP5 (deposited as NRRL B-50510), *B. thuringiensis* ATCC 13367, *B. thuringiensis* GC-91, *B. thuringiensis* NRRL B-21619, *B. thuringiensis* ABTS-1857, *B. thuringiensis* SAN 401 I, *B. thuringiensis* ABG-6305, *B. thuringiensis* ABG-6346, *B. thuringiensis* AM65-52, *B. thuringiensis* SA-12, *B. thuringiensis* SB4, *B. thuringiensis* ABTS-351, *B. thuringiensis* HD-1, *B. thuringiensis* EG 2348, *B. thuringiensis* EG 7826, *B. thuringiensis* EG 7841, *B. thuringiensis* DSM 2803, *B. thuringiensis* NB-125 and/or *B. thuringiensis* NB-176;

one or more *Bradyrhizobium* extracts, optionally an extract of media comprising *B. elkanii* SEMIA 501, *B. elkanii* SEMIA 587, *B. elkanii* SEMIA 5019, *B. japonicum* NRRL B-50586 (also deposited as NRRL B-59565), *B. japonicum* NRRL B-50587 (also deposited as NRRL B-59566), *B. japonicum* NRRL B-50588 (also deposited as NRRL B-59567), *B. japonicum* NRRL B-50589 (also deposited as NRRL B-59568), *B. japonicum* NRRL B-50590 (also deposited as NRRL B-59569), *B. japonicum* NRRL B-50591 (also deposited as NRRL B-59570), *B. japonicum* NRRL B-50592 (also deposited as NRRL B-59571), *B. japonicum* NRRL B-50593 (also deposited as NRRL B-59572), *B. japonicum* NRRL B-50594 (also deposited as NRRL B-50493), *B. japonicum* NRRL B-50608, *B. japonicum* NRRL B-50609, *B. japonicum* NRRL B-50610, *B. japonicum* NRRL B-50611, *B. japonicum* NRRL B-50612, *B. japonicum* NRRL B-50726, *B. japonicum* NRRL B-50727, *B. japonicum* NRRL B-50728, *B. japonicum* NRRL B-50729, *B. japonicum* NRRL B-50730, *B. japonicum* SEMIA 566, *B. japonicum* SEMIA 5079, *B. japonicum* SEMIA 5080, *B. japonicum* USDA 6, *B. japonicum* USDA 110, *B. japonicum* USDA 122, *B. japonicum* USDA 123, *B. japonicum* USDA 127, *B. japonicum* USDA 129 and/or *B. japonicum* USDA 532C;

one or more *Rhizobium* extracts, optionally an extract of media comprising *R. leguminosarum* SO12A-2;

one or more *Sinorhizobium* extracts, optionally an extract of media comprising *S. fredii* CCBAU114 and/or *S. fredii* USDA 205;

one or more *Penicillium* extracts, optionally an extract of media comprising *P. bilaiae* ATCC 18309, *P. bilaiae* ATCC 20851, *P. bilaiae* ATCC 22348, *P. bilaiae* NRRL 50162, *P. bilaiae* NRRL 50169, *P. bilaiae* NRRL 50776, *P. bilaiae* NRRL 50777, *P. bilaiae* NRRL 50778, *P. bilaiae* NRRL 50777, *P. bilaiae* NRRL 50778, *P. bilaiae* NRRL 50779, *P. bilaiae* NRRL 50780, *P. bilaiae* NRRL 50781, *P. bilaiae* NRRL 50782, *P. bilaiae* NRRL 50783, *P. bilaiae* NRRL 50784, *P. bilaiae* NRRL 50785, *P. bilaiae* NRRL 50786, *P. bilaiae* NRRL 50787, *P. bilaiae* NRRL 50788, *P. bilaiae* RS7B-SD1, *P. brevicompactum* AgRF18, *P. canescens* ATCC 10419, *P. expansum* ATCC 24692, *P. expansum* YT02, *P. fellatanum* ATCC 48694, *P. gaestrivorus* NRRL 50170, *P. glabrum* DAOM 239074, *P. glabrum* CBS 229.28, *P. janthinellum* ATCC 10455, *P. lanosocoeruleum* ATCC 48919, *P. radicum* ATCC 201836, *P. radicum* FRR 4717, *P. radicum* FRR 4719, *P. radicum* N93/47267 and/or *P. raistrickii* ATCC 10490;

one or more *Streptomyces* extracts, optionally an extract of media comprising *Streptomyces* NRRL B-30145, *Streptomyces* M1064, *S. galbus* NRRL 30232, S, *lydicus* WYEC 108 (ATCC 55445), *S. violaceusniger* YCED 9 (ATCC 55660) and/or *Streptomyces* WYE 53 (ATCC 55750); and/or one or more *Trichoderma* extracts, optionally an extract of media comprising *T. asperellum* SKT-1 (ECO-HOPE®, Kumiai Chemical Industry Co., Ltd., Japan), *T. atroviride* LC52 (SENTINEL®, Agrimm Technologies Ltd, NZ), *T. harzianum* T-22 (PLANTSHIELD®, BioWorks Inc., USA), *T. harzianum* TH-35 (ROOT PRO®, Mycontrol Ltd., Israel), *T. harzianum* T-39 (TRICHODEX®, Mycontrol Ltd., Israel; T. 2000®, Makhteshim Ltd., Israel), *T. harzianum* ICC012 and *T. viride* TRICHOPEL (Agrimm Technologies Ltd, NZ), *T. harzianum* ICC012 and *T. viride* ICC080 (REMEDIER® WP, Isagro Ricerca, Italy), *T. polysporum* and *T. harzianum* (BINAB®, BINAB Bio-Innovation AB, Sweden), *T. stromaticum* TRICOVAB® (C.E.P.L.A.C., Brazil), *T. virens* GL-3, ATCC 58678, *T. virens* GL-21 *T. viride* TRIECO® (Ecosense Labs. (India) Pvt. Ltd., India, BIO-CURE® F, T. Stanes & Co. Ltd., India), *T. viride* TV1 (Agribiotec srl, Italy), *T. viride* ICC080.

129. The inoculant composition of any one of paragraphs 127-128, wherein said one or more aqueous additives comprises less than 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5% water by weight, based upon the total weight of the composition.

130. The method of any one of paragraphs 127-129, wherein said one or more aqueous additives is added until it comprises about 0.1 to about 5% (by weight) of said composition, optionally about 0.1 to about 2% (by weight) of said composition, optionally about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5% or more (by weight) of said composition.

131. A method, comprising, consisting essentially of or consisting of:

applying the inoculant composition of any one of paragraphs 1-58 to a seed and/or to the plant that grows from said seed;

applying a second composition to said seed and/or to the plant that grows from said seed, said second composition comprising:

one or more agriculturally beneficial microorganisms, optionally one or more diazotrophs, one or more phosphate-solubilizing microorganisms, one or more mycorrhizal fungi and/or one or more biopesticides, optionally one or more biofungicides, one or more bioinsecticides and/or one or more bionematicides;

one or more biostimulants, optionally one or more seaweed extracts, one or more humic acids, one or more fulvic acids, myo-inositol and/or glycine;

one or more nutrients, optionally one or more vitamins (e.g., vitamin A, vitamin B complex (i.e., vitamin B1, vitamin B2, vitamin B3, vitamin B5, vitamin B6, vitamin B7, vitamin B8, vitamin B9, vitamin B12, choline) vitamin C, vitamin D, vitamin E, vitamin K, carotenoids (α-carotene, β-carotene, cryptoxanthin, lutein, lycopene and/or zeaxanthin), macrominerals (e.g., calcium, iron, magnesium, nitrogen, phosphorous, potassium and/or sodium), trace minerals (e.g., boron, cobalt, chloride, chromium, copper, fluoride, iodine, iron, manganese, molybdenum, selenium and/or zinc) and/or organic acids (e.g., acetic acid, citric acid, lactic acid, malic acid and/or taurine);

one or more fungicides, optionally one or more of the fungicides expressly disclosed above;

one or more herbicides, optionally one or more of the herbicides expressly disclosed above;

one or more insecticides, optionally one or more of the insecticides expressly disclosed above;

one or more nematicides, optionally one or more of the nematicides expressly disclosed above;

one or more lipo-chitooligosaccharides, optionally one or more of the lipo-chitooligosaccharides represented by formulas I-IV and/or one or more of the lipo-chitooligosaccharides represented by structures V-XXXIII;

one or more chitooligosaccharides, optionally one or more of the chitooligosaccharides represented by formulas XXXIV-XXXV and/or one or more of the chitooligosaccharides represented by structures XXXVI-XXXIX, one or more chitinous compounds, optionally one or more chitins and/or one or more chitosans;

one or more flavonoids, optionally one or more anthocyanidins, such as cyanidin, delphinidin, malvidin, pelargonidin, peonidin and/or petunidin; anthoxanthins, such as flavones (e.g., apigenin, baicalein, chrysin, 7,8-dihydroxyflavone, diosmin, flavoxate, 6-hydroxyflavone, luteolin, scutellarein, tangeritin and/or wogonin) and/or flavonols (e.g., amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, pyranoflavonols quercetin, quericitin, rhamnazin, rhamnetin, robinin, rutin, spiraeoside, troxerutin and/or zanthorhamnin); flavanones, such as butin, eriodictyol, hesperetin, hesperidin, homoeriodictyol, isosakuranetin, naringenin, naringin, pinocembrin, poncirin, sakuranetin, sakuranin and/or sterubin; flavanonols, such as dihydrokaempferol and/or taxifolin; flavans, such as flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3,4-diols (e.g., leucocyanidin, leucodelphinidin, leucofisetinidin, leucomalvidin, luecopelargonidin, leucopeonidin, leucorobinetinidin, melacacidin and/or teracacidin); and/or isoflavonoids, such as isoflavones (e.g, biochanin A, daidzein, formononetin, genistein and/or glycitein), isoflavanes (e.g., equol, ionchocarpane and/or laxifloorane), isoflavandiols, isoflavenes (e.g., glabrene, haginin D and/or 2-methoxyjudaicin), coumestans (e.g., coumestrol, plicadin and/or wedelolactone), pterocarpans and/or roetonoids; and/or one or more analogues, derivatives, hydrates, isomers, polymers, salts and solvates thereof, such as neoflavonoids (e.g, calophyllolide, coutareagenin, dalbergichromene, dalbergin and/or nivetin) and/or pterocarpans (e.g., bitucarpin A, bitucarpin B, erybraedin A, erybraedin B, erythrabyssin II, erthyrabissin-1, erycristagallin, glycinol, glyceollidins, glyceollins, glycyrrhizol, maackiain, medicarpin, morisianine, orientanol, phaseolin, pisatin, striatine and/or trifolirhizin);

jasmonic acid and/or one or more derivatives thereof; *linoleic* acid and/or one or more derivatives thereof; linolenic acid and/or one or more derivatives thereof; one or more karrakins, optionally one or more karrakins represented by formula XXXX; gluconolactone; and/or one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid) and/or one or more oxygen scavengers, optionally ascorbic acid and/or sodium hydrogen carbonate.

EXAMPLES

The following examples are not intended to be a detailed catalogue of all the different ways in which the present disclosure may be implemented or of all the features that may be added to the present disclosure. Subjects skilled in the art will appreciate that numerous variations and additions to the various embodiments may be made without departing from the present disclosure. Hence, the following descriptions are intended to illustrate some particular embodiments of the invention and not to exhaustively specify all permutations, combinations and variations thereof.

Example 1

Stable Aqueous Liquid Inoculants Comprising *Penicillium* Spores

Aqueous liquid inoculant compositions comprising *Penicillium bilaiae* spores (ATCC 20851 and/or RS71B-SD1) were stored for four weeks at 20° C. alongside a commercially available wettable powder comprising *Penicillium bilaiae* spores (ATCC 20851 and RS71B-SD1). As shown in Table 1, the survival rate of *Penicillium* spores was greater in each of the aqueous liquid inoculant compositions than in the commercially available wettable powder.

TABLE 1

| | Inoculant Composition | Viable spores after 4 weeks at 20° C.[1] |
|---|---|---|
| A | PEG 300 + *P. bilaiae* spores (10% w/w) + TERGITOL ™15-S-9 (1% w/w) + 6.9 g/ml trehalose solution (5% w/w) (total water content of the composition = 0.635% w/w) | 76% |
| B | PEG 300 + *P. bilaiae* spores (10% w/w) + TERGITOL ™15-S-9 (1% w/w) + 1.06 g/ml maltose solution (5% w/w) (total water content of the composition = 2.425% w/w) | 79% |
| Control | Commercially available wettable powder comprising *P. bilaiae* spores | 73% |

[1]Expressed as a percentage of the spore content (cfu per gram of inoculant composition) measured at time zero.

Example 2

Stable Aqueous Liquid Inoculants Comprising *Penicillium* Spores

Aqueous liquid inoculant compositions comprising *Penicillium bilaiae* spores (ATCC 20851 and/or RS71B-SD1) were stored for twenty weeks at 20° C. alongside a commercially available wettable powder comprising *Penicillium bilaiae* spores (ATCC 20851 and RS71B-SD1). As shown in Table 2, the survival rate of *Penicillium* spores was greater in each of the aqueous liquid inoculant compositions than in the commercially available wettable powder.

TABLE 2

| | Inoculant Composition | Viable spores after 20 weeks at 20° C.[1] |
|---|---|---|
| C | PEG 300 + *P. bilaiae* spores (10% w/w) + TERGITOL ™15-S-9 (1% w/w) + OPTIMIZE ® liquid additive w/maltose added to 0.43 g/ml (5% w/w) (total water content of the composition = 1.56% w/w) | 160% |
| D | PEG 300 + *P. bilaiae* spores (10% w/w) + TERGITOL ™15-S-9 (1% w/w) + OPTIMIZE ® liquid additive w/trehalose added to 0.42 g/ml (5% w/w) (total water content of the composition = 1.52% w/w) | 112% |
| Control | Commercially available wettable powder comprising *P. bilaiae* spores | 52% |

[1]Expressed as a percentage of the spore content (cfu per gram of inoculant composition) measured at time zero.

Example 3

Stable Aqueous Liquid Inoculants Comprising *Penicillium* Spores

Aqueous liquid inoculant compositions comprising *Penicillium bilaiae* spores (ATCC 20851 and/or RS7-1-SD1) were stored for twenty-four weeks at 20° C. alongside a commercially available wettable powder comprising *Penicillium bilaiae* spores (ATCC 20851 and RS7-SD1). As shown in Table 3, the survival rate of *Penicillium* spores was greater in each of the aqueous liquid inoculant compositions than in the commercially available wettable powder.

TABLE 3

| | Inoculant Composition | Viable spores after 24 weeks at 20° C.[1] |
|---|---|---|
| E | PEG 300 + *P. bilaiae* spores (10% w/w) + TERGITOL ™15-S-9 (1% w/w) + 3.45 g/ml trehalose solution (5% w/w) (total water content of the composition = 0.225% w/w) | 70% |
| F | PEG 300 + *P. bilaiae* spores (10% w/w) + TERGITOL ™15-S-9 (1% w/w) + 6.9 g/ml trehalose solution (1% w/w) (total water content of the composition = 0.127% w/w) | 69% |
| G | PEG 300 + *P. bilaiae* spores (10% w/w) + TERGITOL ™15-S-9 (1% w/w) + 1.06 g/ml maltose solution (1% w/w) (total water content of the composition = 0.485% w/w) | 51% |
| H | PEG 300 + *P. bilaiae* spores (10% w/w) + TERGITOL ™15-S-9 (1% w/w) + 2.11 g/ml maltose solution (1% w/w) (total water content of the composition = 0.322% w/w) | 74% |
| I | PEG 300 + *P. bilaiae* spores (10% w/w) + TERGITOL ™15-S-9 (1% w/w) + AGRIMER ™ 30 (2.5% w/w) + OPTIMIZE ® liquid additive (5% w/w) (total water content of the composition = 1.76% w/w) | 156% |

TABLE 3-continued

| | Inoculant Composition | Viable spores after 24 weeks at 20° C.[1] |
|---|---|---|
| J | PEG 300 + *P. bilaiae* spores (10% w/w) + TERGITOL ™15-S-9 (1% w/w) + AGRIMER ™ 30 (5% w/w) + OPTIMIZE ® liquid additive (2.5% w/w) (total water content of the composition = 1.76% w/w) | 123% |
| K | PEG 300 + *P. bilaiae* spores (10% w/w) + TERGITOL ™15-S-9 (1% w/w) + AGRIMER ™ 30 (5% w/w) + OPTIMIZE ® liquid additive (5% w/w) (total water content of the composition = 1.76% w/w) | 112% |
| Control | Commercially available wettable powder comprising *P. bilaiae* spores | 36% |

[1]Expressed as a percentage of the spore content (cfu per gram of inoculant composition) measured at time zero.

Example 4

Stable Aqueous Liquid Inoculants Comprising *Penicillium* Spores

Aqueous liquid inoculant compositions comprising *Penicillium bilaiae* spores (ATCC 20851 and/or RS7B-SD1) were stored for thirty-six weeks at 20° C. alongside a commercially available wettable powder comprising *Penicillium bilaiae* spores (ATCC 20851 and RS7B-SD1). As shown in Table 4, the survival rate of *Penicillium* spores was greater in each of the aqueous liquid inoculant compositions than in the commercially available wettable powder.

TABLE 4

| | Inoculant Composition | Viable spores after 36 weeks at 20° C.[1] |
|---|---|---|
| L | PEG 300 + *P. bilaiae* spores (12.5% w/w) + TERGITOL ™15-S-9 (1% w/w) + OPTIMIZE ® liquid additive (5% w/w) (total water content of the composition = 1.76% w/w) | 28% |
| M | PEG 300 + *P. bilaiae* spores (15% w/w) + TERGITOL ™15-S-9 (1% w/w) + OPTIMIZE ® liquid additive (5% w/w) (total water content of the composition = 1.76% w/w) | 29% |
| N | PEG 300 + *P. bilaiae* spores (20% w/w) + TERGITOL ™15-S-9 (1% w/w) + OPTIMIZE ® liquid additive (5% w/w) (total water content of the composition = 1.76% w/w) | 37% |
| Control | Commercially available wettable powder comprising *P. bilaiae* spores | 28% |

[1]Expressed as a percentage of the spore content (cfu per gram of inoculant composition) measured at time zero.

Example 5

Stable Aqueous Liquid Inoculants Comprising *Penicillium* Spores

Aqueous liquid inoculant compositions comprising *Penicillium bilaiae* spores (ATCC 20851 and/or RS7B-SD1) were stored for forty weeks at 20° C. alongside a commercially available wettable powder comprising *Penicillium bilaiae* spores (ATCC 20851 and RS7B-SD1). As shown in Table 5, the survival rate of *Penicillium* spores was greater in each of the aqueous liquid inoculant compositions than in the commercially available wettable powder.

TABLE 5

| | Inoculant Composition | Viable spores after 40 weeks at 20° C.[1] |
|---|---|---|
| O | PEG 300 + *P. bilaiae* spores (10% w/w) + TERGITOL ™15-S-9 (1% w/w) + OPTIMIZE ® liquid additive (5% w/w) (total water content of the composition = 1.76% w/w) | 33% |
| P | PEG 300 + *P. bilaiae* spores (10% w/w) + TERGITOL ™15-S-9 (1% w/w) + AGRIMER ™ 30 (2.5% w/w) + OPTIMIZE ® liquid additive (2.5% w/w) (total water content of the composition = 0.88% w/w) | 51% |
| Q | PEG 300 + *P. bilaiae* spores (10% w/w) + Atlox 4991 (1% w/w) + OPTIMIZE ® liquid additive (5% w/w) (total water content of the composition = 1.76% w/w) | 75% |
| R | PEG 300 + *P. bilaiae* spores (10% w/w) + Atlox 4991 (1% w/w) + AGRIMER ™ 30 (2.5% w/w) + OPTIMIZE ® liquid additive (2.5% w/w) (total water content of the composition = 1.76% w/w) | 52% |
| Control | Commercially available wettable powder comprising *P. bilaiae* spores | 14% |

[1]Expressed as a percentage of the spore content (cfu per gram of inoculant composition) measured at time zero.

Example 6

Stable Aqueous Licuid Inoculants Comprising *Penicillium* Spores

Aqueous liquid inoculant compositions comprising *Penicillium bilaiae* spores (ATCC 20851 and/or RS7-5-SD1) were stored for seven days at 40° C. alongside a commercially available wettable powder comprising *Penicillium bilaiae* spores (ATCC 20851 and RS7-SD1). As shown in Table 6, the survival rate of *Penicillium* spores was greater in each of the aqueous liquid inoculant compositions than in the commercially available wettable powder.

TABLE 6

| | Inoculant Composition | Viable spores after 7 days at 40° C.[1] |
|---|---|---|
| S | PEG 300 + *P. bilaiae* spores (10% w/w) + TERGITOL ™15-S-9 (1% w/w) + 3.45 g/ml trehalose solution (5% w/w) (total water content of the composition = 0.88% w/w) | 68% |
| A | PEG 300 + *P. bilaiae* spores (10% w/w) + TERGITOL ™15-S-9 (1% w/w) + 6.9 g/ml trehalose solution (5% w/w) (total water content of the composition = 0.635% w/w) | 59% |
| F | PEG 300 + *P. bilaiae* spores (10% w/w) + TERGITOL ™15-S-9 (1% w/w) + 6.9 g/ml trehalose solution (1% w/w) (total water content of the composition = 0.127% w/w) | 89% |
| G | PEG 300 + *P. bilaiae* spores (10% w/w) + TERGITOL ™15-S-9 (1% w/w) + 1.06 g/ml maltose solution (1% w/w) (total water content of the composition = 0.485% w/w) | 83% |
| T | PEG 300 + *P. bilaiae* spores (10% w/w) + TERGITOL ™15-S-9 (1% w/w) + 2.11 g/ml maltose solution (5% w/w) (total water content of the composition = _% w/w) | 30% |
| H | PEG 300 + *P. bilaiae* spores (10% w/w) + TERGITOL ™15-S-9 (1% w/w) + 2.11 g/ml maltose solution (1% w/w) (total water content of the composition = 0.322% w/w) | 73% |
| U | PEG 300 + *P. bilaiae* spores (10% w/w) + TERGITOL ™15-S-9 (1% w/w) + AGRIMER ™ 30 (2.5% w/w) + OPTIMIZE ® liquid additive (2.5% w/w) (total water content of the composition = 0.795% w/w) | 58% |

TABLE 6-continued

| | Inoculant Composition | Viable spores after 7 days at 40° C.[1] |
|---|---|---|
| O | PEG 300 + *P. bilaiae* spores (10% w/w) + TERGITOL ™15-S-9 (1% w/w) + OPTIMIZE ® liquid additive (5% w/w) (total water content of the composition = 1.76% w/w) | 73% |
| L | PEG 300 + *P. bilaiae* spores (12.5% w/w) + TERGITOL ™15-S-9 (1% w/w) + OPTIMIZE ® liquid additive (5% w/w) (total water content of the composition = 1.76% w/w) | 46% |
| M | PEG 300 + *P. bilaiae* spores (15% w/w) + TERGITOL ™15-S-9 (1% w/w) + OPTIMIZE ® liquid additive (5% w/w) (total water content of the composition = 1.76% w/w) | 54% |
| N | PEG 300 + *P. bilaiae* spores (20% w/w) + TERGITOL ™15-S-9 (1% w/w) + OPTIMIZE ® liquid additive (5% w/w) (total water content of the composition = 1.76% w/w) | 81% |
| V | PEG 300 + *P. bilaiae* spores (10% w/w) + Atlox 4991 (1% w/w) + AGRIMER ™ 30 (2.5% w/w) + OPTIMIZE ® liquid additive (2.5% w/w) (total water content of the composition = 0.795% w/w) | 146% |
| C | PEG 300 + *P. bilaiae* spores (10% w/w) + TERGITOL ™15-S-9 (1% w/w) + OPTIMIZE ® liquid additive w/maltose added to 0.43 g/ml (5% w/w) (total water content of the composition = 1.56% w/w) | 105% |
| D | PEG 300 + *P. bilaiae* spores (10% w/w) + TERGITOL ™15-S-9 (1% w/w) + OPTIMIZE ® liquid additive w/trehalose added to 0.42 g/ml (5% w/w) (total water content of the composition = 1.52% w/w) | 78% |
| Control | Commercially available wettable powder comprising *P. bilaiae* spores | 11% |

[1]Expressed as a percentage of the spore content (cfu per gram of inoculant composition) measured at time zero.

Example 7

Stable Aqueous Liquid Inoculants Comprising *Penicillium* Spores

Aqueous liquid inoculant compositions comprising *Penicillium bilaiae* spores (ATCC 20851 and/or RS7B-SD1) were stored for three weeks at 40° C. alongside a commercially available wettable powder comprising *Penicillium bilaiae* spores (ATCC 20851 and RS7B-SD1). As shown in Table 7, the survival rate of *Penicillium* spores was greater in each of the aqueous liquid inoculant compositions than in the commercially available wettable powder.

TABLE 7

| | Inoculant Composition | Viable spores after 3 weeks at 40° C.[1] |
|---|---|---|
| R | PEG 300 + *P. bilaiae* spores (10% w/w) + Atlox 4991 (1% w/w) + AGRIMER ™ 30 (2.5% w/w) + OPTIMIZE ® liquid additive (2.5% w/w) (total water content of the composition = 1.76% w/w) | 36% |
| Control | Commercially available wettable powder comprising *P. bilaiae* spores | 11% |

[1]Expressed as a percentage of the spore content (cfu per gram of inoculant composition) measured at time zero.

Example 8

Stable Aqueous Liquid Inoculants Comprising *Penicillium* Spores

Aqueous liquid inoculant compositions comprising *Penicillium bilaiae* spores (ATCC 20851 and/or RS7B-SD1) were stored for four weeks at 40° C. alongside a commercially available wettable powder comprising *Penicillium bilaiae* spores (ATCC 20851 and RS7B-SD1). As shown in Table 8, the survival rate of *Penicillium* spores was greater in each of the aqueous liquid inoculant compositions than in the commercially available wettable powder.

TABLE 8

| | Inoculant Composition | Viable spores after 4 weeks at 40° C.[1] |
|---|---|---|
| S | PEG 300 + *P. bilaiae* spores (10% w/w) + TERGITOL ™15-S-9 (1% w/w) + 3.45 g/ml trehalose solution (5% w/w) (total water content of the composition = 0.88% w/w) | 8% |
| A | PEG 300 + *P. bilaiae* spores (10% w/w) + TERGITOL ™15-S-9 (1% w/w) + 6.9 g/ml trehalose solution (5% w/w) (total water content of the composition = 0.635% w/w) | 6% |
| F | PEG 300 + *P. bilaiae* spores (10% w/w) + TERGITOL ™15-S-9 (1% w/w) + 6.9 g/ml trehalose solution (1% w/w) (total water content of the composition = 0.127% w/w) | 27% |
| G | PEG 300 + *P. bilaiae* spores (10% w/w) + TERGITOL ™15-S-9 (1% w/w) + 1.06 g/ml maltose solution (1% w/w) (total water content of the composition = 0.485% w/w) | 21% |
| H | PEG 300 + *P. bilaiae* spores (10% w/w) + TERGITOL ™15-S-9 (1% w/w) + 2.11 g/ml maltose solution (1% w/w) (total water content of the composition = 0.322% w/w) | 29% |
| P | PEG 300 + *P. bilaiae* spores (10% w/w) + TERGITOL ™15-S-9 (1% w/w) + AGRIMER ™ 30 (2.5% w/w) + OPTIMIZE ® liquid additive (2.5% w/w) (total water content of the composition = 0.88% w/w) | 83% |
| O | PEG 300 + *P. bilaiae* spores (10% w/w) + TERGITOL ™15-S-9 (1% w/w) + OPTIMIZE ® liquid additive (5% w/w) (total water content of the composition = 1.76% w/w) | 28% |
| L | PEG 300 + *P. bilaiae* spores (12.5% w/w) + TERGITOL ™15-S-9 (1% w/w) + OPTIMIZE ® liquid additive (5% w/w) (total water content of the composition = 1.76% w/w) | 15% |
| M | PEG 300 + *P. bilaiae* spores (15% w/w) + TERGITOL ™15-S-9 (1% w/w) + OPTIMIZE ® liquid additive (5% w/w) (total water content of the composition = 1.76% w/w) | 10% |
| N | PEG 300 + *P. bilaiae* spores (20% w/w) + TERGITOL ™15-S-9 (1% w/w) + OPTIMIZE ® liquid additive (5% w/w) (total water content of the composition = 1.76% w/w) | 23% |
| Q | PEG 300 + *P. bilaiae* spores (10% w/w) + Atlox 4991 (1% w/w) + OPTIMIZE ® liquid additive (5% w/w) (total water content of the composition = 1.76% w/w) | 64% |
| C | PEG 300 + *P. bilaiae* spores (10% w/w) + TERGITOL ™15-S-9 (1% w/w) + OPTIMIZE ® liquid additive w/maltose added to 0.43 g/ml (5% w/w) (total water content of the composition = 1.56% w/w) | 15% |
| D | PEG 300 + *P. bilaiae* spores (10% w/w) + TERGITOL ™15-S-9 (1% w/w) + OPTIMIZE ® liquid additive w/trehalose added to 0.42 g/ml (5% w/w) (total water content of the composition = 1.52% w/w) | 9% |
| Control | Commercially available wettable powder comprising *P. bilaiae* spores | 4% |

[1]Expressed as a percentage of the spore content (cfu per gram of inoculant composition) measured at time zero.

Example 9

Stable Aqueous Liquid Inoculant Enhances On-Seed Stability

An aqueous liquid inoculant composition comprising spores of *Penicillium bilaiae* or a commercially available wettable powder comprising corresponding spores (Table 9) were coated on corn seeds treated with a commercially available pesticide. The coated seeds were stored at 10° C. and 50% relative humidity for 0, 1, 2, 3, 4, 6, 8, 10, 12, 16, 18, 20, 22, 26, 30, 32 or 34 weeks and then assayed for on-seed survivability. As indicated in FIG. 1, the survival rate of *Penicillium* spores was greater on seeds coated with the aqueous liquid inoculant compositions than on seeds coated with the commercially available wettable powder.

TABLE 9

| | Inoculant Composition |
|---|---|
| P | PEG 300 + *P. bilaiae* spores (10% w/w) + TERGITOL ™ 15-S-9 (1% w/w) + AGRIMER ™ 30 (2.5% w/w) + OPTIMIZE ® liquid additive (2.5% w/w) (total water content = 0.88% w/w) |
| Control | Commercially available wettable powder comprising *P. bilaiae* spores |

Example 10

Stable Aqueous Liquid Inoculants

Figure 2:
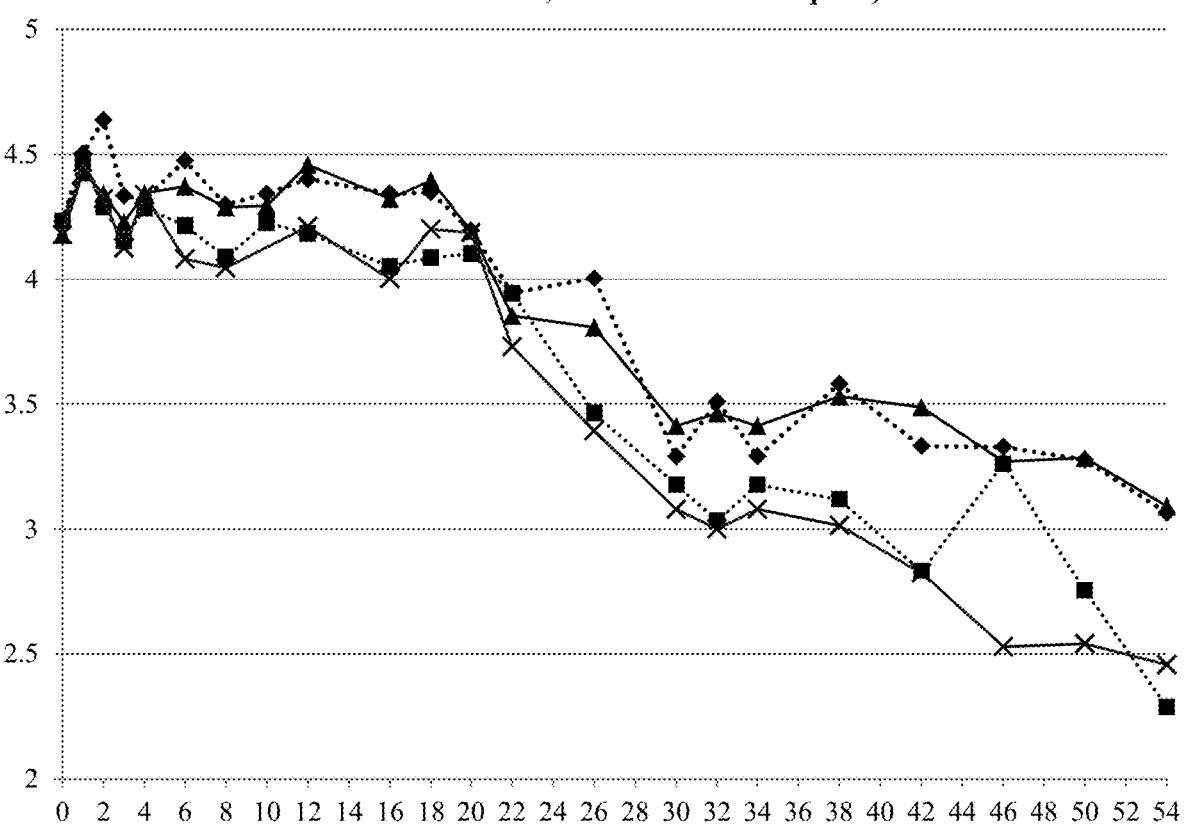
FIG. 2 is a is a graph showing the survivability of *Penicillium bilaiae* spores on corn seeds stored at 10° C. or 20° C. and 50% relative humidity.

Aqueous liquid inoculant compositions comprising spores of *Penicillium bilaiae* (Table 10) were coated on corn seeds treated with a commercially available pesticide. The coated seeds were stored at 10° C. or 20° C. and 50% relative humidity for 0, 1, 2, 3, 4, 6, 8, 10, 12, 16, 18, 20, 22, 26, 30, 32, 34, 38, 42, 46, 50 or 54 weeks and then assayed for on-seed survivability. As indicated in FIG. 2, the *Penicillium* spores survuved for over a year at both 10° C. and 20° C., with and without LCO.

TABLE 10

| | Inoculant Composition |
|---|---|
| P | PEG 300 + *P. bilaiae* spores (10% w/w) + TERGITOL ™ 15-S-9 (1% w/w) + AGRIMER ™ 30 (2.5% w/w) + OPTIMIZE ® liquid additive (2.5% w/w) (total water content = 0.88% w/w) |
| PP | PEG 300 + *P. bilaiae* spores (10% w/w) + TERGITOL ™ 15-S-9 (1% w/w) + AGRIMER ™ 30 (2.5% w/w) + OPTIMIZE ® liquid additive (2.5% w/w) + LCO (<0.00001% w/w) (total water content = 0.88% w/w) |

Example 11

Stable Aqueous Liquid Inoculants Enhance On-Seed Stability

Aqueous liquid inoculant compositions comprising spores of *Penicillium bilaiae* or a commercially available wettable powder comprising corresponding spores were coated on corn seeds treated with a commercially available pesticide. The coated seeds were stored at 10° C. and 50% relative humidity for thirty-six weeks and then assayed for on-seed survivability. As shown in Table 11, the survival rate of *Penicillium* spores was greater on seeds coated with the aqueous liquid inoculant compositions than on seeds coated with the commercially available wettable powder.

TABLE 11

| | Inoculant Composition | Viable spores after 36 weeks at 10° C.[1] |
|---|---|---|
| W | PEG 300 + *P. bilaiae* spores (10% w/w) + ATLOX 4991 (1% w/w) + AGRIMER ™ 30 (2.5% w/w) + OPTIMIZE ® liquid additive (2.5% w/w) (total water content of the composition = 0.88% w/w) | 10% |
| P | PEG 300 + *P. bilaiae* spores (10% w/w) + TERGITOL 15-S-9 + AGRIMER ™ 30 (2.5% w/w) + OPTIMIZE ® liquid additive (2.5% w/w) (total water content of the composition = 0.88% w/w) | 13% |
| Control | Commercially available wettable powder comprising *P. bilaiae* spores | 1% |

[1]Expressed as a percentage of the spore content (cfu per seed) measured at time zero.

Example 12

Stable Aqueous Liquid Inoculants Enhance On-Seed Stability

An aqueous liquid inoculant composition comprising spores of *Penicillium bilaiae* or a commercially available wettable powder comprising corresponding spores were coated on corn seeds treated with a commercially available pesticide. The coated seeds were stored at 20° C. and 50% relative humidity for twenty weeks and then assayed for on-seed survivability. As shown in Table 12, the survival rate of *Penicillium* spores on seeds coated with the aqueous liquid inoculant compositions was equal to or great than that of *Penicillium* spores on seeds coated with the commercially available wettable powder.

TABLE 12

| | Inoculant Composition | Viable spores after 20 weeks at 20° C.[1] |
|---|---|---|
| W | PEG 300 + *P. bilaiae* spores (10% w/w) + ATLOX 4991 (1% w/w) + AGRIMER ™ 30 (2.5% w/w) + OPTIMIZE ® liquid additive (2.5% w/w) (total water content of the composition = 0.88% w/w) | 14% |
| P | PEG 300 + *P. bilaiae* spores (10% w/w) + TERGITOL 15-S-9 + AGRIMER ™ 30 (2.5% w/w) + OPTIMIZE ® liquid additive (2.5% w/w) (total water content of the composition = 0.88% w/w) | 75% |
| Control | Commercially available wettable powder comprising *P. bilaiae* spores | 14% |

[1]Expressed as a percentage of the spore content (cfu per seed) measured at time zero.

Example 13

Stable Aqueous Liquid Inoculants Enhance On-Seed Stability

An aqueous liquid inoculant composition comprising spores of *Penicillium bilaiae* or a commercially available wettable powder comprising corresponding spores were coated on corn seeds treated with a commercially available pesticide. The coated seeds were stored at 30 C and 50% relative humidity for eight weeks and then assayed for on-seed survivability. As shown in Table 13, the survival rate of *Penicillium* spores was greater on seeds coated with the aqueous liquid inoculant compositions than on seeds coated with the commercially available wettable powder.

TABLE 13

| | Inoculant Composition | Viable spores after 8 weeks at 30° C.[1] |
|---|---|---|
| W | PEG 300 + *P. bilaiae* spores (10% w/w) + ATLOX 4991 (1% w/w) + AGRIMER ™ 30 (2.5% w/w) + OPTIMIZE ® liquid additive (2.5% w/w) (total water content of the composition = 0.88% w/w) | 7% |
| P | PEG 300 + *P. bilaiae* spores (10% w/w) + TERGITOL 15-S-9 (1% w/w) + AGRIMER ™ 30 (2.5% w/w) + OPTIMIZE ® liquid additive (2.5% w/w) (total water content of the composition = 0.88% w/w) | 38% |
| X | PEG 300 + *P. bilaiae* spores (10% w/w) + TERGITOL 15-S-9 (1% w/w) + AGRIMER ™ 30 (5% w/w) + OPTIMIZE ® liquid additive (2.5% w/w) (total water content of the composition = 0.88% w/w) | 13% |
| Y | PEG 300 + *P. bilaiae* spores (10% w/w) + TERGITOL 15-S-9 (1% w/w) + AGRIMER ™ 30 (2.5% w/w) + OPTIMIZE ® liquid additive (5% w/w) (total water content of the composition = 0.88% w/w) | 6% |
| Z | PEG 300 + *P. bilaiae* spores (10% w/w) + TERGITOL 15-S-9 + AGRIMER ™ 30 (5% w/w) + OPTIMIZE ® liquid additive (5% w/w) (total water content of the composition = 0.88% w/w) | 11% |
| C | PEG 300 + *P. bilaiae* spores (10% w/w) + TERGITOL ™15-S-9 (1% w/w) + OPTIMIZE ® liquid additive w/maltose added to 0.43 g/ml (5% w/w) (total water content of the composition = 1.56% w/w) | 9% |
| D | PEG 300 + *P. bilaiae* spores (10% w/w) + TERGITOL ™15-S-9 (1% w/w) + OPTIMIZE ® liquid additive w/trehalose added to 0.42 g/ml (5% w/w) (total water content of the composition = 1.52% w/w) | 8% |
| Control | Commercially available wettable powder comprising *P. bilaiae* spores | 5% |

[1]Expressed as a percentage of the spore content (cfu per seed) measured at time zero.

Example 14

Stable Aqueous High-Loading Liquid Inoculants Comprising *Penicillium* Spores

Aqueous liquid inoculant compositions comprising *Penicillium bilaiae* spores (ATCC 20851 and/or RS7B-SD1) are stored for four weeks at 20 C alongside a commercially available wettable powder comprising *Penicillium bilaiae* spores (ATCC 20851 and RS7+-SD1). As shown in Table 14, the survival rate of *Penicillium* spores is greater in each of the aqueous liquid inoculant compositions than in the commercially available wettable powder.

TABLE 14

| | Inoculant Composition | Viable spores after 4 weeks at 20° C.[1] |
|---|---|---|
| AA | PEG 300 + *P. bilaiae* spores (20% w/w) + TERGITOL ™ 15-S-9 (5% w/w) + OPTIMIZE ® liquid additive (5% w/w) (total water content of the composition = 1.59% w/w) | % |
| BB | PEG 300 + *P. bilaiae* spores (30% w/w) + TERGITOL ™ 15-S-9 (5% w/w) + OPTIMIZE ® liquid additive (5% w/w) (total water content of the composition = 1.59% w/w) | % |
| CC | PEG 300 + *P. bilaiae* spores (40% w/w) + TERGITOL ™ 15-S-9 (5% w/w) + OPTIMIZE ® liquid additive (5% w/w) (total water content of the composition = 1.59% w/w) | % |

TABLE 14-continued

| | Inoculant Composition | Viable spores after 4 weeks at 20° C.[1] |
|---|---|---|
| DD | PEG 300 + *P. bilaiae* spores (45% w/w) + TERGITOL ™ 15-S-9 (5% w/w) + OPTIMIZE ® liquid additive (5% w/w) (total water content of the composition = 1.59% w/w) | % |
| Control | Commercially available wettable powder comprising *P. bilaiae* spores | % |

[1]Expressed as a percentage of the spore content (cfu per gram of inoculant composition) measured at time zero.

That which is claimed:

1. A method comprising introducing an aqueous inoculant composition into a plant growth medium, said aqueous inoculant composition comprising:
   microbial spores comprising about 0.1 to about 15% by weight of said aqueous inoculant composition;
   one or more protectants comprising about 0.5 to about 5% by weight of said aqueous inoculant composition, said one or more protectants comprising one or more sugars and/or one or more sugar alcohols;
   one or more dispersants comprising about 0.1 to about 5% by weight of said aqueous inoculant composition; and
   one or more polyethylene glycols comprising about 75 to about 95% by weight of said aqueous inoculant composition.

2. The method of claim 1, wherein said one or more protectants comprises about 1 to about 2% by weight of said aqueous inoculant composition.

3. The method of claim 1, wherein said one or more protectants comprises one or more disaccharides and one or more sugar alcohols.

4. The method of claim 1, wherein said one or more protectants comprises maltose, sucrose and/or trehalose.

5. The method of claim 1, wherein said one or more protectants comprises arabitol, mannitol, sorbitol and/or xylitol.

6. The method of claim 1, wherein said one or more dispersants comprises about 1 to about 4% by weight of said aqueous inoculant composition.

7. The method of claim 1, wherein said one or more dispersants comprises one or more non-ionic surfactants and/or one or more wetting agents.

8. The method of claim 1, wherein said one or more dispersants comprises one or more alcohol ethoxylates.

9. The method of claim 1, wherein said one or more dispersants comprises one or more naphthalene sulfonates.

10. The method of claim 1, wherein water comprises less than 5% by weight of said aqueous inoculant composition.

11. The method of claim 1, wherein water comprises at least 0.75% by weight of said aqueous inoculant composition.

12. The method of claim 1, wherein said one or more polyethylene glycols comprises about 80 to about 90% by weight of said aqueous inoculant composition.

13. The method of claim 1, wherein said one or more polyethylene glycols comprises PEG 200, PEG 300 and/or PEG 400.

14. The method of claim 1, wherein said aqueous inoculant composition further comprises one or more pesticides.

15. The method of claim 1, wherein said aqueous inoculant composition further comprises one or more lipo-chi-tooligosaccharides.

16. The method of claim 1, wherein said aqueous inoculant composition further comprises one or more chitin oligomers.

17. The method of claim 1, wherein said aqueous inoculant composition further comprises one or more flavonoids.

18. The method of claim 1, wherein said aqueous inoculant composition further comprises one or more nutrients.

19. The method of claim 1, wherein said aqueous inoculant composition is introduced into said plant growth medium as a coating on a plant seed.

20. The method of claim 1, wherein said aqueous inoculant composition is introduced into said plant growth medium as part of an in-furrow application.

21. The method of claim 1, wherein said microbial spores comprise *Penicillium* spores.

22. The method of claim 1, wherein said microbial spores comprise *Bacillus* spores.

23. The method of claim 1, wherein said microbial spores comprise *Trichoderma* spores.

24. A method comprising applying an aqueous inoculant composition to a plant propagation material to produce a treated plant propagation material, said aqueous inoculant composition comprising:

microbial spores comprising about 0.1 to about 15% by weight of said aqueous inoculant composition;

one or more protectants comprising about 0.5 to about 5% by weight of said aqueous inoculant composition, said one or more protectants comprising one or more sugars and/or one or more sugar alcohols;

one or more dispersants comprising about 0.1 to about 5% by weight of said aqueous inoculant composition; and one or more polyethylene glycols comprising about 75 to about 95% by weight of said aqueous inoculant composition.

25. The method of claim 24, further comprising introducing said treated plant propagation material into a plant growth medium.

* * * * *